(12) United States Patent
Weber

(10) Patent No.: US 7,742,562 B2
(45) Date of Patent: Jun. 22, 2010

(54) LOWER-TORSO ASSEMBLY OF A TREATMENT COUCH USEABLE IN AN X-RAY ENVIRONMENT

(75) Inventor: Adam J. Weber, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 264 days.

(21) Appl. No.: 11/823,657

(22) Filed: Jun. 27, 2007

(65) Prior Publication Data

US 2009/0003532 A1    Jan. 1, 2009

(51) Int. Cl.
   *G21K 5/08*    (2006.01)
(52) U.S. Cl. .............................. 378/68; 378/209; 5/601
(58) Field of Classification Search ................ 378/20, 378/65, 209, 68, 62; 5/601
   See application file for complete search history.

(56) References Cited

U.S. PATENT DOCUMENTS

| | | | |
|---|---|---|---|
| 455,168 A | | 6/1891 | Case |
| 1,201,274 A | | 10/1916 | Denquer |
| 2,893,164 A | | 7/1959 | Martin |
| 2,933,850 A | | 4/1960 | Martin |
| 3,753,592 A | * | 8/1973 | Jensen ................. 297/284.1 |
| 3,868,103 A | | 2/1975 | Pageot et al. |
| 4,582,050 A | | 4/1986 | Willis |
| 4,984,774 A | | 1/1991 | Zupancic et al. |
| 5,308,359 A | | 5/1994 | Lossing |
| 5,345,631 A | | 9/1994 | Saperstein et al. |
| 5,596,775 A | | 1/1997 | Dimatteo |
| 5,724,970 A | | 3/1998 | Votruba |
| 6,375,355 B1 | * | 4/2002 | Fortin ..................... 378/209 |
| 6,378,149 B1 | | 4/2002 | Sanders et al. |
| 6,651,279 B1 | | 11/2003 | Muthuvelan |
| 6,857,147 B2 | | 2/2005 | Somasundaram |
| 6,948,688 B1 | | 9/2005 | Payne et al. |
| 2002/0029419 A1 | | 3/2002 | Weil et al. |
| 2005/0028279 A1 | | 2/2005 | De Mooy |
| 2005/0234327 A1 | | 10/2005 | Saracen |
| 2006/0002511 A1 | * | 1/2006 | Miller et al. ................. 378/65 |
| 2007/0169265 A1 | | 7/2007 | Saracen et al. |
| 2009/0003532 A1 | | 1/2009 | Weber |

OTHER PUBLICATIONS

"A Whole New Angle in Cardiology", Siemens Medical, 2003, Data, 8 pages.
"A Whole New Angle in Cardiology", Siemens Medical, 2003, Technical, 4 pages.
"Accuray Unveils the Next Generation in Robotic Radiosurgery", Accuray Incorporated Press Release, Oct. 17, 2005, 2 pgs., http://www.accuray.com/media/pressreleases/yr2005/pr101705.aspx.
Coste-Maniere, E., "Robotic whole body stereotactic radiosurgery: clinical advantages of the CyberKnife® integrated system", The International Journal of Medical Robotics +Computer Assisted Surgery, 2005, www. roboticpublications.com, 14 pages.
International Search Report and Written Opinion, PCT/US08/04882 filed Apr. 15, 2008, mailed Aug. 1, 2008.

* cited by examiner

*Primary Examiner*—Courtney Thomas
(74) *Attorney, Agent, or Firm*—Blakely, Sokoloff, Taylor & Zafman LLP

(57) ABSTRACT

A treatment couch having a tabletop that has a radiolucent region, and a lower-torso assembly that has a first slide member coupled to a slot of the tabletop, a second slide member coupled to a slot of the first slide member, and a link member coupled to the first and second slide members. The lower-torso assembly may be configured to adjust a patient along a longitudinal direction relative to a shoulder line of the tabletop while the lower-torso assembly remains outside the radio lucent region of the tabletop.

68 Claims, 25 Drawing Sheets

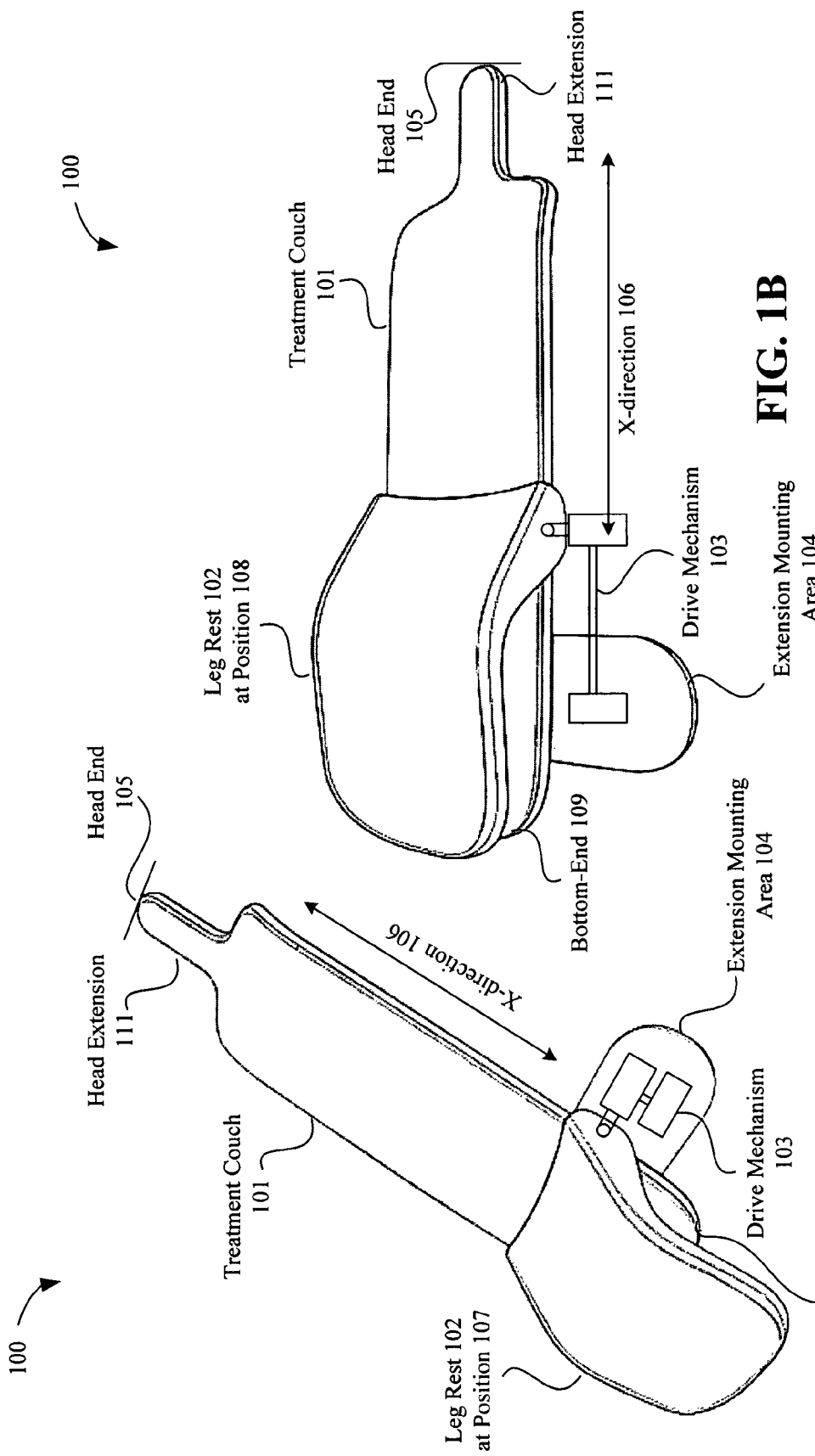

1500 loading a patient onto a treatment couch having a tabletop and a lower-torso assembly 1501

adjusting the patient along a longitudinal direction relative to a shoulder line of the tabletop using the lower-torso assembly while the lower-torso assembly remains outside a radiolucent region of the tabletop 1502

FIG. 15

1600 moving a treatment couch having a tabletop and a lower-torso assembly along one or more degrees of freedom using a first robotic arm 1601

adjusting a patient along a longitudinal direction relative to a shoulder line of the tabletop of the treatment couch using the lower-torso assembly while the lower-torso assembly remains outside a radiolucent region of the tabletop 1602

FIG. 16

LOWER-TORSO ASSEMBLY OF A TREATMENT COUCH USEABLE IN AN X-RAY ENVIRONMENT

TECHNICAL FIELD

Embodiments of the present invention pertain in general to the patient support systems, and more particularly, patient support systems used in X-ray environments.

BACKGROUND

Treatment couches have been used in various medical operations. Some examples of treatment couches are surgery tables, operating tables, dentist chairs, and treatment couches for radiation treatment systems. Some examples of radiation treatment systems are gantry-based radiation treatment system and robot-based linear accelerator system. Treatment couches, in general, may be used to support a patient during these medical operations. Treatment couches may also be used to position a patient into a specific position in a treatment room. For example, a treatment couch may be used to position a patient with respect to a linear accelerator or other radiation sources for both gantry-based and robot-based treatment systems.

Another conventional design of a treatment couch used for medical operations is a reclining chair. It has two portions; a base portion, and a reclining portion. The reclining portion of the reclining chair allows a patient to sit back during a scanning procedure. In one conventional design, the reclining portion and the base portion move together to recline a patient backwards for treatment. In another conventional design, the reclining portion and the base portion may move in a folding and unfolding motion to and from one another. This folding and unfolding motion allows a patient to sit on the chair for patient loading purposes, and then allows the patient to sit back, or recline back for patient treatment purposes. These folding functions, however, do not include any mechanism to physically move the patient towards the head end of the chair or table, or to physically move the patient to a specific position on the table or chair. These conventional designs merely position the patient forwards and backwards with respect to an upright sitting position of the reclining chair.

Another conventional design of a patient positioning system used for medical operations is a treatment couch having a leg rest and a drive mechanism, as illustrated in FIG. 1A. Patient positioning system 100 of FIG. 1A includes treatment couch 101, leg rest 102, drive mechanism 103, and extension mounting area 104. Treatment couch 101 is coupled to leg rest 102, and the drive mechanism 103 is coupled to leg rest 102 and extension mounting area 104. The drive mechanism 103 is coupled to the leg rest 102 by a rail or rack and pinion. The rail or rack is mounted to the side of the treatment couch to accommodate various patient heights. The leg rest 102 of FIG. 1A is positioned at a first position on the treatment couch 101, position 107, which is towards the bottom-end 109 of the treatment couch 101 The first position 107 may be used for loading and/or unloading a patient onto and/or from treatment couch 101. The drive mechanism 103 moves the leg rest 102 in one translational direction, x-direction 106, relative to a head end 105 of the treatment couch 101. The leg rest 102, which supports the lower-half of the patient's body, can be moved up and down with respect to the head end 105 using the drive mechanism 103 to adjust an upper-half of the patient relative to the head end 105 of the treatment couch 101.

One type of drive mechanism is a motorized ball screw drive system 150, which includes two motors, mounted on the back of the treatment couch, such as at off-center lines, as illustrated in FIG. 1C. The dual motorized ball screw drive system 150 of FIG. 1C includes motors 151 and 152, belts 153 and 154, multiple pulleys 155, ball screws 156 and 157, and cars 158 and 159 (e.g., ball screw nuts). The dual motorized ball screw drive system 150 is used to convert rotational motion of the motors 151 and 152 about axis 162(1) and axis 162(2) into linear motion of the leg rest 102 or treatment couch 101 in the x-direction 106. As the motors 151 and 152 rotate, the motors drives the belts 153 on pulleys 155, which in turn rotate the ball screws 156 and 157, which in turn drives the bar screw nuts 158 that are coupled to the leg rest 102 in a linear, translational direction (e.g., 106) along rail slides 160, which in turn drives the leg rest 102 in a linear, translational direction (e.g., 106).

The patient positioning system 100 may also be used in other positions, such as a horizontal treating position, as illustrated in FIG. 1B. Leg rest 102 of FIG. 1B is positioned at a second position on the treatment couch 101, position 108, which is closer to the head end 105 of the treatment couch 101 than position 107. Position 108 may be used for treating a patient on treatment couch 101. The patient may be loaded onto the treatment couch in position 107, and then, the leg rest 102 may be moved in the translational x-direction 106 up or down (away from or towards the head end 106) to position the patient on the treatment couch to a treating position, position 108. However, in this conventional design, the patient is adjusted after the patient is loaded onto the treatment couch. Adjusting the patient on the treatment couch 101 using the drive mechanism 103 and leg rest 102 along the seat back of the treatment couch 101 may cause discomfort to the patient, such as the skin of the patient catching on the surface due the friction between the upper-half of the patient's body and the treatment couch 101, the skin of the patient burning from being rubbed across the seat back surface, or the skin of the patient getting pinched between the leg rest 102 and the treatment couch 101, as the leg rest moves from one position to another in the x-direction 106. In another embodiment, a sliding member may be coupled to the lower-torso assembly 202 so that it moves with the translational motion of the lower-torso assembly 202 in the longitudinal direction 206. The sliding member may be a thin back piece, and may be used to reduce the friction between the upper-half of the patient's body and the tabletop 201. The sliding member may also be used to prevent the upper-half of the patient's back from directly lying on the tabletop 201 to help prevent the patient from getting pinched between the lower-torso assembly 202 and the tabletop 201 as the leg rest moves from one position to another in the longitudinal direction 206. It should be noted, however, that the lower-torso assembly 202 may be adjusted prior to the loading of the patient on the treatment couch 200. The lower-torso assembly 202 may be positioned to the appropriate height to align the patient's shoulders with the shoulder line 207 before the patient is loaded onto the treatment couch 200. This prevents the patient from experiencing discomfort from the skin of the patient sliding across the surface of the tabletop 201 when the lower-torso assembly 202 is adjusted.

In addition the discomfort to the patient, some components of the treatment couch 101 of FIGS. 1A and 1B are located inside an imaging zone of the patient for certain height positions. Although the rails or rack of the drive mechanism may not be located within the imaging zone of other heights, such as the 1% female height, the components of the drive mechanism may be within the imaging zone of patients of other heights. For example, during treatment of the 99% male, some components, such as the rail or rack, are exposed in the images of the patient, since they are located within the imaging zone of the patient. For example, the imaging zone of a patient may extend from the head to above the lowest point of the rear pelvic area of the patient while the patient is in a sitting position on the leg rest and treatment couch. In effect, the drive mechanism 103 introduces metal in a treatable region of the patient. Even if the rails or racks were made of materials, such as plastic, instead of metal, these components would still appear in the images of the x-rays within that region.

Similarly, even if the treatment couch 101 were to have a radiolucent region that allows the passage of x-rays or other radiation or is entirely invisible in x-ray photographs or under fluoroscopy, some components of the drive mechanism would be disposed inside this radiolucent region, causing these components to appear in the x-ray images of the radiolucent region. As such, the drive mechanism 103 may not be used in an x-ray environment for all heights of patients.

Another conventional design of a patient positioning system used for medical operations is a treatment couch having a base portion and multiple detachable portions, as illustrated in FIG. 1D. Treatment couch 101 of FIG. 1D includes a base portion 171, and the detachable portions 172(1)-(N) (e.g., multiple back-rests) of the treatment couch 101. One detachable portion 172(1), for example, is coupled to the base portion 171 of the treatment couch 101. Each detachable back-rest 172 has a height 174. The detachable portions 172 may be used to adjust a height of the treatment couch 101 to accommodate differing heights of patients. The detachable portions 172 are used to position a head of a patient with respect to a head end 105 of the treatment couch 101 or to adjust an upper-half of a patient relative to a head end 105 of the treatment couch 101.

The treatment couch 101 of FIG. 1D may include a leg rest 102. Leg rest 102 may be detachable, and may have one or more pivot points for one or more articulations. The multiple back-rests of treatment couch 101 may be mounted to the base portion 171 using a tab portion 173 of the back-rest 172 that is inserted into the base portion 171. The tab portion 173 may be used to easily remove the back-rests 172 from the base portion 171, to change the effective height 174 of the treatment couch 101. The multiple back-rests may minimize the range of adjustment necessary for any given patient. One of the multiple back-rests may include a large-sized back-rest to accommodate the ninety-nine percentile male (e.g., 75.6 inches), and another small-sized back-rest to accommodate the, as well as intermediate-sized back rests. The multiple back-rests may be stored on a rack on the wall of a treatment room.

Although the multiple detachable portions 172(1)-(N) may be used to accommodate different heights of patients, the detachable portions need to be a reasonable weight, such as 25 pounds (lbs), to allow an operator to lift the detachable portion from the base portion and to move the detachable portions to and from the rack on the wall of the treatment room. Although materials, such as carbon fiber, could be used to reduce the weight of the detachable portion, the detachable portions still need to support a patient load up to 500 pounds (lbs).

Another conventional design of a patient positioning system used for medical operations is a treatment couch having tabletop and a detachable leg rest, such as the leg rest 102 illustrated in FIGS. 1A-1D. Similar to the detachable portions 172, the datable leg rest needs to be a reasonable weight, such as 25 pounds (lbs) to allow an operator to lift and carry the detachable leg rest. Similarly, materials such as carbon fiber could be used to reduce the weight of the detachable leg rest, but the leg rest still needs to support a patient load up to 500 pounds (lbs). However, in these conventional designs having the leg rest 102, when tipping the treatment couch 101 to allow loading of the patient, such as illustrated in FIG. 1A, the seat pan of the leg rest could only be lowered to approximately 24 inches above the floor. However, the seat pan of the leg rest needs to be about 15-18 inches from the floor to accommodate loading of patients of smaller heights. As such, the leg rest 102 only allowed loading of patients of certain heights using a seat pan height of 24 inches or more.

BRIEF DESCRIPTION OF THE DRAWINGS

Embodiments of the present invention are illustrated by way of example, and not by way of limitation, in the figures of the accompanying drawings and in which:

FIG. 1A illustrates a conventional patient positioning system including a treatment couch, a leg rest, and drive mechanism in a loading position.

FIG. 1B illustrates the conventional patient positioning system of FIG. 1A in a treating position.

FIG. 15 illustrates a flow chart of one embodiment of a method for adjusting a patient along a longitudinal direction relative to a shoulder line of a tabletop of a treatment couch.

FIG. 16 illustrates a flow chart of one embodiment of a method for operation of a robotic treatment couch.

DETAILED DESCRIPTION

Figure 1C:
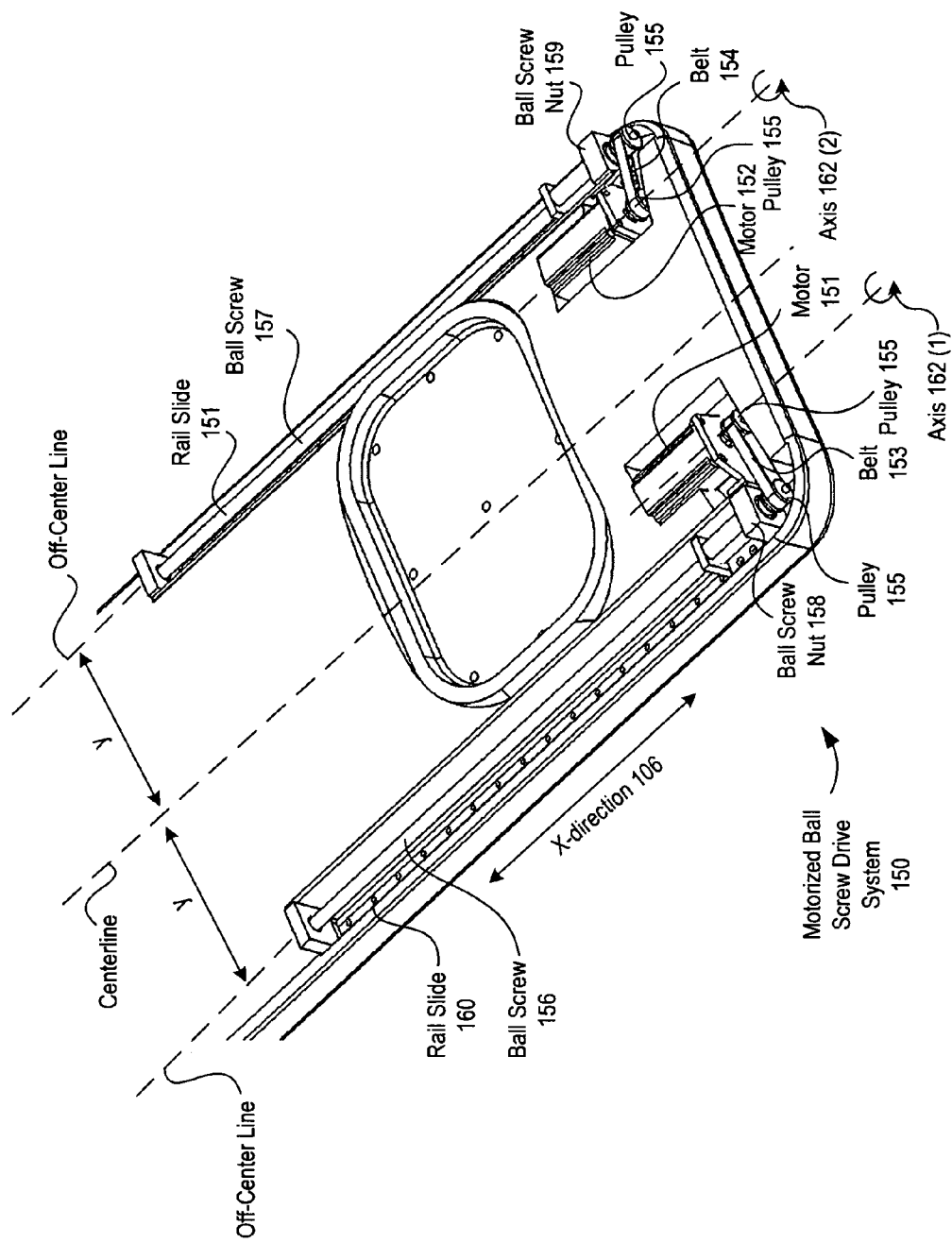
FIG. 1C illustrates a conventional drive mechanism including a motorized ball screw drive system, including two motors, mounted on off-center lines of the treatment couch.
Figure 1D:
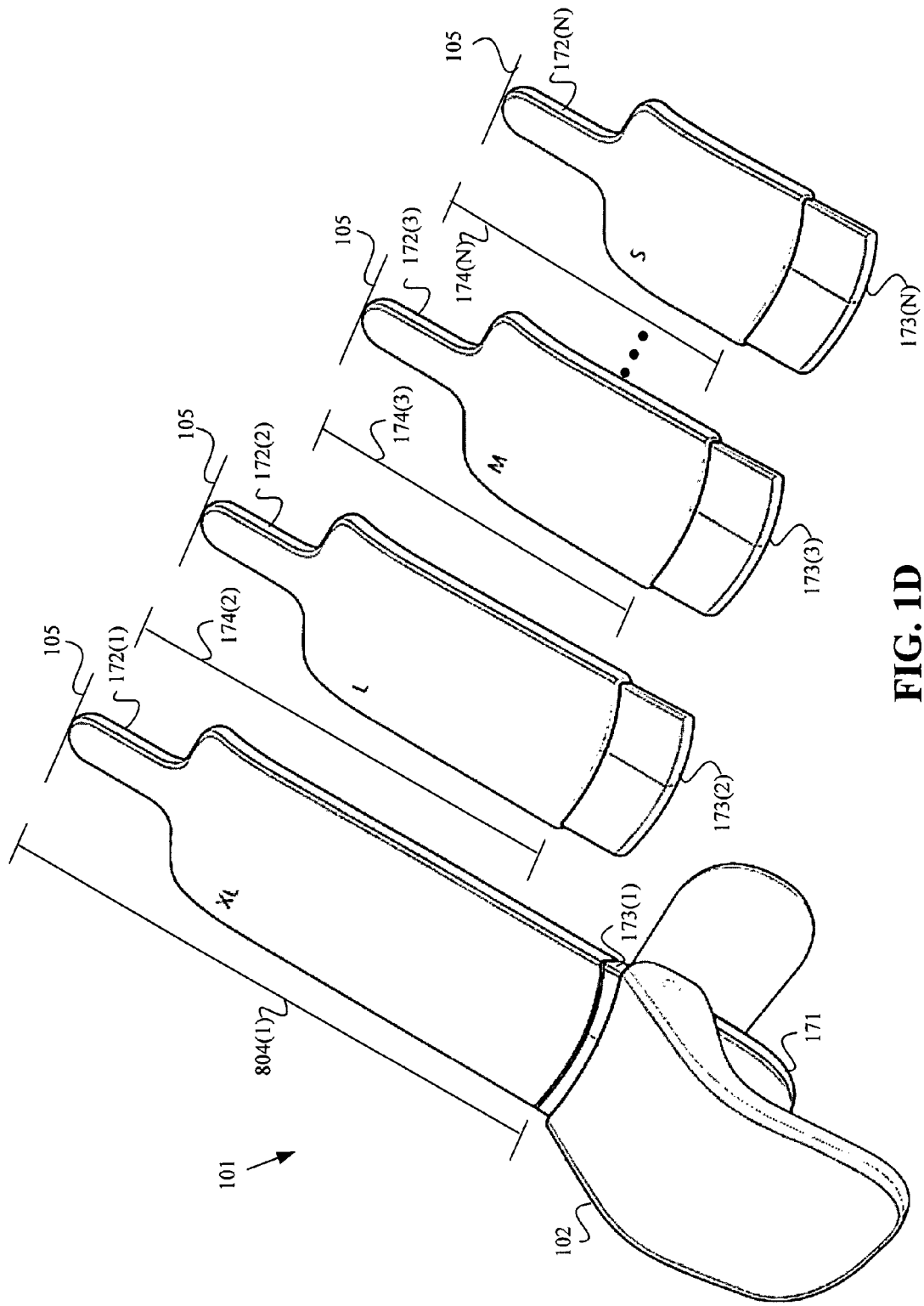
FIG. 1D illustrates another conventional patient positioning system of a treatment couch including a base portion and multiple detachable portions.

In the following description, numerous specific details are set forth such as examples of specific components, devices, methods, etc., in order to provide a thorough understanding of the present embodiments. It will be apparent, however, to one skilled in the art that these specific details need not be employed to practice the present embodiments. In other instances, well-known materials or methods have not been described in detail in order to avoid unnecessarily obscuring the present embodiments.

A lower-torso assembly of a treatment couch useable in an X-ray environment is described for adjusting a patient along a longitudinal direction relative to a shoulder line of the treatment couch while the lower-torso assembly remains outside a radiolucent region of the treatment couch. The lower-torso assembly includes a first slide member coupled to a slot of the tabletop, a second slide member coupled to a slot of the first slide member, and a link member coupled to the first and second slide members. The lower-torso assembly may be configured to adjust the patient along the longitudinal direction of the tabletop while the lower-torso assembly remains outside the radiolucent region of the tabletop. It should be noted that patient, as used herein, may be a human patient, or alternatively, an animal patient.

The lower-torso assembly is an adjustable mechanism that allows conversion between a flat tabletop to a seat for supporting the patient. While in the seat configuration, the lower-torso assembly may be adjusted relative to a head end of the treatment couch to accommodate various heights of patients in positioning the shoulders of the patient to a shoulder line of the tabletop. The lower-torso assembly can be implemented so that all components of the lower-torso assembly, which may be metal, are disposed outside a radiolucent region of the tabletop. The lower-torso assembly remains outside an imaging zone through which x-rays pass. As such, the lower-torso assembly may be fully adjustable and implemented within an x-ray environment. The lower-torso assembly may provide a flat tabletop, a knee bolster for the patient's knee when the patient is lying flat on the tabletop, or a seat for the patient when the loading the patient onto the tabletop, while in certain configurations.

The tabletop and lower-torso assembly are configured to provide a support assembly that has a flat surface upon which the patient is disposed in a first configuration, and a support assembly having a seat to support a lower-torso area of the patient in a second configuration. The lower-torso assembly is configured to support a patient load up to 500 pounds (lbs). The tabletop is also configured to support a patient load up to 500 pounds (lbs). Since the lower-torso assembly is integrated with the tabletop of the treatment couch, the weight restrictions of the detachable portions or detachable leg rests of the conventional designs is not applicable to the lower-torso assembly. The lower-torso assembly can also be configured to be adjusted before the patient is loaded onto the treatment couch so that the patient is not moved along the tabletop in a discomforting fashion, as described above with respect to the conventional designs.

The embodiments described herein may also be implemented in a treatment couch of a patient positioning system, used in connection with a radiation treatment system. In one embodiment, the radiation treatment system may be a robot-based linear accelerator treatment system. Alternatively, the radiation treatment system may be a gantry-based radiation treatment system. It should also be appreciated that the embodiments described herein may alternatively be used for other medical applications, for example, as an operating room (OR) table, or as a supporting device in CT scanning or in MRI process, and the like. For example, the embodiments described herein may be used to position the patient on the treatment couch relative to the shoulder line before imaging the patient using a CT scanner or an MRI scanner. Similarly, before a patient is operated on during a non-radiosurgery treatment, the upper-half of the patient may need to be imaged to confirm a position of a tumor within the patient before the patient is cut open to remove the tumor, and the patient may be adjusted relative to the shoulder line to allow the imaging zone to be free of obstructions from the lower-torso assembly during imaging.

The patient positioning system may include a treatment couch coupled to a stand, or alternatively, to a positioning system. In one embodiment, the positioning system may include a robotic arm, having one or more degrees of freedom, coupled to the treatment couch. Alternatively, the treatment couch is not coupled to a robotic arm, but rather coupled to other types of motorized mechanisms for positioning the treatment couch. In other embodiments, the positioning system does not include a robotic arm, but rather another type of motorized mechanisms known by those of ordinary skill in the art for positioning the treatment couch. For example, in one embodiment, the patient positioning system includes motorized mechanisms, which provides patient positioning along five automated degrees of freedom (e.g., inferior-superior, anterior-posterior, right-left, roll and pitch) and a manual control of a sixth (e.g., yaw) degree of freedom while accommodates a patient load up to 350 pounds (lbs). Alternatively, the patient positioning system may be other types of patient positioning systems known by those of ordinary skill in the art used to position a treatment couch.

Figure 2A:
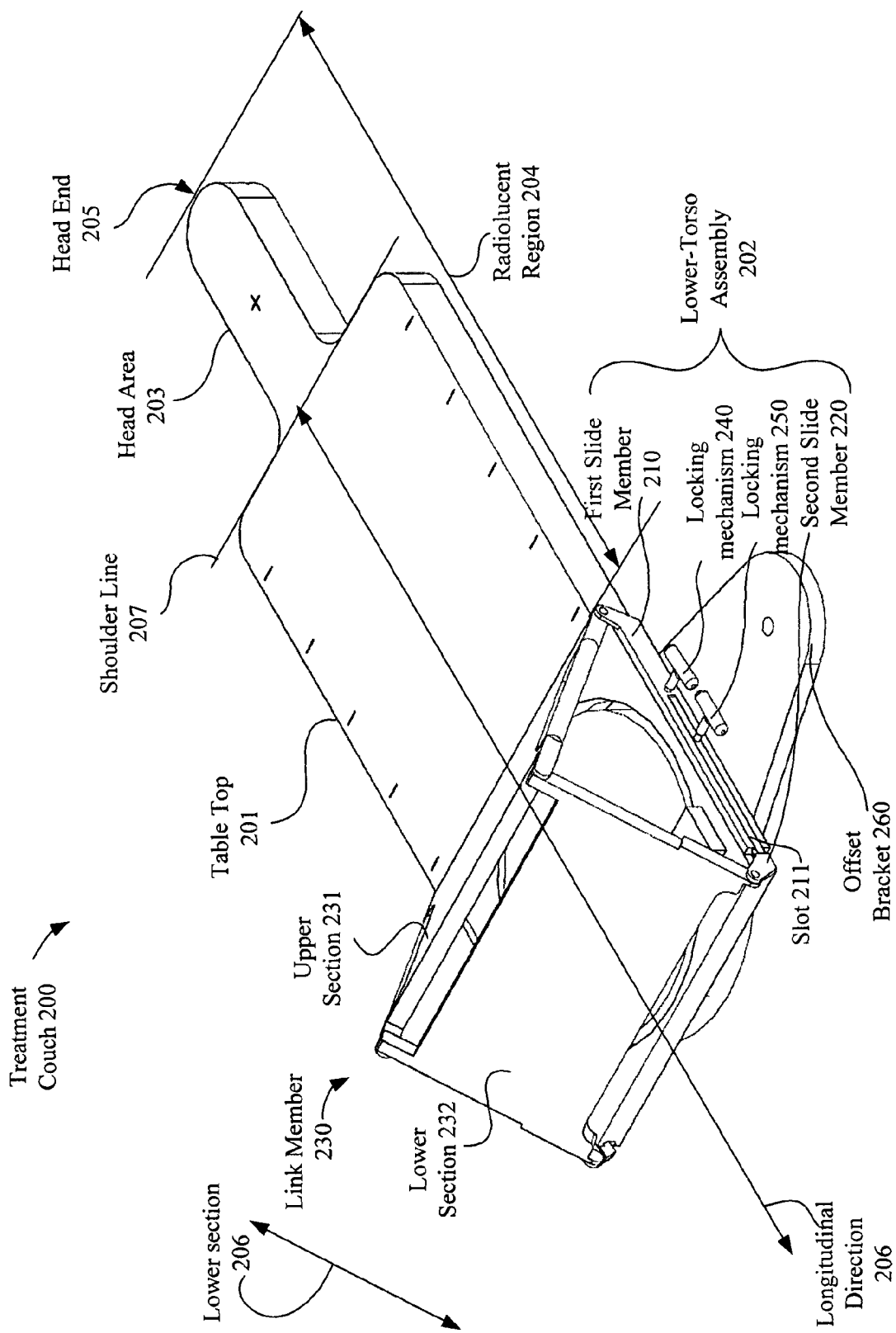
FIG. 2A illustrates a perspective view of one embodiment of treatment couch having a tabletop and a lower-torso assembly.

FIG. 2A illustrates a perspective view of one embodiment of treatment couch 200 having a tabletop 201 and a lower-torso assembly 202. The treatment couch 200 includes a lower-torso assembly 202 coupled to a lower section 206 of the tabletop 201. The tabletop 201 includes a radiolucent region 204. The radiolucent region 204 allows the passage of x-rays or other radiation through the tabletop 201. The radiolucent region 204 is configured to be substantially invisible in x-ray images or under fluoroscopy. It should be noted that the tabletop 201 may still show up slightly in the x-ray images. In one embodiment, the tabletop's visibility in the photograph is limited to less than approximately 0.8 mm of aluminum equivalency. Alternatively, the tabletop's visibility is limited to other values more or less than 0.8 mm of aluminum equivalency. The tabletop 201 may be made of materials that are radiolucent or radio transparent so as to not interfere with the imaging of the patient disposed on the tabletop 201. In one embodiment, the radiolucent region 204 is substantially from the head end 205 of the tabletop 201 to the lower-torso assembly 202. The lower-torso assembly 202 remains outside the radiolucent region 204 of the tabletop 201 during treatment of the patient. The lower-torso assembly 202 remains outside the radiolucent region 204 regardless of the height of the patient disposed on the tabletop 201, as described herein. The tabletop 201 also includes a shoulder line 207, a head area 203, a head end 205, and a lower section 206.

When the patient is disposed on the treatment couch 200, the patient should be positioned so that the head of the patient is substantially located in the head area 203, and so that the shoulders of the patient are substantially located at the shoulder line 207. The lower-torso assembly 202 may be used in positioning patients of differing heights so that the shoulders are aligned with respect to our common line on the tabletop 201, such as the shoulder line 207 or the head end 205, regardless of the height of the particular patient. The embodiments described herein may accommodate a majority of differing heights of people, such as a range from one percentile female (e.g., 58.1 inches) to the ninety-nine percentile male (e.g., 75.6 inches). Table 1-1 includes one exemplary embodiment of numeric variations of patients on the tabletop 201.

TABLE 1-1

|  | Seat Height | Shoulder Height |  | Shoulder Head Length |
|---|---|---|---|---|
| 99% Male | 1018 | 685 | mm | 333 |
| 1% Female | 783 | 496 | mm | 287 |
| Delta | 235 | 189 | mm | 46 |
|  | 9.251969 | 7.440945 | inch | 1.811024 |

In one embodiment, in order to accommodate the 99% male, the lower-torso assembly is positioned to provide a seat height of approximately 1018 mm (e.g., length 219). The 99% male has an approximate shoulder height of 685 mm. By positioning the lower-torso assembly to the seat height of approximately 1018 mm, the patient's shoulders can be adjusted at the shoulder line 207. In this example, the head area 203 has a shoulder to head length of 333 mm (e.g., length 219). In one embodiment, the shoulder to head length is approximately the length 215 of the head area 203 of the tabletop 201, and the seat height is approximately the length 219 of the tabletop 201 of FIG. 2C. Similarly, for the 1% female, the seat height is approximately 783 mm, the shoulder height is approximately 496 mm, and the shoulder to head length is approximately 287 mm. In this embodiment, the difference or delta between the 99% male and the %1 female for the seat height is approximately 235 mm (approximately 9.252 inches), the shoulder height is approximately 189 mm (approximately 7.44 inches), and the shoulder to head length is approximately 46 mm (approximately 1.8811 inches). In one embodiment, approximately 2 inches may be used as the difference between the 99% male and the 1% female to accommodate attachment of a mounting device, which is used to secure a mask to the patient to limit the patient's mobility during treatment. Alternatively, other values may be used for the seat height, the shoulder height, and the shoulder to head length.

As described above, the variation between the tallest patient and the shortest patient is a little over 9 inches. If the head of each patient were aligned to the same spot every time, then the shortest patient would not have their shoulders supported. As such, by aligning the shoulders of the patient to the common shoulder line 207, the shoulders of the patient regardless of height are supported by the tabletop. It should be noted that the tabletop as illustrated in the Figures includes a head area 203 that has a width that is less than the width of the tabletop. In one embodiment, by having the width of the head area 203 be less than the width of the tabletop 201, access to the head area 203 is increased. This particular shape, for example, allows a robot-based LINAC to get closer to the patient in the cut-out areas. Alternatively, other shapes of tabletops may be used. It should also be noted that using other shapes, the patient may be aligned to the head end 205, or other common line on the tabletop 205, instead of the common shoulder line 207.

A lower-torso assembly 202 is configured to adjust a particular patient along a longitudinal direction 206 relative to the shoulder line 207 of the tabletop 201. The lower-torso assembly 202 is configured to remain outside the radiolucent region 204 of the tabletop 201, while adjusting the position of the lower-torso assembly 202 to position the patient's shoulders substantially at the shoulder line 207. In one exemplary embodiment, a mask is placed on the patient's head to secure the patient to the tabletop 201 and to prevent the head from moving during treatment. The mask may be coupled to a mounting device, which secures the mask to the tabletop 201. In order to secure the mask to the patient's head, the patient's head must be aligned and positioned correctly towards the head end 205 of the tabletop 201. By moving the lower-torso assembly 202 the effective position of the patient may be adjusted relative to the head and 205 of the tabletop 201, for example, for allowing the mask to be secured or mounted to the tabletop 201.

In one embodiment, the tabletop 201 is coupled to an external device to position the tabletop 201 in three dimensional space in a treatment room. In one embodiment the external device is a robotic arm of a patient positioning system, as described below. In another embodiment, the external device is other types of motorized mechanisms of a patient positioning system. Alternatively, the tabletop is coupled to a stand. The tabletop 201 may be coupled to the robotic arm by way of the mounting plate that couples directly to the robotic arm. Alternatively, the tabletop 201 may be coupled to an offset bracket 260. The offset bracket 260 may be coupled to the back side of the tabletop 201 at the lower section 206. Alternatively the offset bracket 260 may be coupled to the side of the tabletop 201. The offset bracket 260 may be used to mount the treatment couch 200 to a stand, or to a patient positioning system, such as a robotic arm, or another type of external device for positioning the treatment couch. It should be noted that the extension mounting area may also be disposed at another location along the periphery of the tabletop 201 other than as shown in FIG. 2A, such as at the bottom-end (opposite the head-end 205) of tabletop 201. In one embodiment, the treatment couch 200 is coupled to a robotic arm. In one embodiment, a motor is disposed at the lower section 232 of the tabletop 201 to rotate the tabletop 201 in one degree of freedom (DOF). This degree of freedom may be an additional degree of freedom of the robotic arm. Alternatively, the treatment couch 200 may be coupled to other types of positioning systems, or even a stand.

In one embodiment, the lower-torso assembly 202 includes a first slide member 210 that is coupled to a slot 208 (illustrated in FIG. 2B) of the tabletop 201. The first slide member 210 is configured to move in a translational direction that is perpendicular to the shoulder line 207 (e.g., along the longitudinal direction 206) relative to the head end 205 of the tabletop 201. The lower-torso assembly 202 also includes a second slide member 220 that is coupled to a slot 211 of the first slide member 210. The second slide member 220 is configured to move in the translational direction that is perpendicular to the shoulder line 207 (e.g., along the longitudinal direction 206) relative to the head end 205 of the tabletop 201.

The lower-torso assembly 202 also includes a link member 230 that is coupled to the first slide member 210 and a second slide member 220. The link member 230 includes one or more rigid links. The link member 230 may be configured in a flat tabletop configuration, a knee bolster configuration, or a bolster seat configuration. The link member may also be positioned selected position configured to be in an intermediate configuration between the flat tabletop configuration and the bolster seat configuration. By moving the first slide member 210 and a second slide member 220 relative to one another, the link member 230 converts between the flat tabletop configuration and the bolster seat configuration. In one embodiment, the link member 230 includes in the upper section 231 and the lower section 232. The top surfaces of the upper and lower sections 231 and 232 are configured to be flat with respect to a top surface of the tabletop 201 in a first configuration, and the top surface of the lower section 232 is configured to be at an angle with respect to the top surface of the tabletop and a second configuration. In one embodiment, the first configuration is a flat tabletop configuration, and a second configuration is a bolster seat or a knee bolster configuration.

In one embodiment, the link member 230 includes two rigid links, a first rigid link in the upper section 231, and a second rigid link in the lower sections 232. The first rigid link may be a seat pan, and the second rigid link may be a lower-leg support member coupled to each other by a hinge. With in this embodiment when the first locking mechanism 240 is disengaged, and the first slide member 210 and a second slide member 220 are moved closer together, the upper section 231 is moved from the flat position to be at an angled position with respect to the top surface of the tabletop 201. The relative positions of the first and second slide members 210 and 220 may be adjusted to change the angle of the upper and lower sections 231 and 233 of the link member 230. In one embodiment, the upper section 231 is positioned to have an angle of approximately 120 degrees between the top surface of the upper section 231 and the top surface of the tabletop 201. In another embodiment, the upper section 231 is positioned to have an angle of approximately 135 degrees between the top surface of the upper section 231 and the top surface of the tabletop 201. Alternatively, other angles may be used.

The lower-torso assembly 202 also includes a first locking mechanism 240 that is coupled to the first slide member 210 and the tabletop 201. When the first locking mechanism 240 is disengaged from the tabletop 201, the first slide member 210 is configured to slide along the slot 208 of the tabletop 201 along the longitudinal direction 206 relative to the shoulder line of the tabletop 201. When the first locking mechanism 240 is engaged, the first slide member 210 is prevented from sliding along the slot 208 of the tabletop 201. When the first locking mechanism 240 is disengaged, the entire lower-torso assembly 210 is configured to move with the first slide member 210 in the longitudinal direction 206. In one embodiment, the first locking mechanism 240 is a pin. The pin may be a spring pin or other locking mechanisms known by those of ordinary skill in the art. In another embodiment, the locking mechanism includes a lever and two pins, one pin disposed on each side of the lower-torso assembly. The lever is disposed on one side of the lower-torso assembly, and when activated, activates (e.g., engages or disengages) both pins. Alternatively, the two pins on the two sides of the lower-torso assembly may be remotely activated by other mechanisms known by those of ordinary skill in the art other than a lever. In one embodiment, the first locking mechanism 240 is a seat motion handle that is configured to allow the lower-torso assembly to move along the longitudinal direction 206 when disengaged from the tabletop 201.

The lower-torso assembly 202 also includes a second locking mechanism 250 that is coupled to the second slide member 220 and the first slide member 210. When the second locking mechanism 250 is disengaged from the first slide member, the second slide member 220 is configured to slide along the slot 211 of the first slide member 210 along the longitudinal direction 206 relative to the shoulder line of the tabletop 201. When the second locking mechanism 250 is engaged, the second slide member 220 is prevented from sliding along the slot 211 of the first slide member 210. Unlike the first locking mechanism 240, when the second locking mechanism 250 is disengaged, only the first and second slide members 210 and 220 are configured to move relative to one another. The movement of the first and second slide members 210 and 220 relative to each other converts the lower-torso assembly 202 between configurations, such as between the flat tabletop configuration, in which the lower-torso assembly 202 is flat relative to the tabletop 201, and the bolster seat configuration, in which the lower-torso assembly 202 is not flat relative to the tabletop 201. The bolster seat configuration may provide a seat for the patient for purposes of loading the patient onto the tabletop 201, or may provide a knee bolster for the patient when the patient is laying flat on the tabletop 201. The knee bolster may provide, for example, may allow the patient to be more comfortable during treatment while laying flat on the tabletop, allowing the patient to be on the tabletop for a longer period of time. Alternatively, other intermediate configurations may be used for other purposes. In one embodiment, the second locking mechanism 250 is a pin. The pin may be a spring pin or other locking mechanisms known by those of ordinary skill in the art. In one embodiment, the second locking mechanism 250 is a seat creation handle that is configured to allow the lower-torso assembly 202 to convert between a bolster seat on the tabletop and a flat tabletop when disengaged from the first slide member 210.

The slide member 210, the second slide member 220, the link member 230 of the lower-torso assembly 202 are all disposed outside the radiolucent region 204. In one embodiment, the components of the lower-torso assembly 202 are made of metal, and substantially of the metal of the lower-torso assembly 202 remains outside of the radiolucent region of the tabletop. In another embodiment, substantially all of the metal of the lower-torso assembly 202 remains outside of the imaging zone, as described herein. In one embodiment, the radiolucent region of the tabletop is substantially from the head end 205 to substantially the first hinge of the first slide member 210 of the lower-torso assembly 202. In one embodiment, the radiolucent region is substantially from the head end 205 to substantially the seat pan 254. In one embodiment, when the link member 230 is in the bolster seat configuration, a portion of the link member 230 may extend into the radiolucent region 204 of the tabletop 201 for shorter patients, such as the one percentile female (e.g., 58.1 inches). However, in these cases, the imaging zone, which extends from the lowest point of the rear pelvic area of the patient when the patient is in a seat position, is still free from obstructions by the lower-torso assembly during imaging. For example, a seat cushion may be disposed on the seat pan of the link member, which not only provides comfort to the patient during treatment, but positions the imaging zone entirely above the portion of the link member 230 that extends into the radiolucent region 204 of the tabletop 201. The imaging zone is the area of interest of the patient of which x-ray images are taken. Using the embodiments described herein, the imaging zone is free from imaging obstructions by the lower-torso assembly 202 regardless the height of the patient.

Figure 2B:
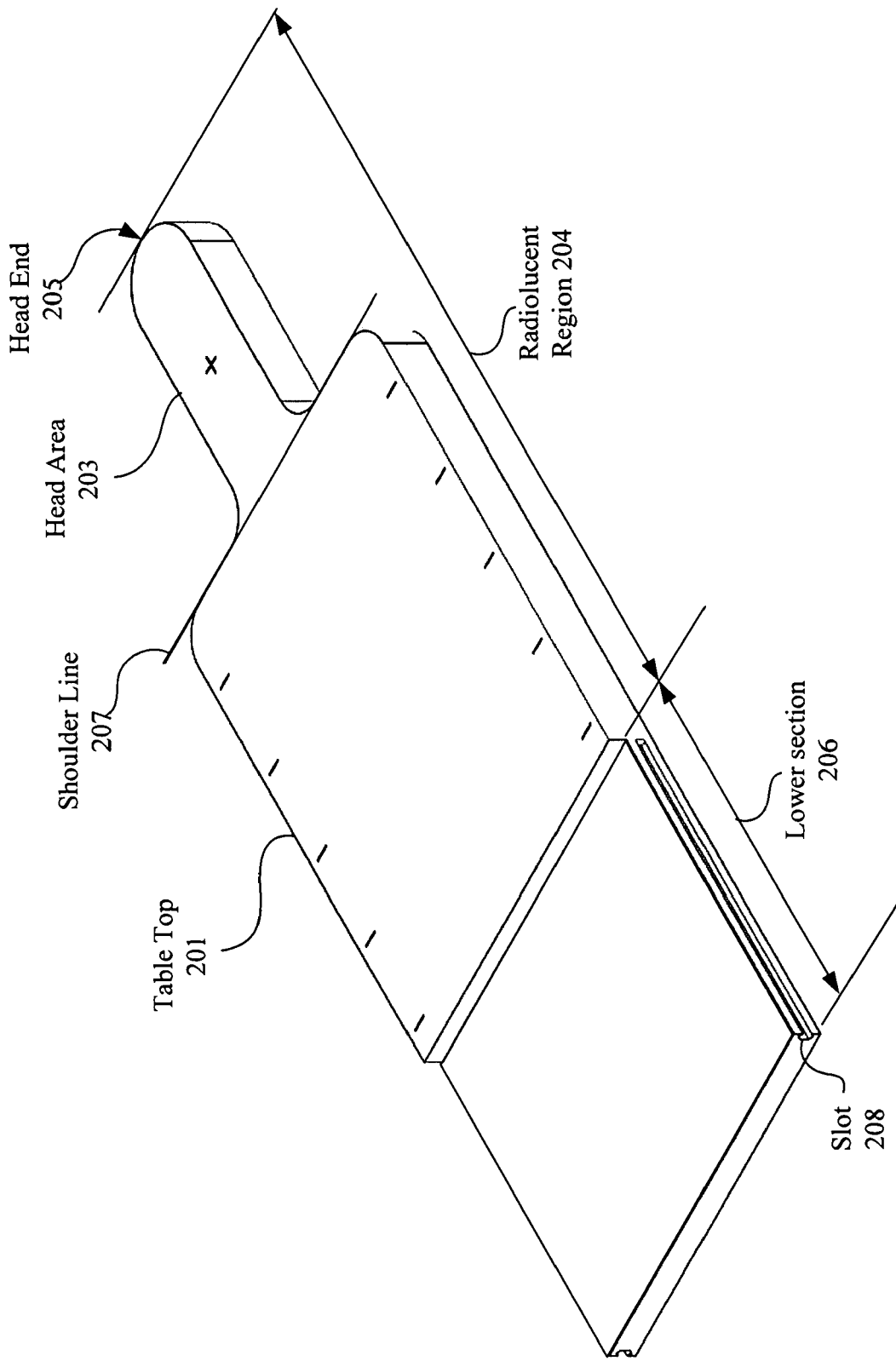
FIG. 2B illustrates a perspective view of one embodiment of the tabletop of the treatment couch of FIG. 2A.
Figure 2C:
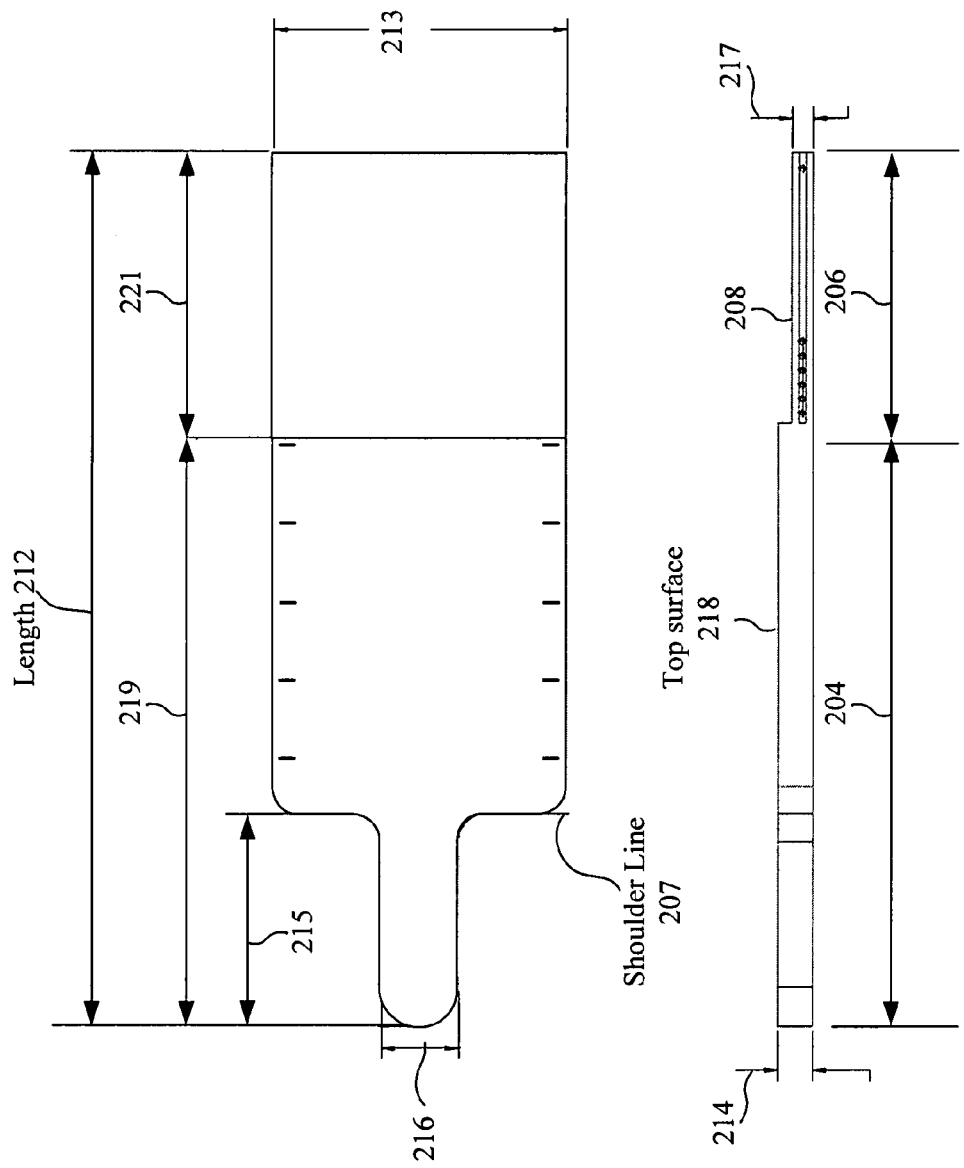
FIG. 2C illustrates a top view and a side view of the tabletop of FIG. 2B.

FIG. 2C illustrates a top view and a side view of the tabletop 201 of FIG. 2B. In one exemplary embodiment, the tabletop 201 may have a length 212 substantially in a range between 58 and 63 inches a width 213 substantially in a range between 20 and 26 inches, and a height 214 substantially in a range between 1.75 and 3 inches. In another embodiment, the length 212 is approximately 61.6 inches. In another embodiment, the width 213 is approximately 20.866 inches. It should be noted that the lower-torso assembly may be wider than the actual dimensions of the width 213 of the tabletop 213. In another embodiment, the height 214 is approximately 2.5 inches. The head area 203 may also have a length 215 substantially in a range between 12 and 17 inches and a width 216 substantially in a range of 5 and 8 inches. In another embodiment, the length 215 is approximately 15 inches. In another embodiment, approximately three inches of the length 215 are used for equipment attachment, such as a mounting device, which used to secure a mask to the patient 904. The mask may be used to secure the patient to the treatment couch 200 to limit the mobility of the patient 904 during treatment. In another embodiment, the width 216 is approximately 5.5 inches. In one embodiment, the width 216 of the head area 203 may be less than the width 213 of the tabletop 201 (as illustrated in FIG. 2C). Alternatively, the width 216 of the head area 203 may be substantially equal to the width 213 of the tabletop 201. In one embodiment, the lower section 206 of the tabletop 201 has a height 217 that is less than the height of the height 214 of the tabletop 201. The difference in height between height 214 and 217 may be equal to the height of the lower-torso assembly 202 when in the flat tabletop configuration so that the top surface of the lower-torso assembly 202 is substantially flush with the top surface 218 of the tabletop 201. Alternatively, the height 217 of the lower section 206 is substantially equal to the height 214 of the tabletop 201. In one embodiment, the radiolucent region has a length 219 that is substantially in a range between 40 and 45 inches. In another embodiment, the length 219 is approximately 42.6 inches. In one embodiment, the lower section 206 has a length that is substantially in a range between 18 and 22 inches. In another embodiment, the length of the lower section 206 is approximately 19 inches. Alternatively, other dimensions for the length 212, width 213, height 214, length 215, width 216, height 217, length 219, and length 221 may be used.

Figure 2D:
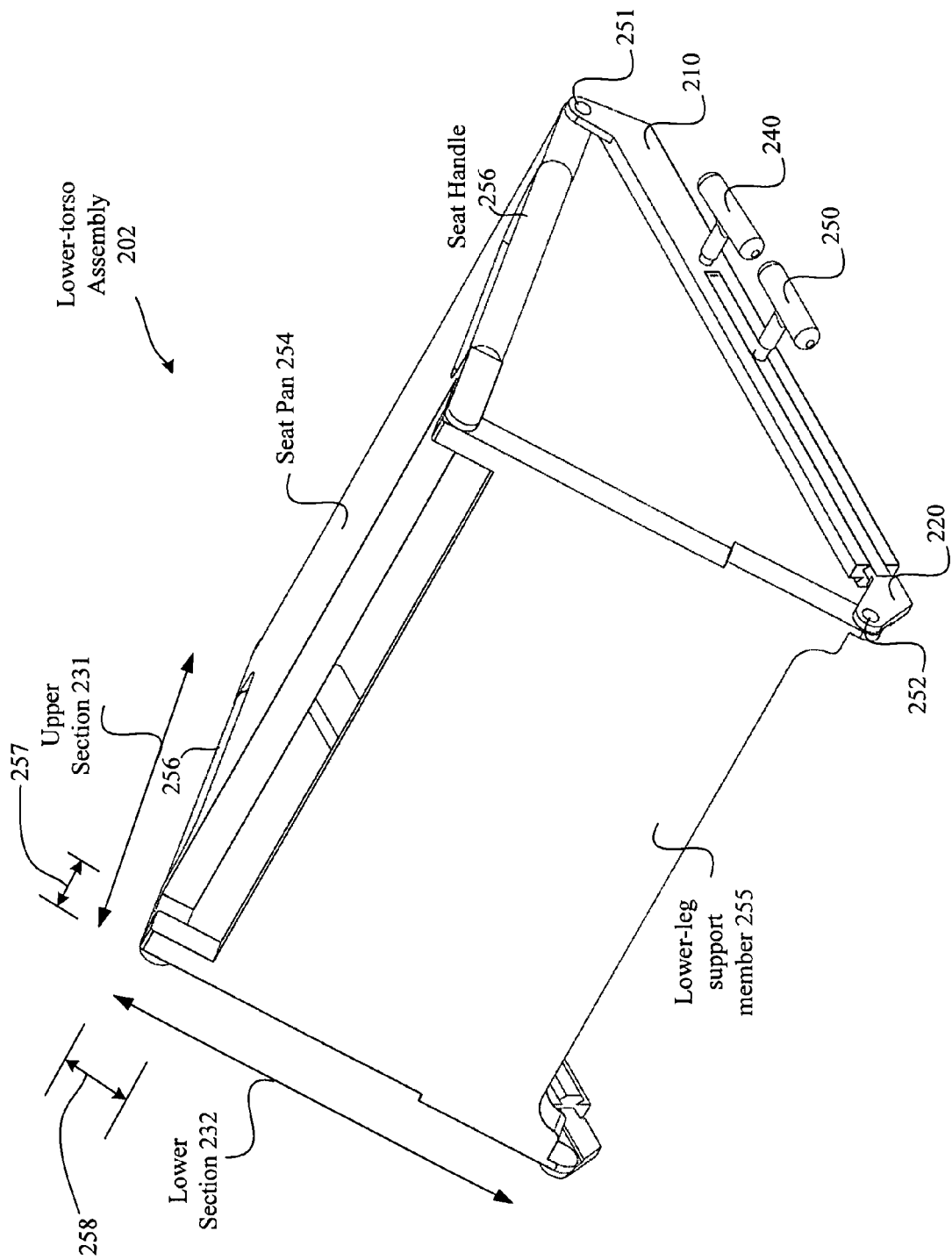
FIG. 2D illustrates a perspective view of one embodiment of the lower-torso assembly of the treatment couch of FIG. 2A.

FIG. 2D illustrates a perspective view of one embodiment of a lower-torso assembly 202 of the treatment couch of FIG. 2A. The lower-torso assembly 202 of FIG. 2D operates in a similar manner as the lower-torso assembly described above with respect to FIG. 2A. The lower-torso assembly 202 of FIG. 2D includes an upper-seat bracket 210 as the first slide member, a lower-seat bracket 220 as the second slide member. The lower-torso assembly 202 also includes a link member 230 having two rigid links. In this embodiment, a first rigid link in the upper section 231 is a seat pan 254 coupled to the upper-seat bracket 210 by a first hinge 251, and a second rigid link in the lower section 232 is a lower-leg support 255 coupled to the lower-seat bracket 220 by a second hinge 252. The seat pan 254 and the lower-leg support member 255 are coupled together by a third hinge 253 (not shown in FIG. 2D). The lower-torso assembly 202 also includes seat motion handle 240 (e.g., first locking mechanism) and seat creation handle 250 (e.g., second locking mechanism).

Figure 2E:
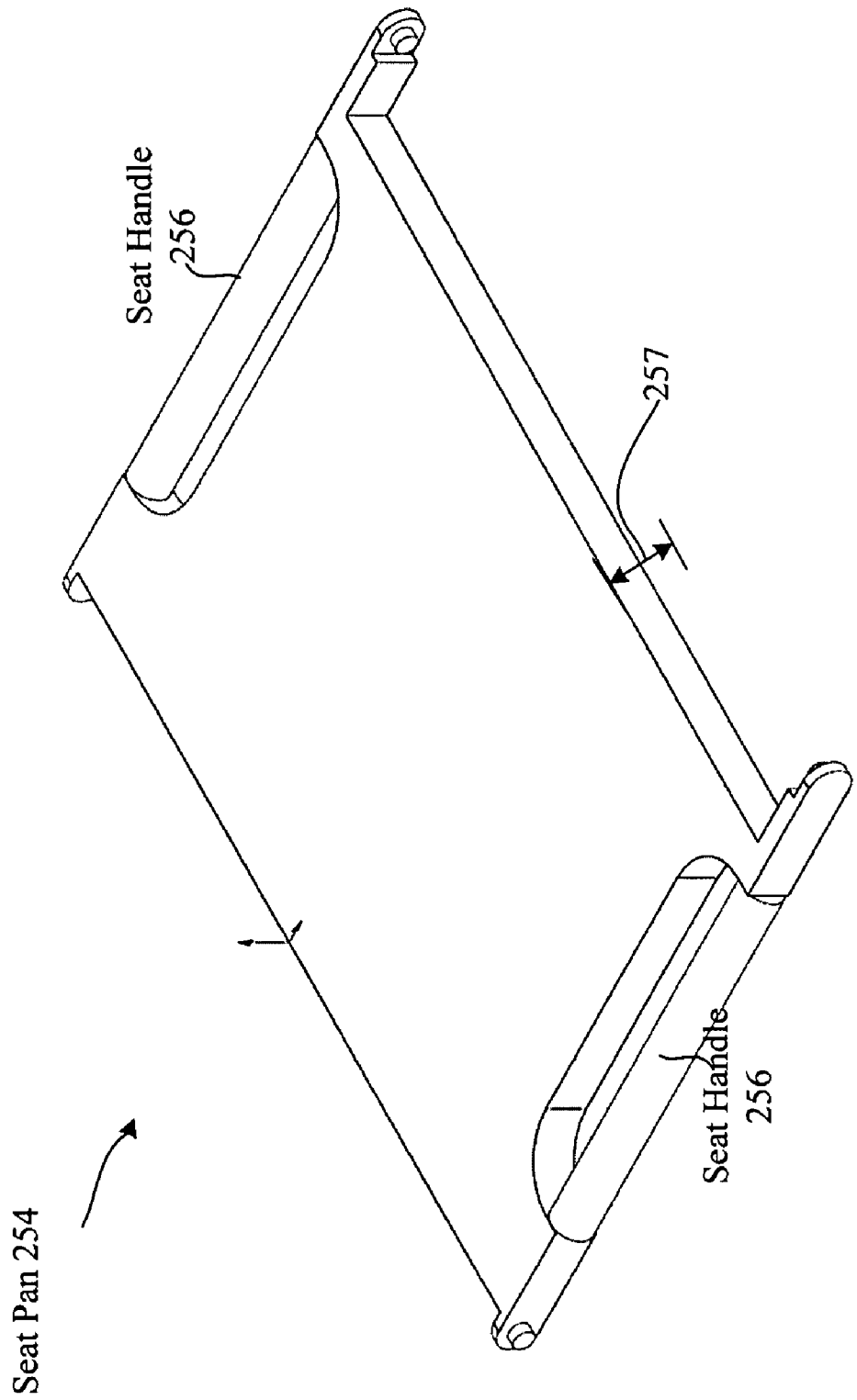
FIG. 2E illustrates one embodiment of a seat pan having two handles.

In one embodiment, the seat pan 254 includes one or more patient handles 256 (also illustrated in FIG. 2E). In another embodiment, the seat pan 254 includes an area 257 that is cut out or cut back (also illustrated in FIG. 2E). When the lower-torso assembly 202 is in the bolster seat configuration, the cut out area 257 allows the lower-torso assembly from having an edge or a point that is in direct contact with the back of the patient's knee, which may be uncomfortable for the patient during treatment. In another embodiment, the lower-leg support member 255 includes a cut out area 258. The cut out area 258 may also allow the lower-torso assembly 202 from having an edge or point that is in direct contact with the back of the patient's knee. In one embodiment, both the seat pan 254 and the lower-leg support member 255 include a cut out area. Alternatively, only one of the seat pan 254 and the lower-leg support member 255 includes a cut out area.

The upper-seat bracket 210, the lower-seat bracket 220, the link member 230 of the lower-torso assembly 202 are all disposed outside the radiolucent region 204. In one embodiment, the components of the lower-torso assembly 202 are made of metal, and substantially of the metal of the lower-torso assembly 202 remains outside of the radiolucent region of the tabletop. In another embodiment, substantially all of the metal of the lower-torso assembly 202 remains outside of the imaging zone, as described herein. In one embodiment, the radiolucent region of the tabletop is substantially from the head end 205 to substantially the first hinge of the upper-seat bracket 210 of the lower-torso assembly 202. In one embodiment, the radiolucent region is substantially from the head end 205 to substantially the seat pan 254. In one embodiment, when the link member 230 is in the bolster seat configuration, a portion of the link member 230 may extend into the radiolucent region 204 of the tabletop 201 for shorter patients, such as the one percentile female (e.g., 58.1 inches). However, in these cases, the imaging zone, which extends from the lowest point of the rear pelvic area of the patient when the patient is in a seat position, is still free from obstructions by the lower-torso assembly during imaging. For example, a seat cushion may be disposed on the seat pan of the link member, which not only provides comfort to the patient during treatment, but positions the imaging zone entirely above the portion of the link member 230 that extends into the radiolucent region 204 of the tabletop 201. As described above, the imaging zone is the area of interest of the patient of which x-ray images are taken. Using the embodiments described herein, the imaging zone is free from imaging obstructions by the lower-torso assembly 202 regardless the height of the patient.

Figure 2F:
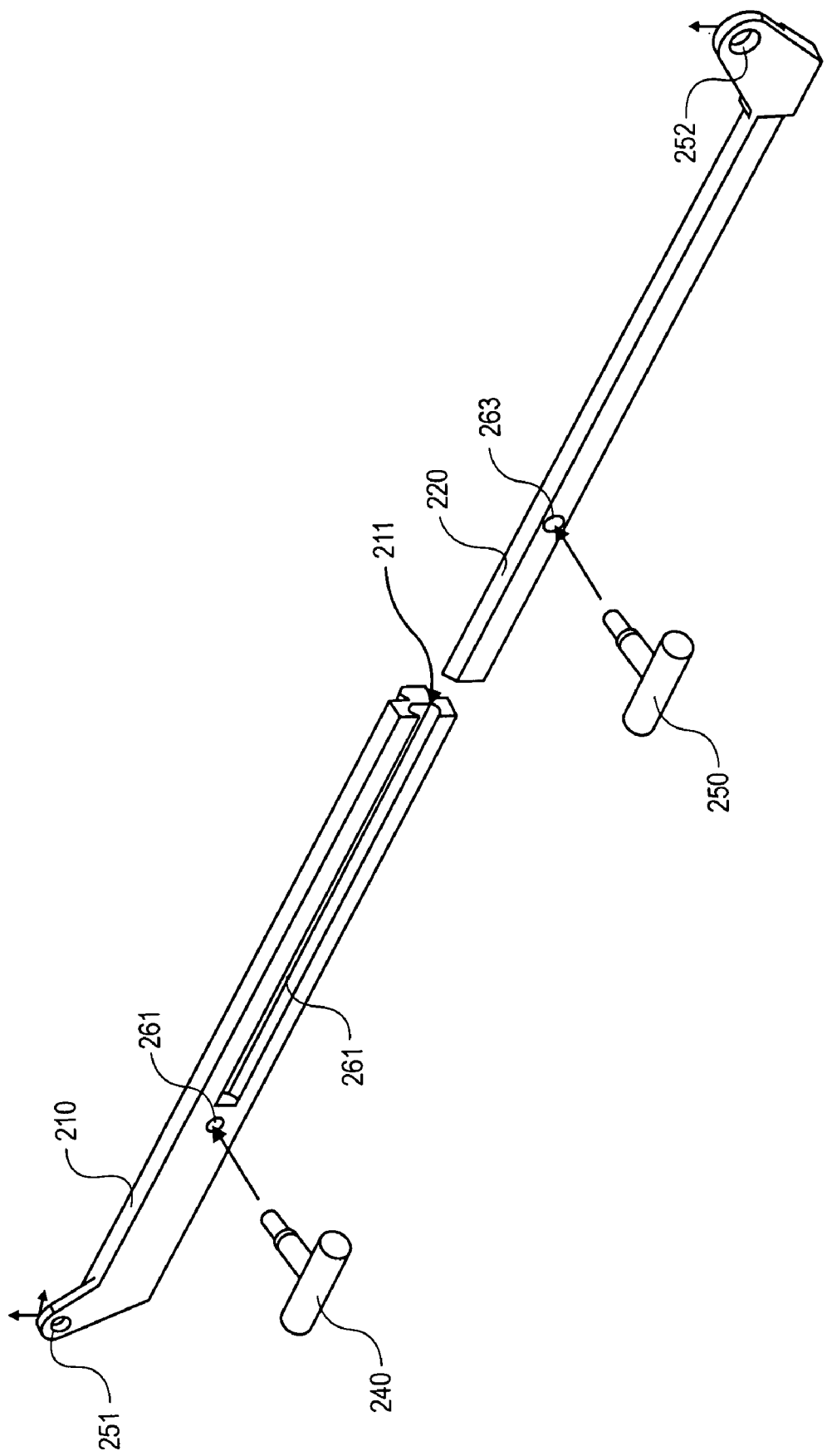
FIG. 2F illustrates a perspective view of an upper-seat bracket and a lower-seat bracket of the lower-torso assembly of FIG. 2D.

FIG. 2F illustrates a perspective view of the upper-seat bracket 210 and a lower-seat bracket 220 of the lower-torso assembly 202 of FIG. 2D. The upper-seat bracket 210 includes slot 211 in which the lower-seat bracket 220 slides in the longitudinal direction 206. The upper-seat bracket 210 is configured to receive the first locking mechanism 240 in the hole 261. The first locking mechanism 240 is configured to lock the lower-torso assembly 202 to the tabletop 201 when engaged. The first locking mechanism 240 is configured to allow the upper-seat bracket 210 to slide in the slot 208 of the tabletop 201 when disengaged. The upper-seat bracket 210 also includes one or more holes, such as hole 262, to receive the second locking mechanism 250. The lower-seat bracket 220 includes a hole 263 to receive a second locking mechanism 250. The second locking mechanism 250 is configured to lock the lower-seat bracket 222 the upper-seat bracket 210 when engaged. When the second locking mechanism 250 is engaged, the relative movement between the upper-seat bracket 210 and the lower-seat bracket 220 is prevented, however, the upper-seat bracket 210 and lower-seat bracket 220 may be able to move when the first locking mechanism 240 is disengaged (e.g., by the upper-seat bracket 210 sliding along the slot 208 of the tabletop 201. The second locking mechanism 250 is configured to allow the lower-seat bracket 220 to slide in the slot 211 of the upper-seat bracket 210 when disengaged. The second locking mechanism 250 is also configured to prevent the lower-torso assembly 202 from converting between the flat tabletop configuration and the bolster seat configuration when engaged. The first and second locking mechanisms 240 and 250 have been illustrated as handles in FIG. 2F. The first handle 240 may be a seat motion handle that allows the lower-torso assembly 202 to be adjusted relative to the head end 205 of the tabletop 201, such as to adjust the position of the patient so that the patient's shoulders are substantially aligned at the shoulder line 207. Alternatively, the first and second locking mechanisms 240 and 250 may be other type of locking mechanisms, such as pins, spring pins, or the like.

In another embodiment, the lower-torso assembly 202 includes a foot extension coupled to the lower-leg support member 255. The foot extension is configured to provide support beyond the surface area of the lower-leg support member 255, for example, for patient's having legs that extend beyond the lower-leg support member 255. This may be useful in supporting the patient's ankles, providing additional comfort to the patient during treatment. In one embodiment, the foot extension slides into a slot in the lower-leg support member 255 when not being used, and slides out from the lower-leg support member 255 away from the head-end 205 of the tabletop 201. Alternatively, the foot extension is coupled of lower-leg support member 255 in other configurations, such as sliding under the lower-leg support member 255, or the like. The foot extension may be locked at various positions to support portions of the legs of differing lengths of patients beyond the lower-leg support member 255.

Figure 3A:
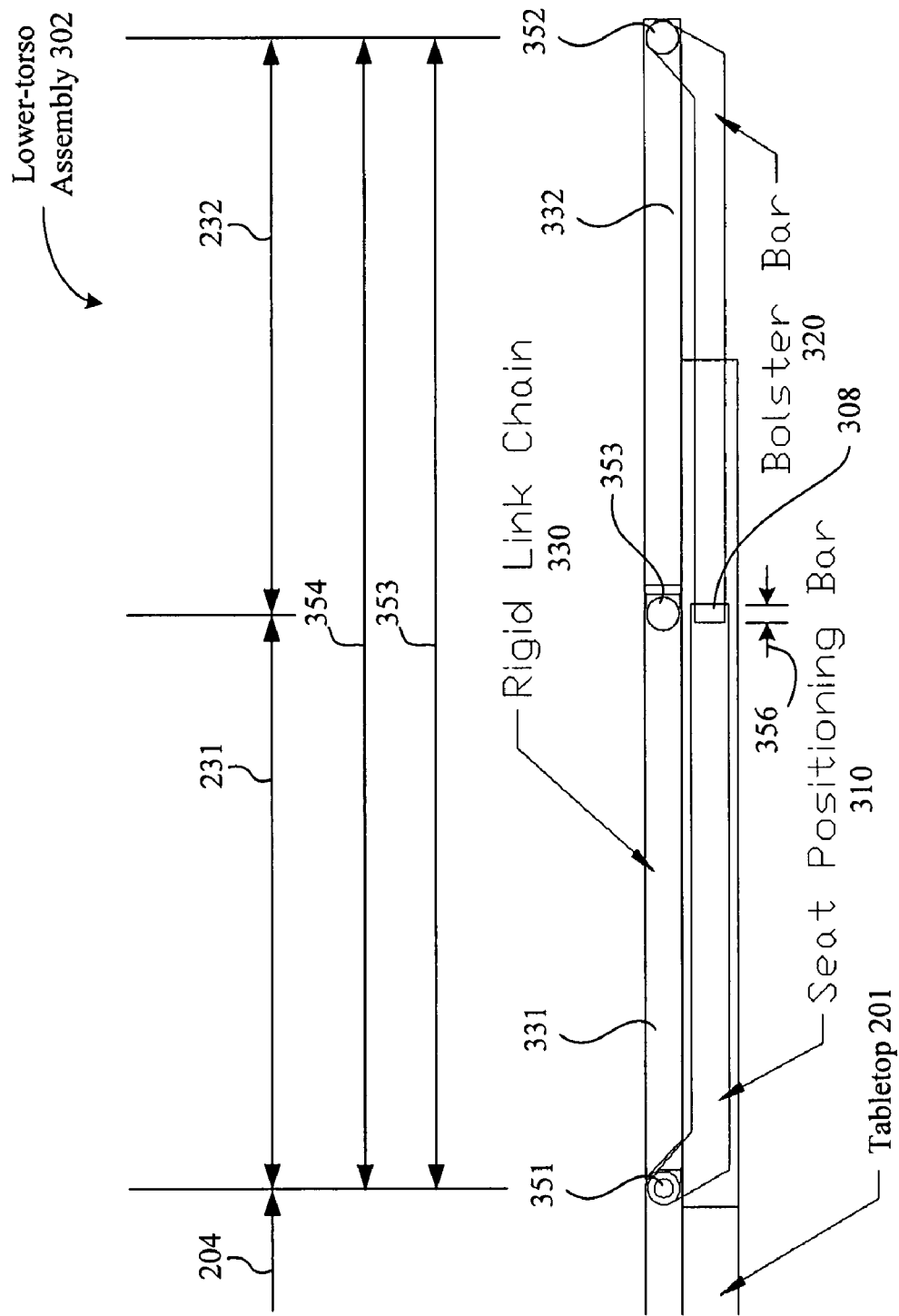
FIG. 3A illustrates a side view of one embodiment of a lower-torso assembly in a flat configuration.

FIGS. 3A and 2B illustrates side views of one embodiment of a lower-torso assembly 302 in a flat configuration and in a bolster seat configuration. Lower-torso assembly 302 includes a seat positioning bar 310 as the first slide member, a bolster bar 320 as the second slide member, and a rigid link chain 330 as the link member. The rigid link chain 330 includes two rigid links, the first rigid link 331 in the upper sections 231, and the second rigid link 332 in the lower sections 232. The first rigid link 331 is coupled to the seat positioning bar 310 by a first hinge 351. The second rigid link 332 is coupled to the bolster bar 320 by a second hinge 352. The first and second rigid links 331 and 332 are coupled together by a third hinge 353. The first and second rigid links 331 and 332 are configured to rotate relative to each other while being fixed in the other direction at the first and second hinges 351 and 352, respectively. The rotation of the first and second rigid links 331 and 332 may be restricted. Alternatively, the rotation of the first and second rigid links 331 and 332 are not restricted. The seat positioning bar 310 is coupled to the tabletop 201 by a slot, such as slot 208 described above.

The bolster bar 320 is coupled to the seat positioning bar 310 by a slot 308 in the seat positioning bar 310. As the bolster bar 320 is moved towards the head end 205 of the tabletop 201, the bolster bar 320 slides in the slot of the seat positioning bar 310, causing the rigid link chain to form a bolster seat having two sections, a seat pan in the upper section 231, and a lower-leg support member in the lower section 232. Similarly, as the seat positioning bar 310 is moved towards or away from the head end 205 of the tabletop 201, the seat positioning bar 310 slides in the slot of the tabletop. The seat positioning bar 310 is configured to move the entire lower-torso assembly 302 when the seat positioning bar 310 slides along the slot of the tabletop.

Figure 3B:
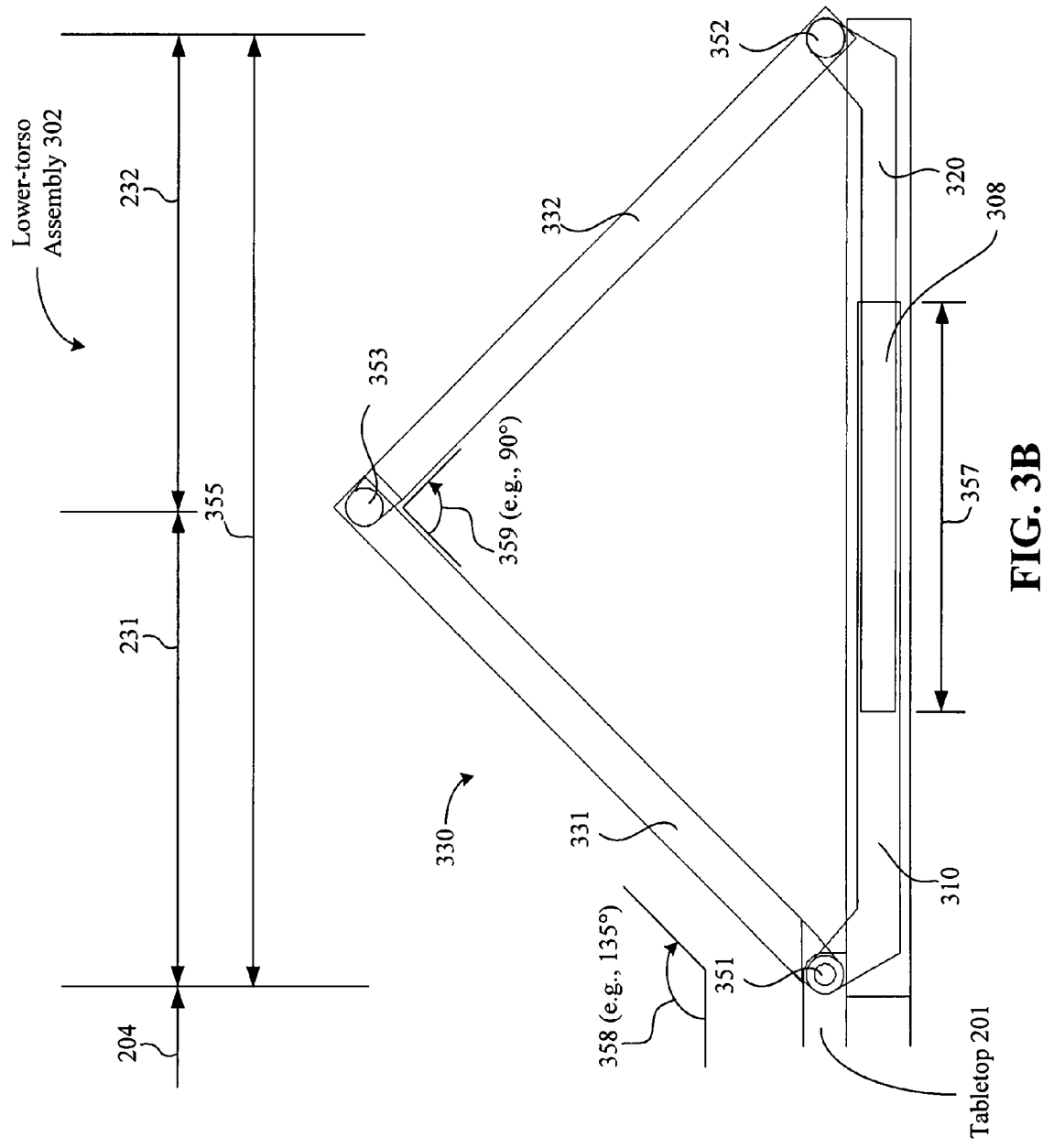
FIG. 3B illustrates a side view of the lower-torso assembly of FIG. 3A in a bolster seat configuration.

A first locking mechanism may be used to lock the relative positions of the seat positioning bar 310 and the bolster bar 320. The relative positions may configure the lower-torso assembly 302 to be in various configurations, such as a flat configuration, a seat configuration, or an intermediate configuration between the flat and seat configurations. For example, holes may be disposed in the slot of the seat positioning bar 310 to receive the first locking mechanism that is coupled to the bolster bar 320. Alternatively, other configurations for locking the seat positioning bar 310 and the bolster bar 320 may be used. FIG. 3A illustrates one embodiment of the flat configuration of the lower-torso assembly 302. FIG. 3B illustrates one embodiment of the seat configuration of the lower-torso assembly 302. Alternatively, the lower-torso assembly 302 may be configured in an intermediate configuration.

When in the flat configuration, the seat positioning bar 310 and the bolster bar 320 are locked so that the hinge centers of the first and second hinges 351 and 352 are at a distance that is substantially equal to the length 354 of the rigid link chain 330, as illustrated in FIG. 3A. When in the seat configuration, the seat positioning bar 310 and the bolster bar 320 are locked so that they hinge centers of the first and second hinges 351 and 352 are at a distance 355 that is less than the length 354 of the rigid link chain 333, as illustrated in FIG. 3B. In one embodiment, the distance 356 the seat positioning bar 310 overlaps the bolster bar 320 when in the flat configuration is less than the distance 357 the seat positioning bar 310 overlaps the bolster bar 320 when in the seat configuration. The amount the seat bar 310 overlaps the bolster bar 320 increases as the hinge center of the second hinge 352 is moved towards the hinge center of the first hinge 351, and the amount the seat positioning bar 310 overlaps the bolster bar 320 decreases as the hinge center of the second hinge 352 is moved away from the hinge center of the first hinge 351. The first locking mechanism is configured to allow the seat positioning bar 310 and the bolster bar 320 to slide the hinge centers of the first and second hinges 351 and 352 relative to one another when the first locking mechanism is disengaged from between the seat positioning bar 310 and the bolster bar 320. The first locking mechanism is also configured to prevent the seat positioning bar 310 and the bolster bar 320 to slide the hinge centers of the first and second hinges 351 and 352 relative to one another when the first locking mechanism is engaged between the seat positioning bar 310 and the bolster bar 320. As described above, the locking mechanism may be a pin, a spring pin, or other types of locking mechanisms known by those of ordinary skill in the art.

A second locking mechanism may also be used to lock the relative positions of the lower-torso assembly 302 with respect to the tabletop 201 (e.g., the position of the seat positioning bar 310 within the slot of the tabletop 201. The lower-torso assembly 302 moves along the longitudinal direction 206 when the second locking mechanism is disengaged from the tabletop 201. The relative positions of the lower-torso assembly 302 may be configured to adjust the length of the distance between the top of the lower-torso assembly 302 and the shoulder line 207. The tabletop 201 includes multiple height positions at which the second locking mechanism locks the seat positioning bar to the tabletop 201. For example, holes may be disposed in the slot of the tabletop 201 to receive the second locking mechanism that is coupled to the seat positioning bar 310. Alternatively, other configurations for locking the seat positioning bar 310 and the tabletop 210 may be used. The lower-torso assembly 302 may be adjusted to accommodate differing heights of patients in aligning shoulders to the shoulder line 207. It should be noted that the patient load is carried in shear by the locking mechanism (e.g., locking mechanism 240 of FIG. 2A) on the seat positioning bar (e.g., first slide member 210) and in moment by the boundaries of the slot (e.g., slot 208 of FIG. 2B) of the tabletop 201. In one embodiment, the various height positions includes a first height position that is configured to position a female having the one percentile female height to the shoulder line 207 of the tabletop 201, and a second height position that is configured to position a male having the 99th percentile male height to the shoulder line 207 of the tabletop 201. As described above, the locking mechanism may be a pin, a spring pin, or other types of locking mechanisms known by those of ordinary skill in the art.

In one embodiment, the seat positioning bar 310 and the bolster bar 320 are locked so that the first rigid link 331 is locked at an angle 358 of approximately 135 degrees from the top surface of the tabletop 201. In one embodiment, when the first rigid link 331 is locked at approximately 135 degrees, the second rigid link 332 is locked at an angle 359 of approximately 90 degrees with respect to the first rigid blank 331. Alternatively, the seat positioning bar 310 and a bolster bar 320 are locked so that the first rigid link 331 is locked at an angle of approximately 120 degrees from the top surface of the tabletop 201. Alternatively, other angles of the first rigid link 331 with respect to the tabletop 201, and of the second rigid link 332 with respect to the first rigid link 331 may be used.

In one embodiment, all the complements of the lower-torso assembly 302 remain outside the radiolucent region 204 of the tabletop 201, while the lower-torso assembly 302 is adjusted relative to the shoulder line 207 of the tabletop 201 to substantially align the patient's shoulders to the shoulder line 207.

It should be noted that although the embodiments described with respect to FIGS. 2A-2F, and FIGS. 3A and 3B include to rigid links for the link member 230 and the rigid link chain 330, the link member may include one or more rigid links. For example, the link member of FIG. 4 includes three rigid links of a rigid link chain.

Figure 4:
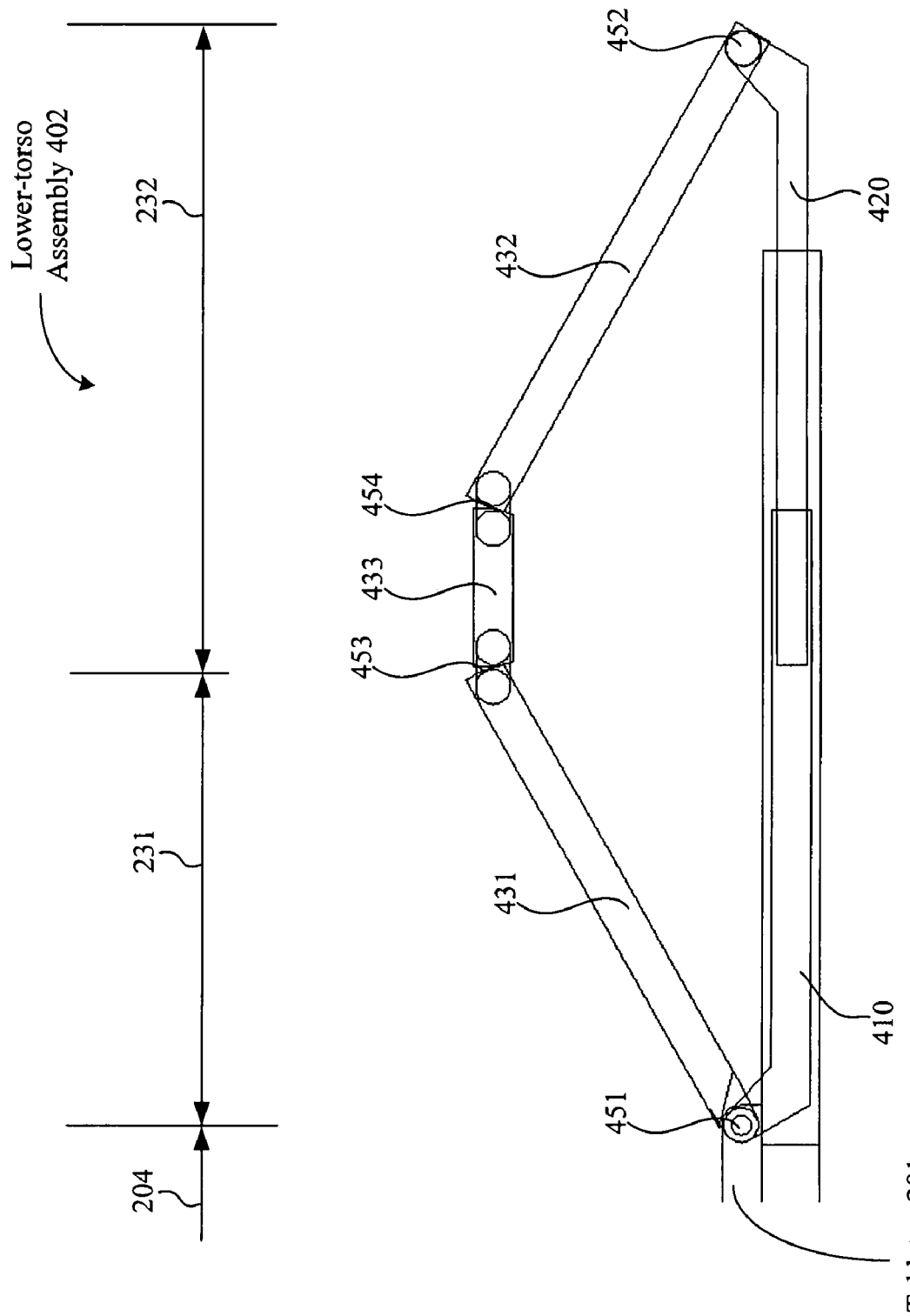
FIG. 4 illustrates a side view of another embodiment of a lower-torso assembly in a bolster seat configuration.

FIG. 4 illustrates a side view of another embodiment of a lower-torso assembly 402 in a bolster seat configuration. Lower-torso assembly 402 includes a seat positioning bar 310 as the first slide member, a bolster bar 320 as the second slide member, and a rigid link chain 430 as the link member. The lower-torso assembly 402 is similar to the lower-torso assembly 302, except the rigid link chain 430 includes three rigid links, the first rigid link 431 in the upper sections 231, and the second and third rigid link 432 and 433 in the lower sections 232. In another embodiment, the upper section 321 and lower section 232 may include a portion of each of the third rigid link 433. The first rigid link 431 is coupled to the seat positioning bar 310 by a first hinge 451. The second rigid link 432 is coupled to the bolster bar 320 by a second hinge 452. The third rigid link 433 is coupled to the first and second rigid links 431 and 431 by third and fourth hinges 453 and 454, respectively. The first, second, and third rigid links 431, 432, and 433 are configured to rotate relative to each other while the first and second rigid links are fixed in the other direction at the first and second hinges 451 and 452, respectively. The rotation of the first, second, and third rigid links 431, 423, and 433 may be restricted. Alternatively, the rotation of the first, second, and third rigid links 431, 423, and 433 are not restricted. As described above, as the bolster bar 320 is moved towards the head end 205 of the tabletop 201, the bolster bar 320 slides in the slot of the seat positioning bar 310, causing the rigid link chain to form a bolster seat having three rigid links, one rigid link forming a seat pan in the upper section 231, and the other two rigid links forming a lower-leg support member in the lower section 232 (as illustrated in FIG. 4). Similarly, as the seat positioning bar 310 is moved towards or away from the head end 205 of the tabletop 201, the seat positioning bar 310 slides in the slot of the tabletop. The seat positioning bar 310 is configured to move the entire lower-torso assembly 302 when the seat positioning bar 310 slides along the slot of the tabletop.

Figure 5:
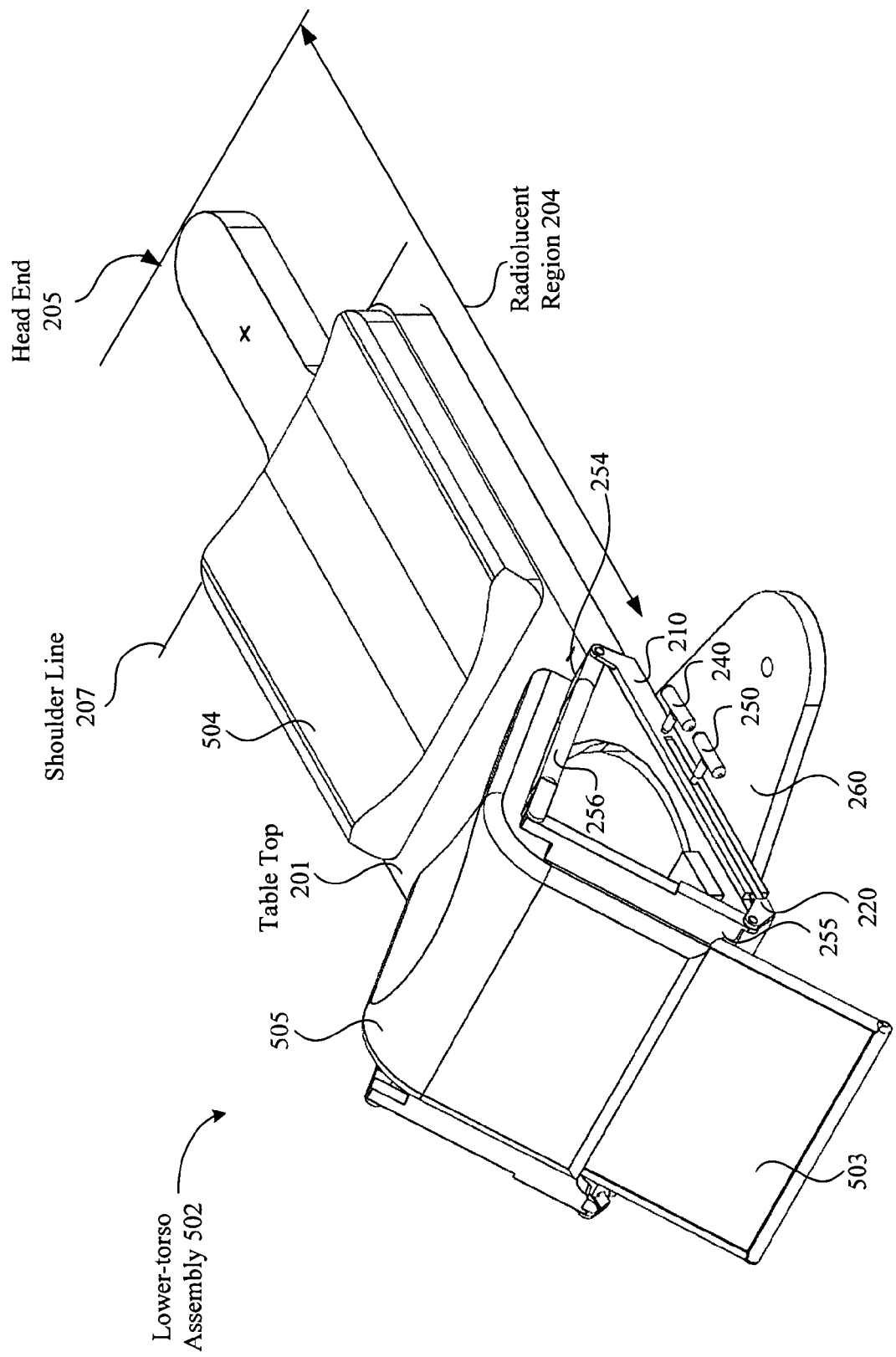
FIG. 5 illustrates a perspective view of another embodiment of treatment couch having a tabletop and a lower-torso assembly.

FIG. 5 illustrates a perspective view of another embodiment of treatment couch having a tabletop and a lower-torso assembly 502. Lower-torso assembly 502 is similar to the lower-torso assembly 202, except the lower-torso assembly 502 also includes a foot extension 503, a tabletop cushion 504, and a seat cushion 505. The foot extension 503 is coupled to the lower-leg support member 255. The foot extension 503 is configured to provide support beyond the surface area of the lower-leg support member 255, for example, for patient's having legs that extend beyond the lower-leg support member 255. This may be useful in supporting the patient's ankles, providing additional comfort to the patient during treatment. In one embodiment, the foot extension 503 slides into a slot in the lower-leg support member 255 when not being used, and slides out from the lower-leg support member 255 away from the head-end 205 of the tabletop 201. Alternatively, the foot extension 503 is coupled of lower-leg support member 255 in other configurations, such as sliding under the lower-leg support member 255, or the like. The foot extension 503 may be locked at various positions to support portions of the legs of differing lengths of patients beyond the lower-leg support member 255.

The tabletop cushion 504 and the seat cushion 505 may be added to the treatment couch to provide addition comfort to the patient during treatment. The tabletop cushion 504 is coupled to the top surface of the tabletop 201. In one embodiment, the tabletop cushion is a curved tabletop cushion, as illustrated in FIG. 5. Alternatively, the tabletop cushion may have other types of shapes, such as a straight, rounded, or the like. The top end of the tabletop cushion 504 may be positioned to be aligned at the shoulder line 207. Alternatively, the tabletop cushion 504 may be positioned to other points on the tabletop 201. In one embodiment, the length of the tabletop cushion 504 is approximately 22 inches. Alternatively, the length of the tabletop cushion 504 may be more or less than 22 inches. The bottom end of the tabletop cushion 504 may be disposed such that it does not obstruct the motion of lower-torso assembly 502. The tabletop cushion 504 may be disposed to the back of the patient regardless of the height of the patient, allowing a sufficient gap between the tabletop cushion 504 and the seat cushion 505 (or the lower-torso assembly 502).

The seat cushion 505 is coupled to the top surface of the link member 230 (e.g., top surfaces of the seat pan 254 and the top surface of the lower-leg support member 255). In one embodiment, the seat cushion 505 is a foldable cushion that folds over the lower-torso assembly 502 when in a bolster seat configuration. Alternatively, two seat cushions may be disposed on each section of the lower-leg assembly. The seat cushion 505 may be used to provide additional comfort to the patient while in either the bolster seat configuration or while in the flat tabletop configuration. In one embodiment, the top end of the seat cushion 505 has a thickness of approximately 1 inch above the top surface of the seat pan 254 when loaded with a patient, such as 180 pounds (lbs). Alternatively, the seat cushion 505 has other thicknesses. In another embodiment, additional cushions may be added to the lower-torso assembly 502 to provide additional comfort to the patient while disposed on the treatment couch, such as a wedge-shaped pad to go under the back of the patient's legs.

Figure 6:
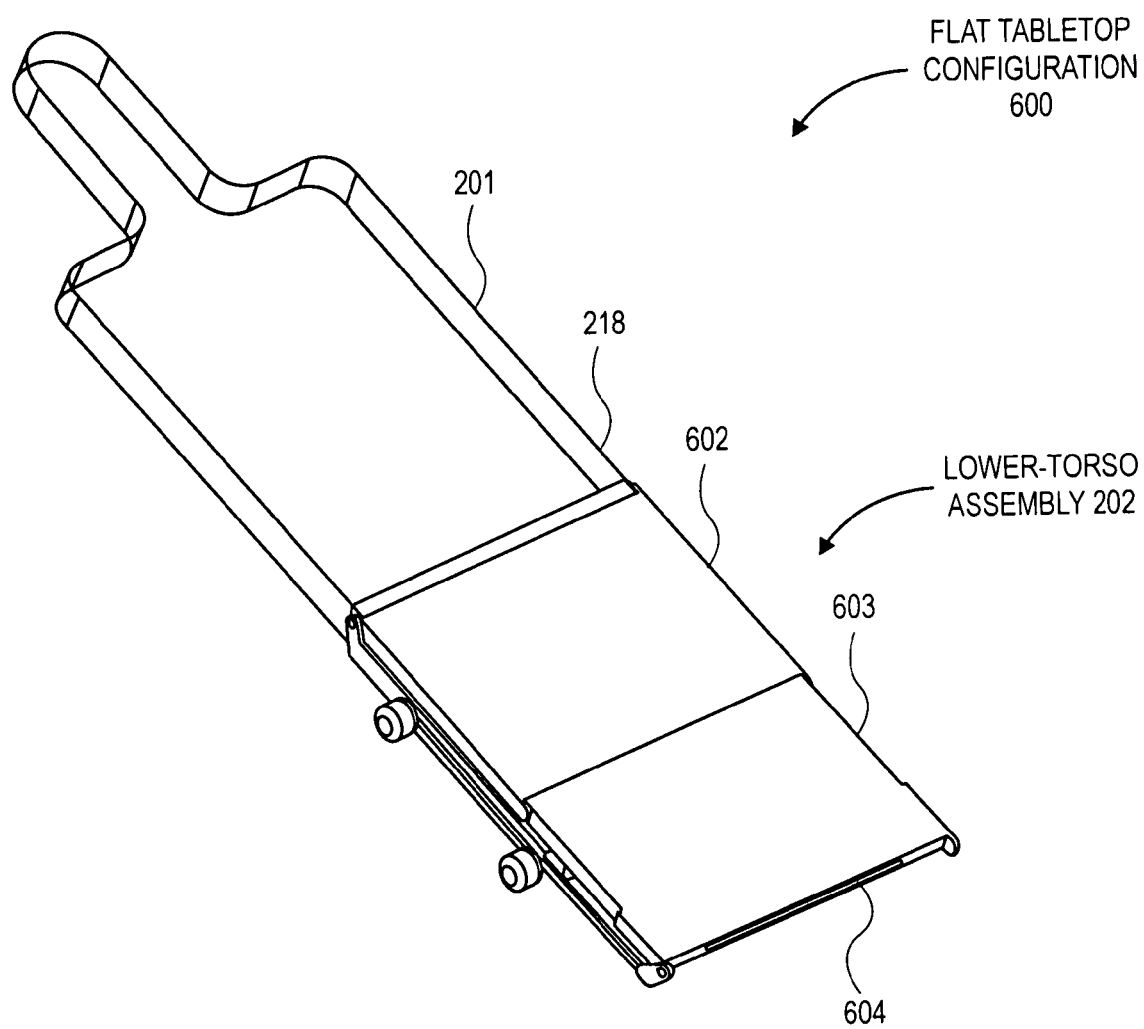
FIG. 6 illustrates an elevated view of one embodiment of a treatment couch having a tabletop and a lower-torso assembly in a flat configuration.

FIG. 6 illustrates an elevated view of one embodiment of a treatment couch having a tabletop 201 and a lower-torso assembly 202 in a flat configuration 600. In the flat configuration 600, the top surface 218 of the tabletop 201 is substantially flush with the top surfaces 602 and 603 of the lower-torso assembly. The top surface 602 of the upper section 231 and the top surface 603 of the lower section 232 are substantially flat with respect to a plane of the top surface of the tabletop 201. In one embodiment, the lower section of the lower-torso assembly 202 includes a slot 604 to receive the foot extension 503, as describe with respect to FIG. 5. Alternatively, the lower section includes another configuration for mounting the foot extension or a configuration that does not include a foot extension. In one embodiment, when the upper and lower sections of the lower-torso assembly 202 are substantially flat, the tabletop 201 and the lower-torso assembly 202 form a flat tabletop. In another embodiment, when the upper and lower sections of the lower-torso assembly 202 are not substantially flat, the tabletop 201 in the lower-torso assembly 202 form a bolster seat, or a knee bolster.

Figure 7:
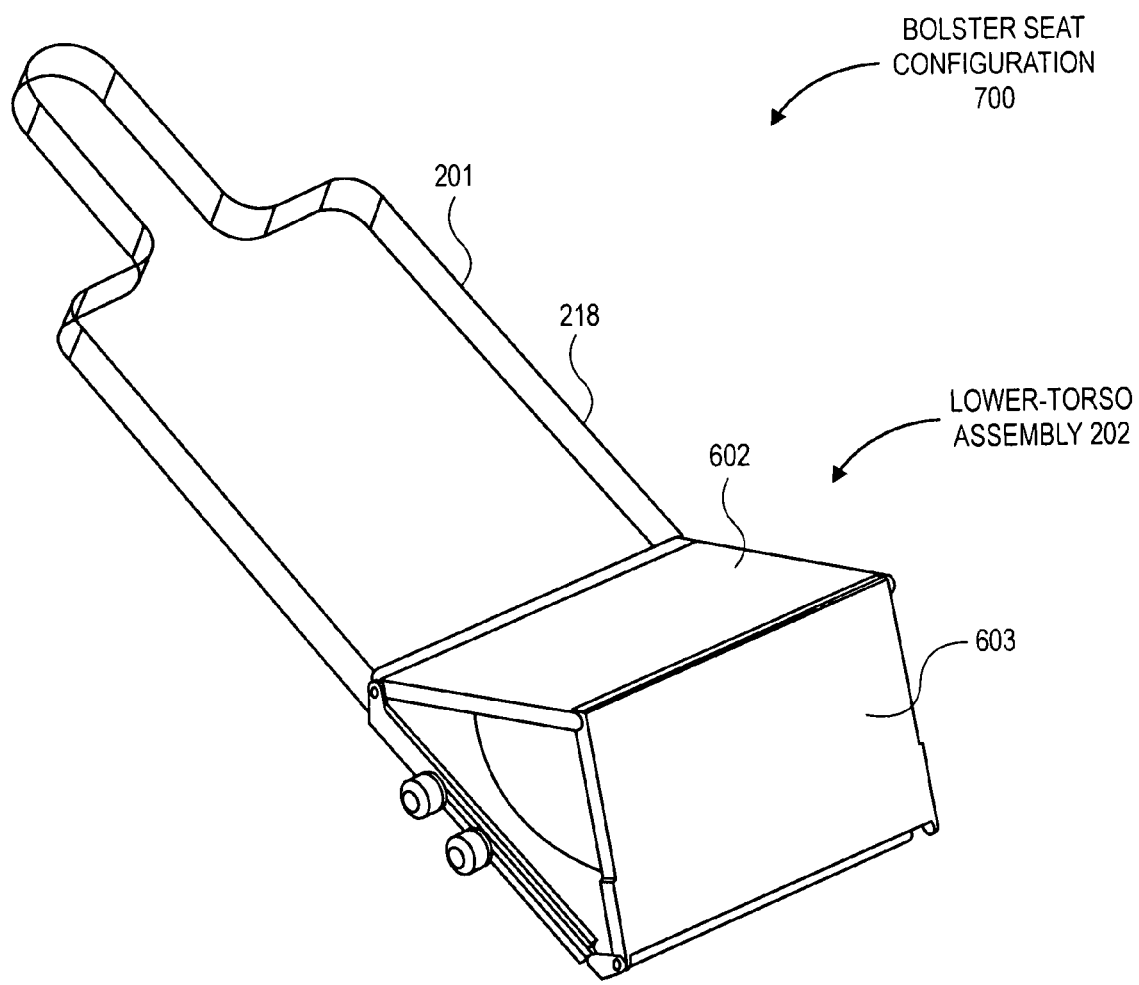
FIG. 7 illustrates an elevated view of the treatment couch of FIG. 6 in a bolster seat configuration.

FIG. 7 illustrates an elevated view of the treatment couch of FIG. 6 in a bolster seat configuration 700. In the bolster seat configuration 700, the top surface 218 of the tabletop 201 is not substantially flush with the top surfaces 602 and 603 of the lower-torso assembly. The top surface 602 of the upper section 231 is at an angle with respect to the plane of the top surface 218 of the tabletop 201. As the lower-torso assembly 202 converts from the flat configuration 600 to the bolster seat configuration 700 (or other intermediate configuration), the angle between the top surface 218 of the tabletop 201 and the top surface 602 of a lower-torso assembly 202 decrease from approximately 180 degrees in the flat configuration 600 to one or more angles less than 180 degrees in the bolster seat configuration 700 or an intermediate configuration; and likewise, increases from the one or more angles less than 180 degrees to approximately 180 degrees as the lower-torso assembly 202 converts from the bolster seat configuration 700 (or other intermediate configuration) to the flat configuration 600. In one embodiment, the angle between the top surface 218 of the tabletop 201 and the top surface 602 of a lower-torso assembly 202 is approximately 120 degrees. In another embodiment, the angle between the top surface 218 of the tabletop 201 and the top surface 602 of a lower-torso assembly 202 is approximately 135 degrees. Alternatively, other angles less than 180 degrees may be used.

Figure 8:
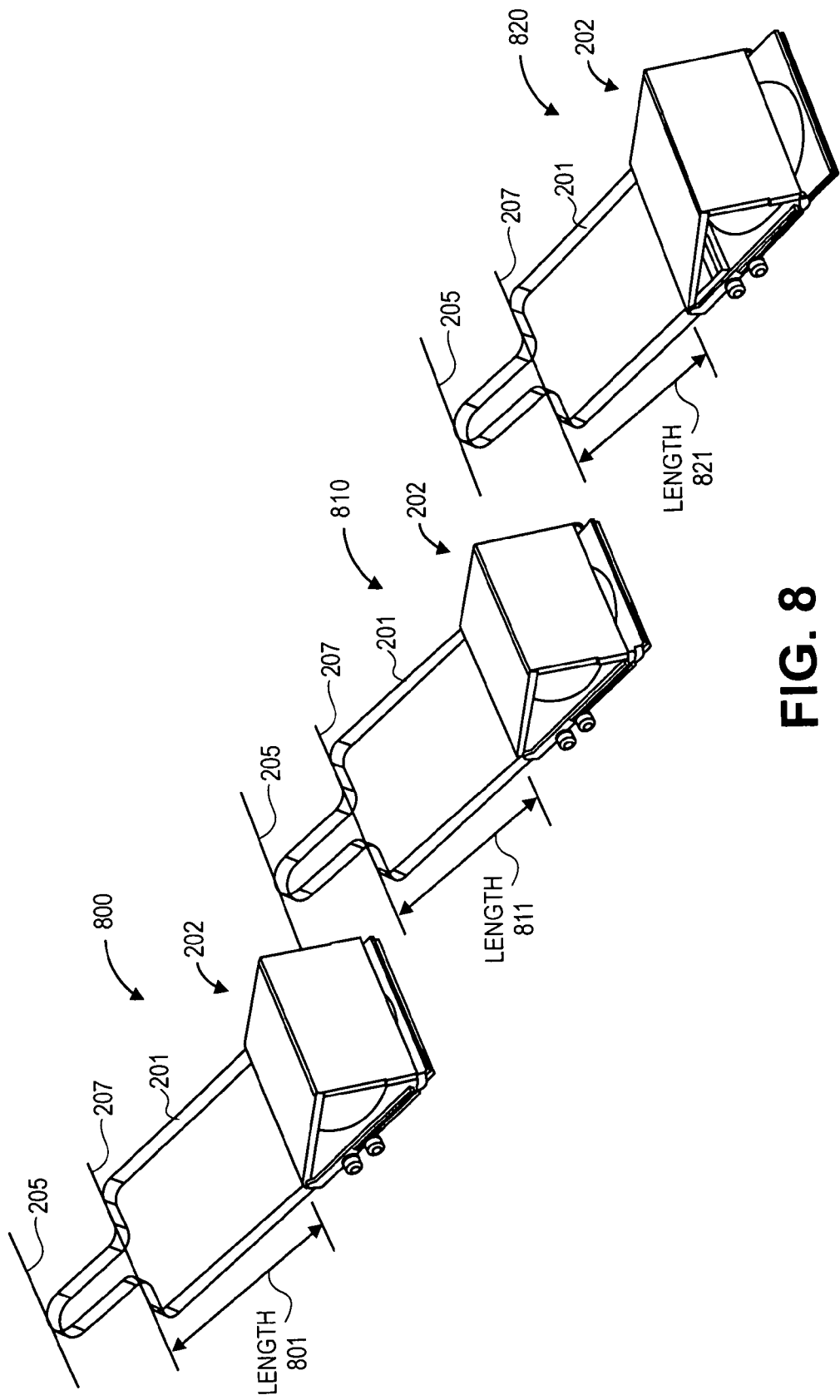
FIG. 8 illustrates elevated views of the treatment couch of FIG. 7 in various positions while in the bolster seat configuration.

FIG. 8 illustrates elevated views of the treatment couch of FIG. 7 in various positions 800, 810, and 820 while in the bolster seat configuration 700. As described above, while the lower-torso assembly 202 is in the bolster seat configuration 700 it can be adjusted relative to the head and 205 or the shoulder line 207 in the longitudinal direction 206. While the lower-torso assembly 202 is in position 800 the distance between the shoulder line 207 and the lower-torso assembly 202 has a length 801. The position 800 may be used to accommodate a patient having a similar length between the shoulders and the lowest point of the rear pelvic area of the patient. For patients having a length between their shoulder and the lowest point of the rear pelvic area that is shorter than length 801, the lower-torso assembly 202 can be adjusted towards the shoulder line 207 to position 810. While the lower-torso assembly 202 is in position 810, the distance between the shoulder line 207 and the lower-torso assembly 202 has a length 811. The length 811 is less than the length 801. For patients having a length between their shoulder and the lowest point of the rear pelvic area that is shorter than length 811, the lower-torso assembly 202 can be adjusted towards the shoulder line 207 to position 820. While the lower-torso assembly 202 is in position 820, the distance between the shoulder line 207 and the lower-torso assembly 202 has a length 821. The length 821 is less than the lengths 811 and 801. By adjusting the position of the lower-torso assembly 202 relative to the shoulder line 207 (or head and 205) in the longitudinal direction 206, a patient may be adjusted relative to the shoulder line 207. The lower-torso assembly 202 may be adjusted to align shoulders of the patient to a common point on the tabletop regardless of the height of the patient. As described above, in one embodiment, the difference or delta between the 99% male and the 1% female is approximately 7.44 inches. In another embodiment, the length between the head end and the shoulder line is approximately 6 inches when a mounting device is mounted to the head end of the tabletop to secure the patient to the tabletop 201.

In one embodiment, the radiolucent region of the tabletop 201 extends from the head and 205 to the lower-torso assembly 202 when in the position 800. When the lower-torso assembly 202 is moved towards the shoulder line 207, such as position 810, a portion of the lower-torso assembly 202 extends into the radiolucent region 204 of the tabletop 201. However, it should be noted that the imaging zone, which is the area of interest of the patient of which x-ray images are taken, is not obstructed by the lower-torso assembly 202 since the bottom point of the rear pelvic area of the patient (e.g., a patient that has a length between the shoulders and the rear pelvic area that is less than length 801) remains above the lower-torso assembly 202 in all positions, such as illustrated in positions 800, 810, and 820. The imaging zone of the patient is free from imaging obstructions by the lower-torso assembly 202 regardless of the height of the patient. The components of the lower-torso assembly 202 remain outside the imaging zone and substantially outside the radiolucent region 204 of the tabletop 201 in the various positions that accommodate the majority of patient heights (e.g., $1^{st}$ percentile female to the $99^{th}$ percentile male).

Figure 9A:
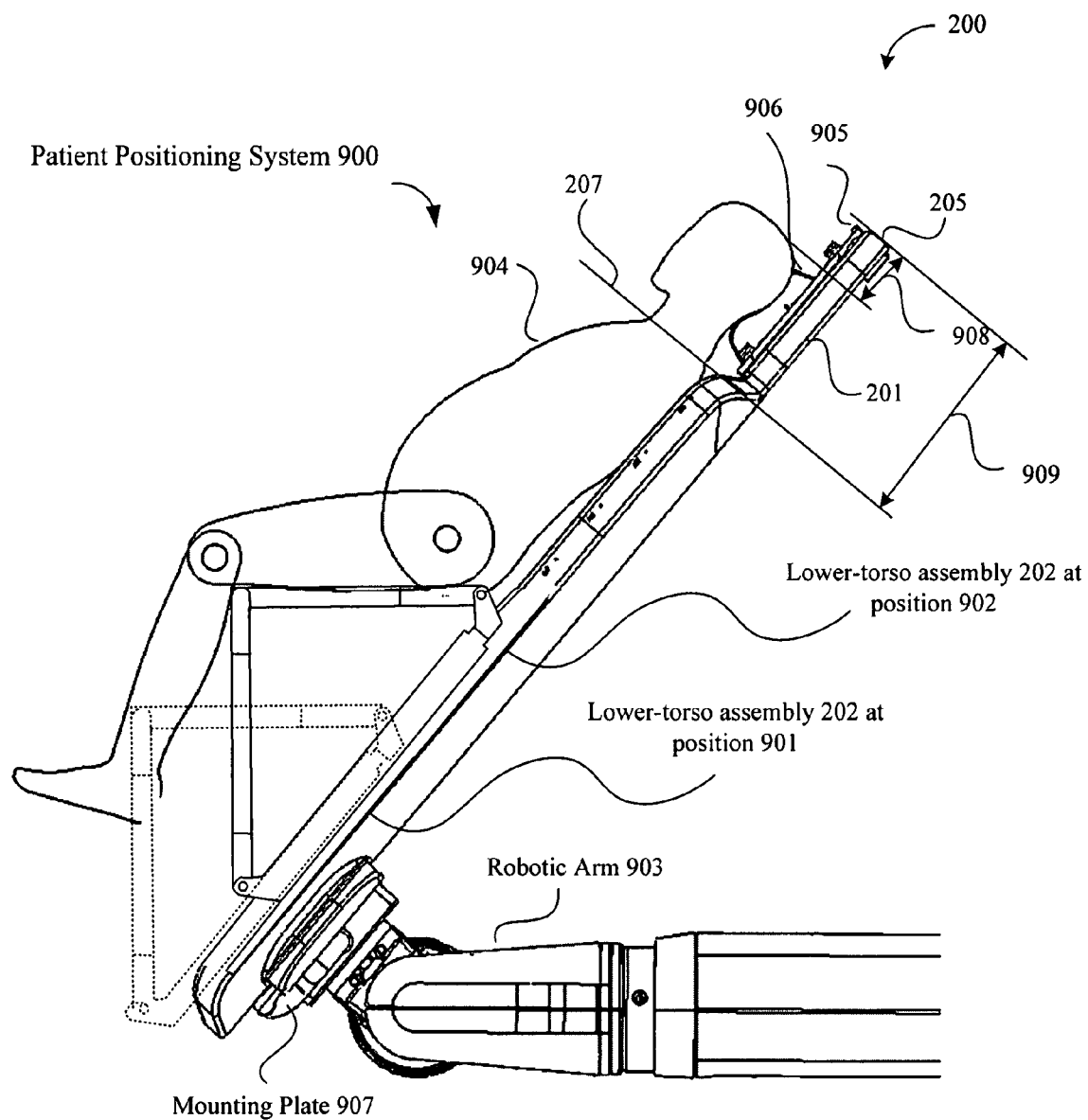
FIG. 9A illustrates one embodiment a patient positioning system, including a treatment couch and a robotic arm, and a patient at two positions on the treatment couch while the treatment couch is in a non-horizontal loading position.

FIG. 9A illustrates one embodiment a patient positioning system 900, including a treatment couch 200 and a robotic arm 903, and a patient at two positions on the treatment couch 200 while the treatment couch 200 is in a non-horizontal position. Patient positioning system 900 includes treatment couch 200, which includes tabletop 201 and lower-torso assembly 202, as described herein, and robotic arm 903. The robotic arm 903 is coupled via a mounting plate 907 to a mounting area on the tabletop 201 of the treatment couch 200. Alternatively, the treatment couch 200 may include an extension mounting area (e.g., offset bracket 260 of FIG. 2A) to which the robotic arm 903 is mounted. Robotic arm 903 may include multiple degrees of freedom. In one exemplary embodiment, the robotic arm may include 6 degrees of freedom. In another exemplary embodiment, the robotic arm 903 may include components manufactured by KUKA Roboter GmbH of Germany. Alternatively, the robotic arm 903 may have more or less than 6 degrees of freedom, and may utilize other motorized mechanisms known by those of ordinary skill in the art used to position a treatment couch. For example, the robotic arm 903 may include an additional axis mounted that is mounted at the lower section 232 of the tabletop 201 to rotate the tabletop 201 in an additional degree of freedom. The controller, which controls the robotic arm 203, may also control this additional degree of freedom.

Treatment couch 200 of FIG. 9A may include a head cushion 906 for the head of the patient 904. The head cushion 906 may be secured to the treatment couch via mounting device 905. The head cushion 906 provides support to the patient's head and may slide in a translational direction relative to the head end 205 of the tabletop 201. The head cushion 906 may also be integrated into the body tabletop 201. In another embodiment, the mounting device 905 may be used to secure a mask to the patient 904. The mask may be used to secure the patient to the treatment couch 200 to limit the mobility of the patient 904 during treatment.

The lower-torso assembly 202 of FIG. 9A may be configured to move along a longitudinal direction relative to the shoulder line 207 (or head end 205) of the tabletop 201, as described herein. In one embodiment, the patient 904 is loaded on the treatment couch 200 in a non-horizontal position, such as illustrated in FIG. 9A. The shoulders of the patient 904 at position 901 are not aligned with the shoulder line 207. As such, the lower-torso assembly 202 may be repositioned to the second position 902 so that when loaded on the treatment couch 200, the shoulders of the patient 904 are substantially aligned with the shoulder line 207. Although the patient may be aligned with respect to the shoulder line 207, similarly, the patient may be aligned to another point on the tabletop 201, such as with respect to the head end 205 of the tabletop 201.

In another embodiment, the patient 904 is loaded onto the treatment couch 200, such as when the treatment couch 200 is positioned in a non-horizontal position and the lower-torso assembly 202 is at the first position 901, as a loading position. The patient may be loaded onto the lower-torso assembly 202 in a sitting position (e.g., the seat pan of the lower-torso assembly is substantially parallel to the floor of the treatment room), such that a patient can merely sit down on the bolster seat, and lay back against the tabletop 201. Alternatively, the patient may be loaded onto the treatment couch 200 using other methods. After loading the patient onto the treatment couch 200, the lower-torso assembly 202 may be moved from the loading position 901 to a second position 902. The second position 902 may be a treating position since the second position 902 of the lower-torso assembly 202 aligns the shoulders substantially with the shoulder line 207. Alternatively, the treating position 902 may be where the head of the patient 904 is positioned towards the head end 205 of the tabletop 201. In one exemplary embodiment, the distance 908 between the head of the patient and the head end 205 may have a range of approximately zero to six inches. In another exemplary embodiment, the distance 909 between the head end 205 and the shoulder line 207 of the tabletop 201 may have a range of approximately 333 mm to 287 mm, as described above in Table 1-1. The variations in shoulder to head length are approximately 46 mm (approximately 1.8 inches). Alternatively, plus or minus 1 inch of adjustability may be provided to accommodate for variations in this dimension. After treatment is completed, the lower-torso assembly 202 may be moved from the treating position 902 to the loading position 901 for unloading the patient 904 from the treatment couch 200. Although in this embodiment, the patient is adjusted on the treatment couch 200 after being loaded onto the treatment couch 200, alternatively, the patient is adjusted to the shoulder line of the treatment couch 200 by adjusting the lower-torso assembly 202 before the patient is loaded onto the treatment couch 200.

Figure 9B:
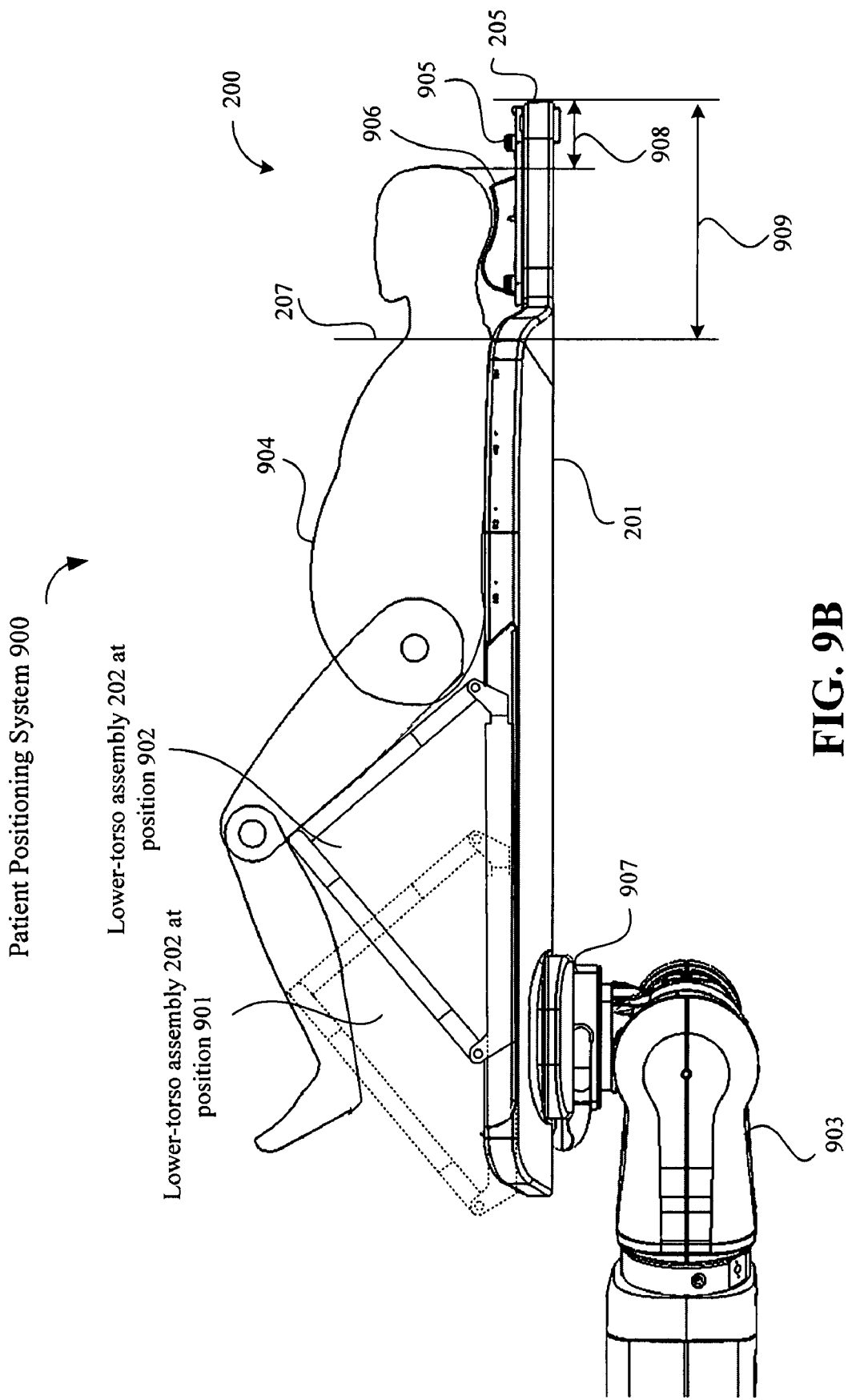
FIG. 9B illustrates the embodiment of FIG. 9A in a horizontal position, and the patient at two positions on the treatment couch while the treatment couch is in the horizontal position.

FIG. 9B illustrates the embodiment of FIG. 9A in a horizontal position, and the patient at two positions on the treatment couch while the treatment couch is in the horizontal position. As described above, the lower-torso assembly 202 is configured to move along the longitudinal direction relative to the shoulder line 207 (or the head end 205) of the tabletop 201. In one embodiment, the patient 904 is loaded on the treatment couch 200 in a horizontal position, such as illustrated in FIG. 9B. The shoulders of the patient 904 at position 901 are not aligned with the shoulder line 207. As such, the lower-torso assembly 202 may be repositioned to the second position 902 so that when loaded on the treatment couch 200, the shoulders of the patient 904 are substantially aligned with the shoulder line 207. Although the patient may be aligned with respect to the shoulder line 207, similarly, the patient may be aligned to another point on the tabletop 201, such as with respect to the head end 205 of the tabletop 201.

In another embodiment, the patient 904 is loaded onto the treatment couch 200, such as when the treatment couch 200 is positioned in a non-horizontal position and the lower-torso assembly 202 is at the first position 901, as a loading position. The patient may be loaded onto the lower-torso assembly 202 in a laying-down position (e.g., the patient sits on the tabletop 201, or on the lower-torso assembly 202 when in the flat tabletop configuration, which is substantially parallel to the floor of the treatment room, and then lays down on the treatment couch 200). Alternatively, the patient may be loaded onto the treatment couch 200 using other method. After loading the patient onto the treatment couch 200, the lower-torso assembly 202 may be moved from the loading position 901 to a second position 902. It should be noted that by loading the patient before adjustments are made to align the patient to the shoulder line, the patient may experience some discomfort from the patient's skin sliding along the tabletop. The second position 902 may be a treating position since the second position 902 of the lower-torso assembly 202 aligns the shoulders substantially with the shoulder line 207. Alternatively, the treating position 902 may be where the head of the patient 904 is positioned towards the head end 205 of the tabletop 201. In one exemplary embodiment, the distance 908 between the head of the patient and the head end 205 may have a range of approximately zero to six inches. In another exemplary embodiment, the distance 909 between the head end 205 and the shoulder line 207 of the tabletop 201 may have a range of approximately 15 inches. In one embodiment, three inches may be used for attaching a mounting device. Alternatively, other dimensions may be used.

After treatment is completed, the lower-torso assembly 202 may be moved from the treating position 902 to the loading position 901 for unloading the patient 904 from the treatment couch 200. Although in this embodiment, the patient is adjusted on the treatment couch 200 after being loaded onto the treatment couch 200, alternatively, the patient is adjusted to the shoulder line of the treatment couch 200 by adjusting the lower-torso assembly 202 before the patient is loaded onto the treatment couch 200. As described above, adjusting the lower-torso assembly 202 after the patient is loaded onto the treatment couch may cause some discomfort to the patient.

In one embodiment, the lower-torso assembly 202 is moved to adjust the patient 904 to a treating position 902 from a loading position 901. Treating position 902 may be where the head of the patient 904 is positioned or aligned so that there is substantially no distance (e.g., distance 908) between the head of the patient and the head end 105 of the treatment couch 101. Alternatively, the treating position 902 may be where the shoulders of the patient 904 are substantially aligned with the shoulder line 207. This may allow a radiation source (not illustrated in FIG. 9A or 9B to be positioned with respect to the head of the patient with minimal interference from the treatment couch 200, or without any interference from the treatment couch 200. For example, if a shorter patient (e.g., 1 percentile female height of 58.1 inches) is loaded onto the treatment couch 200 in position 901, the patient's shoulders are not aligned to the shoulder line 207 because of the height of the shorter patient. However, by moving the lower-torso assembly 202 of the treatment couch 200 towards the head end 205 of the treatment couch 200 (e.g., from position 901 to position 902), the patient's shoulders may be adjusted to be aligned with the shoulder line 207 of the treatment couch 200. As described above, the lower-torso assembly 202 may adjust the patient relative to the shoulder line 207 of the tabletop 201 while the patient is loaded onto the treatment couch 200, or alternatively, before the patient is loaded onto the treatment couch 200.

In one embodiment, the treatment couch 200, including the lower-torso assembly 202, is coupled to the robotic arm 903. The robotic arm 903 includes a controller. The controller moves the treatment couch 200 along one or more degrees of freedom, for example, along at least 5 degrees of freedom. In this embodiment, the lower-torso assembly 202 is controlled (e.g., positioned or converted between configurations) independent of the motions of the robotic arm 903 controlled by the controller.

In one embodiment, the robotic arm 903 and the treatment couch 200, including the lower-torso assembly 202 can be positioned to provide a seat for loading a patient. In one embodiment, the seat pan of the lower-torso assembly 202, when in the bolster seat configuration, is substantially parallel to the floor at a distance of approximately 15 inches from the floor of the treatment room. In another embodiment, the treatment couch 200 may be positioned to provide a seat pan that is at a distance of approximately 18 inches from the floor. Alternatively, the distance may be greater than 15 inches from off the floor.

In one exemplary embodiment, the robotic arm may be used to position the treatment couch in five degrees of freedom. The five degrees of freedom may include two rotational axes for translational movements along mutually orthogonal x-, and y-horizontal coordinate axes; and three rotational axes for roll-, pitch-, and yaw-rotational movements about x-, y-, and z-axes, respectively. In another embodiment, the robotic arm may position the treatment couch using six degrees of freedom, for example, five rotational degrees of freedom as previously described, and one substantially vertical or horizontal, linear degree of freedom. The one substantially vertical, linear degree of freedom may include a substantial linear axis for translation along a substantially vertical line in a z-coordinate axis perpendicular to the horizontal, x-, and y-coordinate axes. The one substantially horizontal, linear degree of freedom may include a substantially linear axis for translation along a substantially horizontal line in the horizontal, x-, and y-coordinate axes perpendicular to the z-coordinate axis. In another embodiment, the robotic arm positions the treatment couch using seven degrees of freedom, six rotational degrees of freedom, and one substantially vertical, linear degree of freedom. In one embodiment, the seventh degree of freedom is an additional rotational axis at the lower sections 232 of the tabletop 201, as described above. Alternatively, the robotic arm may include less than five degrees of freedom, such as one, two or three degrees of freedom.

The robotic arm may be coupled directly to the treatment couch 200 in a mounting region, or alternatively to the extension mounting area, such as using offset bracket 260 of FIG. 2A. Alternatively, if the patient treatment couch 200 is sufficient thickness in the mounting region, the robotic arm may be mounted directly to an edge side of the treatment couch without the use of extension mounting area. The mounting of robotic arm on extension mounting area (or, alternatively, on to edge side) may be used to allow the robotic arm to be out of the imaging field of view for all supported treatment positions.

In one embodiment, the loading position may be when the treatment couch 200 is tilted approximately 42 degrees from a perpendicular axis to the floor of the treatment room. In another embodiment, the loading position may be at approximately 50 degrees from the perpendicular axis. By lowering the loading position from 42 degrees to 50 degrees, the distance that the leg rest must travel from the loading position to the treating position may be lowered. These exemplary embodiments of 42 degrees and 50 degrees are for loading a patient in a non-horizontal position (illustrated in FIG. 9A); however, it should also be noted that the loading position may be in a horizontal position, 90 degrees from the perpendicular axis to the floor of the treatment room, as illustrated in FIG. 9B. Alternatively, other degrees of tilt for the loading position may be used based on patient comfort.

In one embodiment, the treating position is where the head of the patient is positioned or aligned so that there is substantially no space between the head of the patient and the head end 105 of the treatment couch 101. In one exemplary embodiment, the distance between the head of the patient and the head end 105 for the treating position 108 may have a range of approximately zero to six inches. In one embodiment, the treating position is where the head of the patient is located within the head area 203. The head area 203 may be less in width than the treatment couch 200 to allow a radiation source to be positioned closer to the patient's head. It should be noted, however, that the width of the head area 203 and the treatment couch 200 may be the same width.

It should be noted that the term treating position, as used herein, is used to describe how the patient is positioned or adjusted on the treatment couch 200 relative to the head end 205 of the treatment couch 200. The term treatment position, as used herein, is used to describe how the treatment couch 200 is positioned in a treatment room and/or relative to a radiation source. It should also be noted that the treatment positions within a treatment room may be a seated position where the treatment couch is tilted at an angle from the ground of the treatment room (as illustrated in FIG. 9A), or alternatively, a horizontal position where the treatment couch is substantially parallel to the ground of the treatment room (as illustrated in FIG. 9B). In other words, the patient may be positioned (or adjusted) on the treatment couch 101 relative to a head end 106, and positioned in the treatment room (by positioning the treatment couch 101). These positioning operations may be done concurrently or subsequently to one another.

Figure 10A:
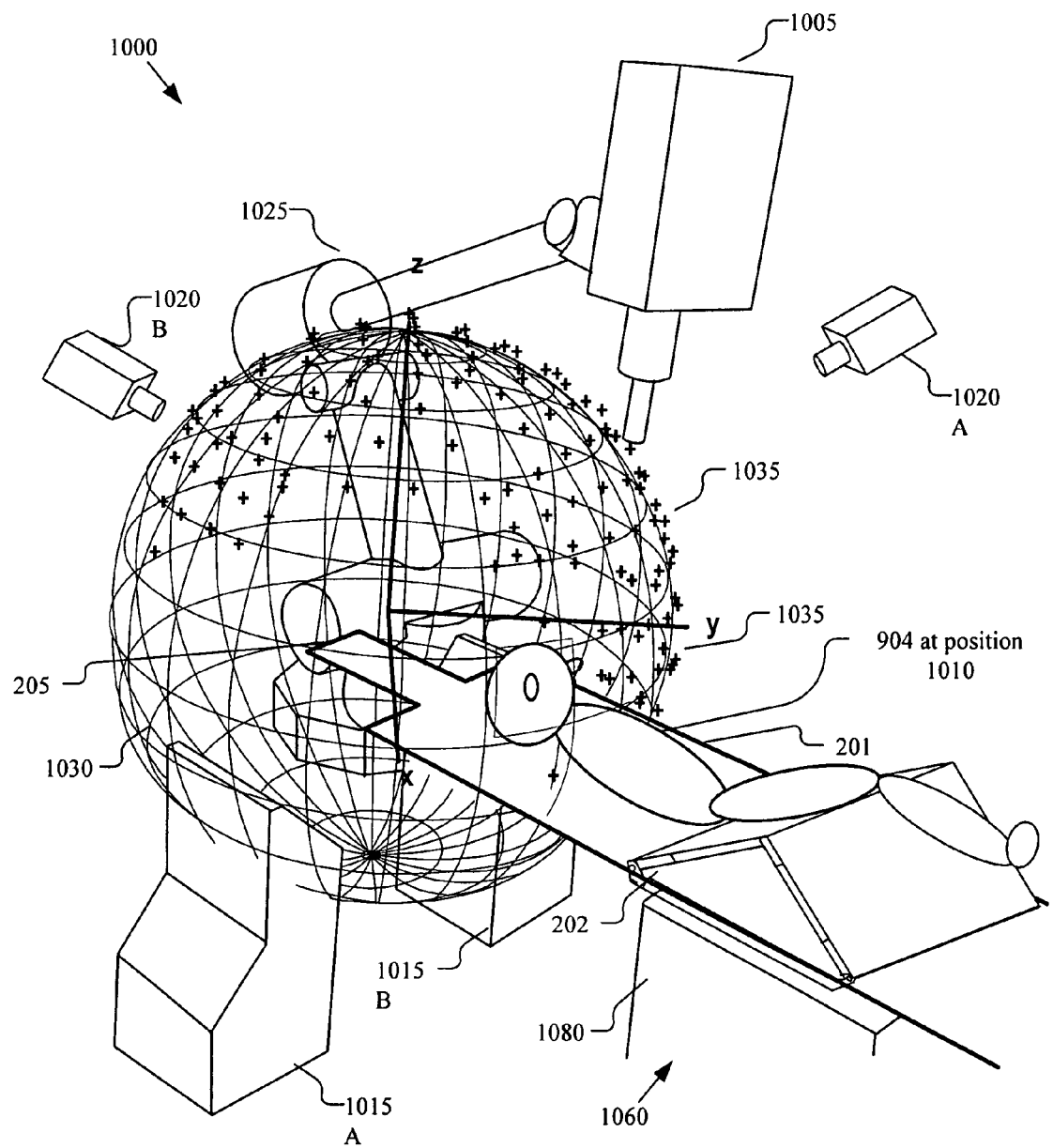
FIG. 10A is a perspective view illustrating a patient in a first position of a workspace of a radiation treatment system including a set of spatial nodes at which to position the radiation source, in accordance with an exemplary embodiment of the invention.

FIG. 10A is a perspective view illustrating a patient in a first position of a workspace of a radiation treatment system including a set of spatial nodes at which to position the radiation source, in accordance with an exemplary embodiment of the invention. The illustrated embodiment of radiation treatment system 1000 includes a radiation source 1005, detectors 1015A and 1015B (collectively 1015, also referred to as imagers), imaging sources 1020A and 1020B (collectively 1020), and a robotic arm 1025.

The illustrated embodiment also includes a patient positioning system 1060. Patient positioning system 1060 includes a treatment couch 200 and a stand 1080. Alternatively, treatment couch 200 may be coupled to a robotic arm (e.g., 903), or other motorized positioning system known by those of ordinary skill in the art. Patient positioning system 1060 also includes the lower-torso assembly 202. The lower-torso assembly 202 may be used to adjust an upper-half of the patient 904 relative to a head end of the tabletop 201. In this exemplary embodiment, the patient 904 is positioned at position 1010. Position 1010 may be a loading position. The loading position may include the tabletop 201 being in a horizontal position, or alternatively, in a non-horizontal position.

Figure 10B:
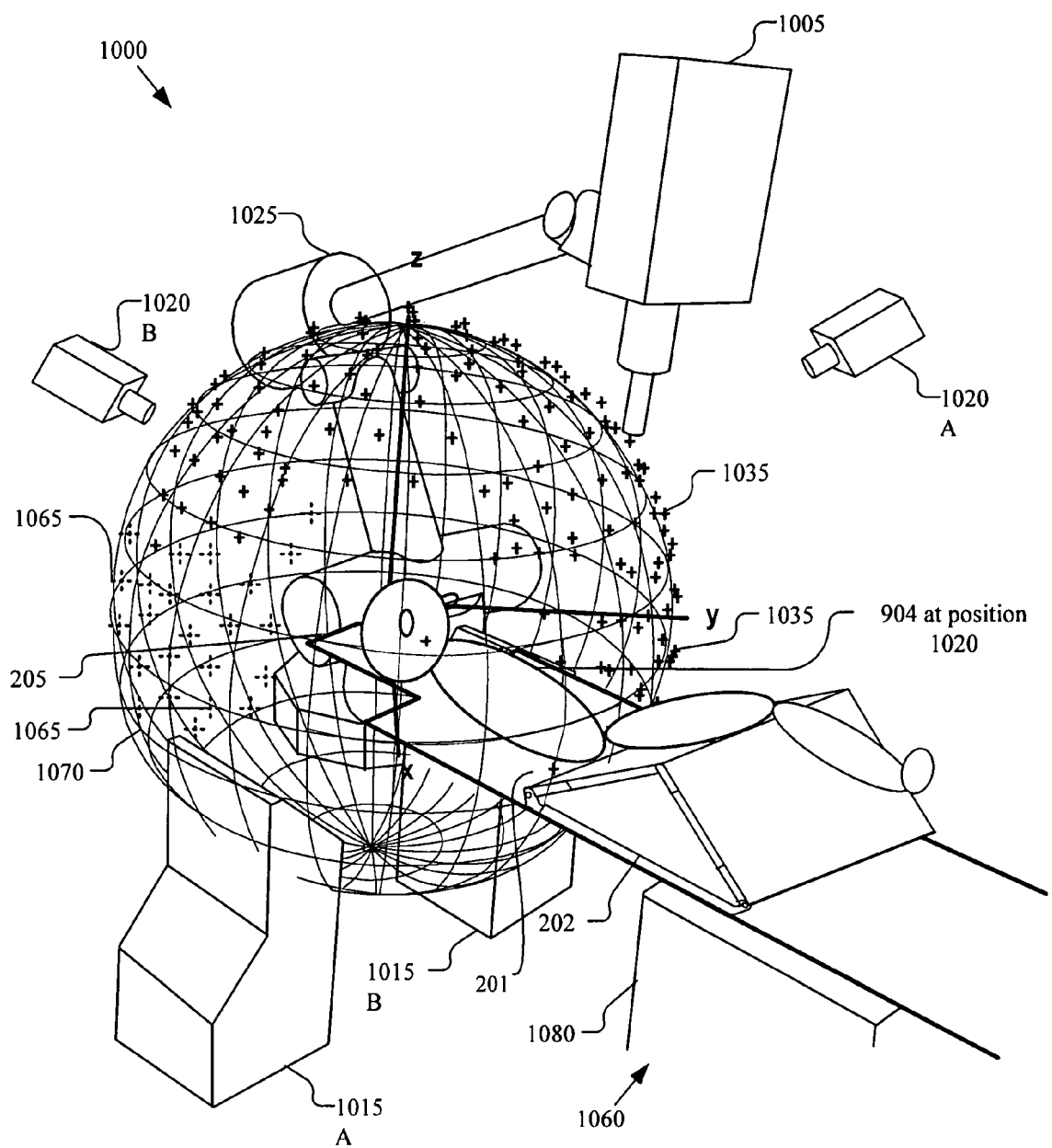
FIG. 10B is a perspective view illustrating the patient in a second position of the workspace of the radiation treatment system, in accordance with the embodiment of FIG. 10B.
Figure 13:
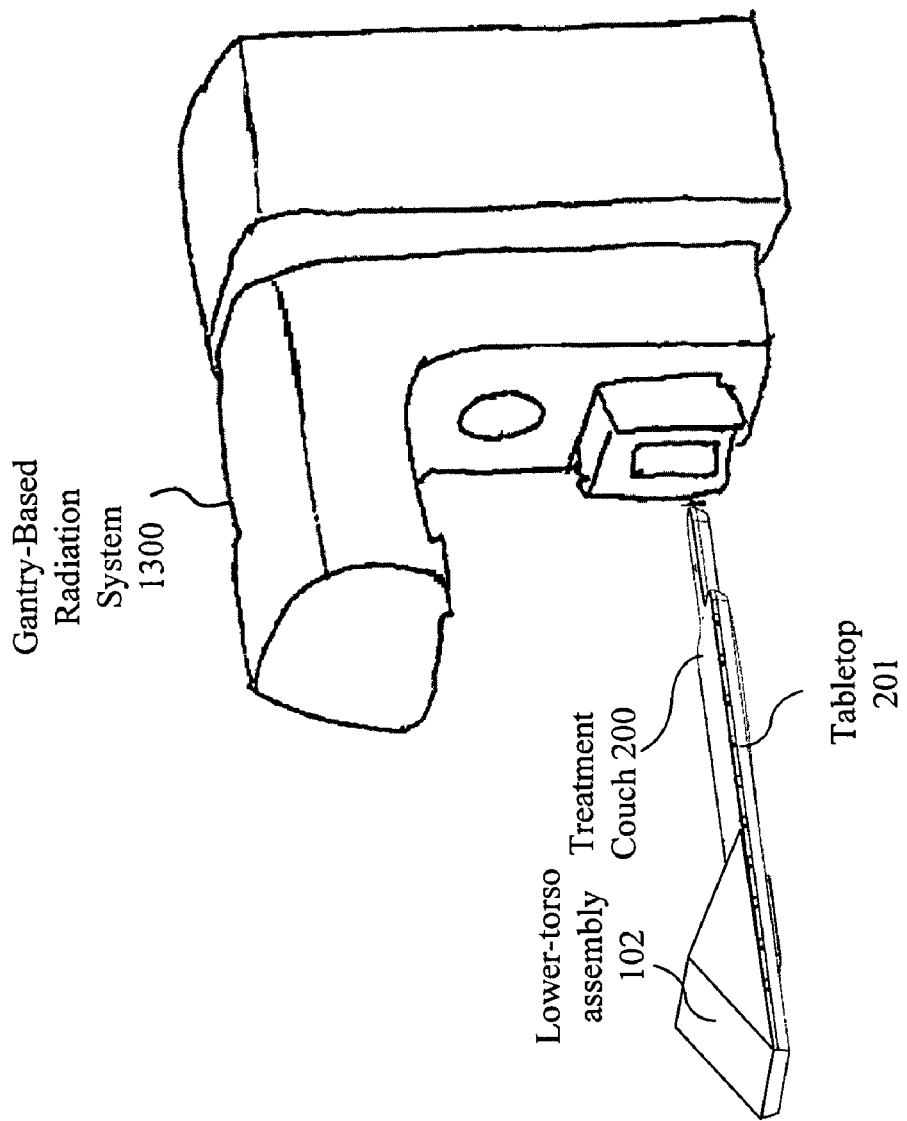
FIG. 13 illustrates a system having a gantry-based radiation treatment system and a treatment couch according to one embodiment.

Radiation treatment system 1000 may be used to perform radiation treatment (e.g., radiosurgery and/or radiotherapy) to treat or destroy a lesion (e.g., tumorous tissue) within a patient. During radiation treatment, the patient rests on tabletop 201, which is maneuvered to position a volume of interest ("VOI") containing a target to a preset position or within an operating range accessible to radiation source 1005 (e.g., field of view). In one embodiment, radiation treatment system 1000 is an image guided radiation treatment system. In one exemplary embodiment, the radiation treatment system 1000 is a frameless, image-guided robot-based therapeutic radiation treatment system utilizing a linear accelerator ("LINAC"), such as the CyberKnife® system developed by Accuray, Inc. of Sunnyvale, Calif. Alternatively, the therapeutic radiation treatment system 1000 may be a gantry-based (iso-centric) treatment system or other type of medical operation systems, such as illustrated in FIG. 13. Together, imaging sources 1020 and detectors 1015 are an imaging guidance system that provides visual control over the position of tabletop 201 and the patient thereon and the alignment of radiation source 1005 with respect to the VOI within the patient. In one embodiment, the patient positioning system tabletop 201 is coupled to a positioning system 1080, such as robotic arm 903, which receives feedback from the imaging guidance system to provide accurate control over both the displacement and orientation of the VOI within the patient relative to radiation source 1005. In another embodiment, positioning system 1080 is a stand, as illustrated in FIGS. 10A and 10B, or a motorized positioning system known by those of ordinary skill in the art.

In one embodiment, robotic arm 1025 has multiple (e.g., six) degrees of freedom capable of positioning the radiation source 1005 with almost an infinite number of positions and orientations within its operating envelope.

A collection of spatial nodes and associated safe paths interconnecting these spatial nodes is called a "workspace" or "node set". FIG. 10A illustrates a workspace 1030, including a number of spatial nodes 1035 each represented by a "+" symbol (only a couple are labeled). Multiple different workspaces may be created and defined for different patient work areas. For example, workspace 1030 may be spherical (as illustrated) and defined for treating VOIs residing within the head of a patient 904. Alternatively, workspace 1030 may have other geometries (e.g., elliptical) and defined for treating VOIs residing within other areas of a patient. Additionally, multiple workspaces 1030 may be defined for different portions of a patient, each having different radius or source to axis distances ("SAD"), such as 650 mm and 800 mm. The SAD is the distance between the collimator lens in radiation source 1005 and the target within the VOI. The SAD defines the surface area of the workspace. In one embodiment of an elliptical workspace, the SAD may range from 900 mm to 1000 mm. Other SADs may be used.

Spatial nodes 1035 reside on the surface of workspace 1030. Spatial nodes 1035 represent positions where the radiation source 1005 is pre-programmed to stop and delivery a dose of radiation to the VOI within the patient. During delivery of a treatment plan, robotic arm 1025 moves radiation source 1005 to each and every spatial node 1035, where a dose is determined to be delivered, following a predefined path. The predefine path may also includes some spatial nodes 1035 where no dose needs to be delivered, in order to simplify the motions of the robotic arm.

FIG. 10A illustrates a node set including an exemplary number of spatial nodes 1035 (e.g., 100 to 115). The node set may include spatial nodes 1035 substantially uniformly distributed over the geometric surface of workspace 1030. The node set includes all programmed spatial nodes 1035 and provides a workable number of spatial nodes 1035 for effectively computing treatment plan solutions for most ailments and associated VOIs. The node set provides a reasonably large number of spatial nodes 1035 such that homogeneity and conformality thresholds can be achieved for a large variety of different VOIs, while providing enough vantage points to avoid critical structures within patients. It should be appreciated that the node set may include more or less spatial nodes 1035 than is illustrated or discussed. For example, as processing power increases and experience gained creating treatment plans, the average number of spatial nodes 1035 may increase with time to provide greater flexibility and higher quality treatment plans.

FIG. 10A illustrates a patient 904 in a first position (e.g., 1010) of workspace 1030 of the radiation treatment system 1000 including a set of spatial nodes 1035 at which to position the radiation source 1005. In this exemplary embodiment, the height of patient 904 is smaller than the height of the tabletop 201 from the head end of the tabletop 201 to the position of the lower-torso assembly 202. Because of the placement of the head of patient 904 the radiation source 1005 may be positioned at the exemplary spatial nodes 1035.

FIG. 10B is a perspective view illustrating the patient in a second position of the workspace of the radiation treatment system, in accordance with the embodiment of FIG. 10A. As previously described with respect to FIG. 10A, the height of patient 904 is smaller than the height of the tabletop 201 from the head end of the tabletop 201 to the position of the lower-torso assembly 202 when the patient is in the first position 1010. However, by moving the lower-torso assembly 202, as described herein in the present embodiments, relative to the head end 205 (or shoulder line 207) of the tabletop 201, the head of patient 904 may be positioned at a second position 1020. Because the head of the patient 904 is positioned closer to the head end 205 (or shoulder line 207) of the tabletop 201 in second position 1020, the available spatial nodes increases (e.g., increased spatial nodes 1065), as illustrated as dashed "+" in FIG. 10B. When the patient is positioned or aligned to the head end 205 of the tabletop 201 (e.g., position 1020), the available number of spatial nodes 1035 of workspace 1070 of FIG. 10B, which includes spatial nodes 1035 and increased spatial nodes 1065, is greater than the number of available number of spatial nodes of workspace 1030 when the patient is positioned at the first position 1010. In other words, by adjusting the patient (e.g., upper-half of the patient) relative to the head end 205 (or shoulder line 207) of the tabletop 201, the available workspace 1070 (e.g., including the increased number of spatial nodes 1065) of the radiation source 1005 of radiation treatment system 1000 is increased. By moving the patient from the first position 1010 to the second position 1020, the radiation source 1005 may access certain zones (e.g., spatial nodes) near the tabletop 201 that were previously blocked by the tabletop 201 when the patient was in the first position 1010. Having greater accessibility to those certain zones, which were previously blocked by the tabletop 201, increases the workspace 1070 (e.g., spatial nodes at which the radiation source 1005 may deliver radiation to the target).

Figure 11A:
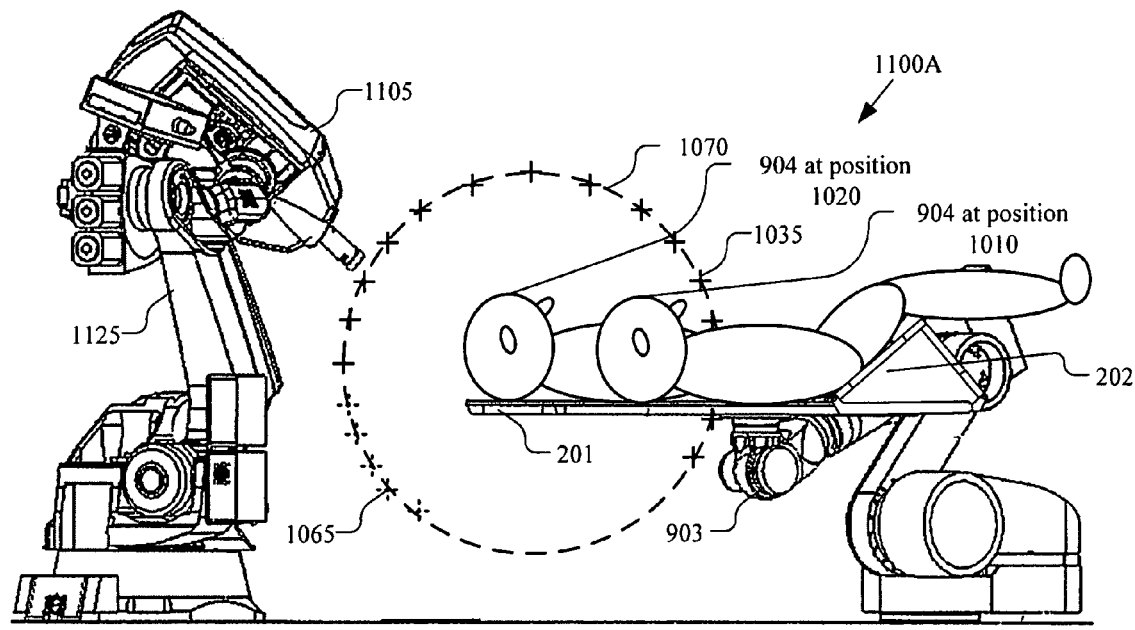
FIG. 11A is a side view illustrating a cross-section of a workspace of a radiation treatment system including a node set and an increased node set, in accordance to one embodiment.
Figure 11B:
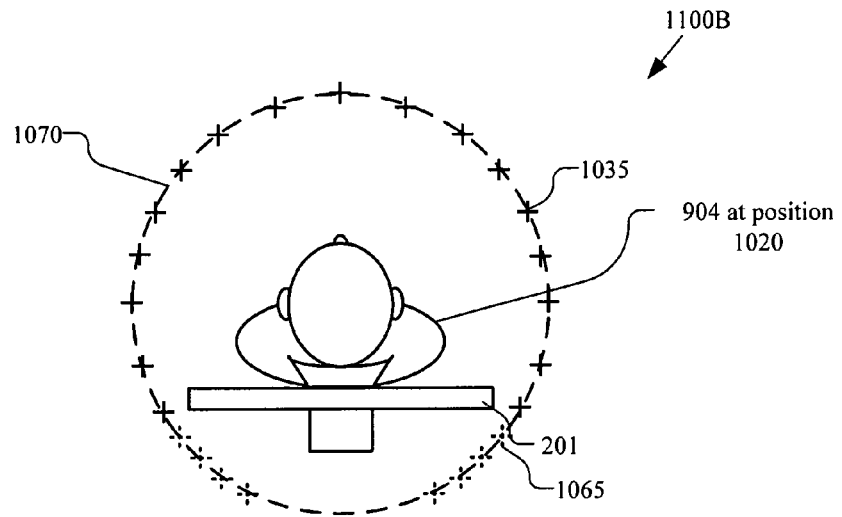
FIG. 11B is an end view illustrating a cross-section of a workspace of a radiation treatment system including a node set and an increased node set, in accordance to one embodiment.

FIG. 11A and FIG. 11B are side and end views illustrating a cross-section of a workspace of a radiation treatment system including a node set and an increased node set, in accordance to one embodiment. Cross-sections 1100A and 1100B illustrate how a node set of workspace 1070 may have spatial nodes 1035 and increased spatial nodes 1065 evenly distributed around its surface. Other distributions are possible.

Using large or complete node sets of spatial nodes 1035 and increased spatial nodes 1065 may increase flexibility to achieve conformality and homogeneity, while minimizing risk of complications to a patient for a wide variety of different VOIs. A larger node set provides a greater number of vantage points from which to delivery a radiation beam from radiation source 1005. The greater the number of vantage points the greater the flexibility to design a treatment plan that avoids beam trajectories passing close to or through critical structures of a patient. Avoiding proximity to critical structures reduces the risks of complication to a patient.

In one embodiment, the node set of workspace 1030 (as illustrated in FIG. 10A) is increased to be an increased node set of workspace 1070 (as illustrated and described with respect to FIG. 10B). By moving or adjusting the upper-half of patient 904 from a first position 1010 to a second position 1020, the number of node sets 1035 may increase (e.g., by increased spatial nodes 1065). Because the head of the patient 904 is positioned closer to the head end 205 (or shoulder line 207) of the tabletop 201 in second position 1020 than in the first position 1010, the available spatial nodes increases (e.g., increased spatial nodes 1065), as illustrated as dashed "+" in FIGS. 11A and 11B. For example, workspace 1070 includes spatial nodes 1035 and increased spatial nodes 1065 when the patient 904 is positioned at the second position 1020, while the workspace 1030 includes only node set 1035 when the patient 904 is positioned at the first position 1010.

In one exemplary embodiment, the treatment couch 200 is used when acquiring a pre-treatment image (e.g., a magnetic resonance (MR) image, a computerized tomography (CT) image, fluoroscopy image, and a positron emission tomography (PET) image) of a patient in a pre-treatment position (including the treating position) for treatment planning purposes. The pre-treatment position may be recorded electronically or mechanically at the time of acquiring the pre-treatment image, and manually or automatically loaded to restore the same position of the treatment couch 200 during treatment. This may be done not only to ensure positioning with respect to the pre-treatment position, but also, to ensure consistent treating positions across multiple fractions (e.g., multiple treatments of the patient).

Restoration of the pre-treatment position may be used to aid in registration of the patient. Registration of a patient using a radiation system may be used in an initial patient setup as a positioning procedure for aligning a patient to be in a same position as when the patient was imaged during treatment planning. During treatment planning, pre-treatment images (as an initial reference image) of the patient are taken and used to plan radiation to be delivered by the radiation source. Subsequent images (e.g., treatment images) are then registered with the pre-treatment image in order to determine the location or displacement of the target (e.g., tumor) with respect to the pre-treatment scan (initial reference image). The displacement of the target determined by the registration may be used to adjust the patient position such that the displacement is minimized to within an operating range of the radiation treatment system. This enables the radiation source to be controlled to deliver radiation beams as specified by the treatment plan. After the patient is positioned during the initial patient setup, then the radiation may be delivered to the target of the patient from the radiation source.

Restoration of the pre-treatment position, or intra-fraction treatment positions, may be particularly helpful with a non-image guided radiation system, which relies on precise target alignment with the radiation source, as opposed to an image-guided radiation system, which enables the radiation source manipulator to track and correct for changes in patient target position during treatment delivery.

Restoration of the pre-treatment position may also be used to aid in immobilization of the patient. Immobilization may be used to maintain a constant spatial relationship between the target and the radiation source to ensure accurate dose delivery. Immobilization may be affected by the positioning of the patient on the treatment couch. Thus, restoration of the treatment couch to a same position as a pre-treatment position may help immobilize the target with respect to a skeletal structure of the body, thereby, minimizing or eliminating tumor deformation and displacement. For example, during treatment of a target with the sacrum region, when a patient is positioned on the treatment couch, the patient's skeletal structure and organs comes to rest. However, by changing the position of the legs (e.g., tilting the legs at a different angle), the target (e.g., tumor) may change by displacement or by deformation based on how the legs are positioned with respect to the skeletal structure. This may be used for both image-guided and non-image-guided radiation treatment systems.

Figure 12:
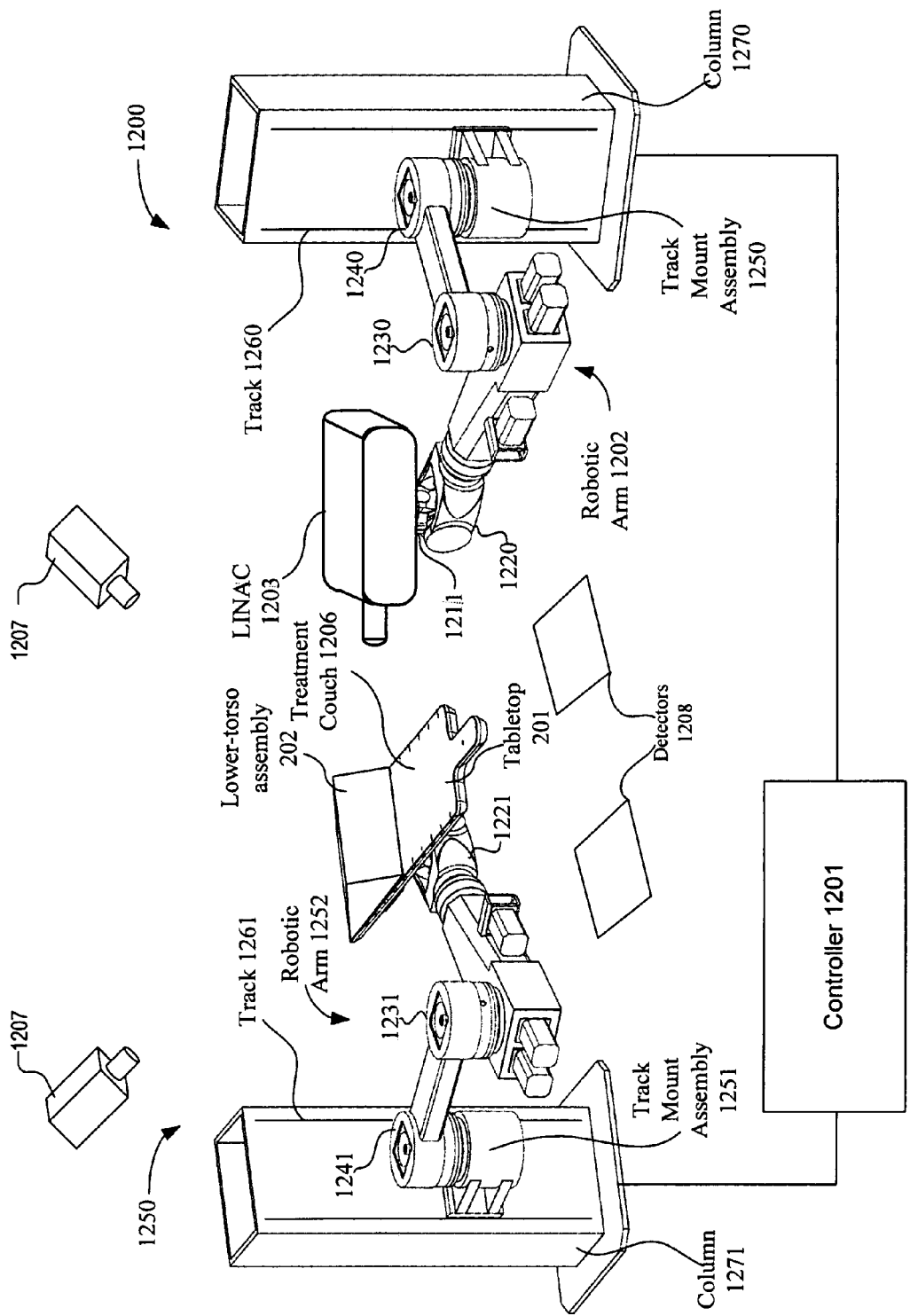
FIG. 12 illustrates a system having a robot-based radiation treatment system and a robot-based patient positioning system having a treatment couch according to one embodiment.

FIG. 12 illustrates a system having a robot-based treatment delivery system 1200 and a robot-based patient positioning system 1250 having a treatment couch according to one embodiment. The robot-based treatment delivery system 1200 includes a robotic arm 1202 having a wrist assembly 1220, an elbow assembly 1230, a shoulder assembly 1240, a track mount assembly 1250, and a track 1260, a LINAC 1203, and a column 1270. The LINAC 1203 may be rotatably attached to the wrist assembly 1220, which includes a tool-yaw joint, a tool-pitch joint, and a tool-roll joint. The tool-yaw joint of wrist assembly 1220 may be coupled to mounting plate 1211, which may be attached to the bottom of the LINAC 1203. Alternatively, the tool-yaw joint of wrist assembly 1220 may be coupled directly to the bottom of the LINAC 1203. The tool-yaw joint of wrist assembly 1220 facilitates rotational movement of the LINAC 1203 in a yaw-rotation along the z-axis, axis 6. The tool-pitch joint may be coupled to the tool-yaw joint and facilitates rotational movement of the LINAC 1203 in a pitch-rotation along the y-axis, axis 5. The tool-roll joints may be coupled to the tool-pitch joint and facilitates rotational movement of the LINAC 1203 in a roll-rotation along the x-axis, axis 4.

The elbow assembly 1230 may be coupled to the tool-roll joint of wrist assembly 1220. The elbow assembly 1230 may include three drive shafts and three motors. In one embodiment, the motors discussed herein may be step motors. Alternatively, the motors may be servo motors or other motors known by those of ordinary skill in the art. The first drive shaft may be coupled to the tool-yaw joint and the first motor. The first motor and drive shaft drive rotational movement of LINAC 1203 along the yaw axis, axis 6. The second drive shaft may be coupled to the tool-pitch joint and the second motor. The second motor and drive shaft drive rotational movement of the LINAC 1203 along the pitch axis, axis 5. The third drive shaft may be coupled to the tool-roll joint and the third motor. The third motor and drive shaft drive rotational movement of the LINAC 1203 along the roll axis, axis 4.

The shoulder assembly 1240 may be coupled to the elbow assembly 1230 by an elbow joint and to the track mount assembly 1250 by a shoulder joint. The elbow joint includes an elbow gearbox, which may be configured to drive rotational movement of the elbow assembly 1230 of the robotic arm 1202 in a rotational axis, axis 3. The shoulder joint includes a shoulder gearbox, which may be configured to drive rotational movement of the shoulder assembly 1240 of the robotic arm 1202 in a rotational axis, axis 2. The elbow and shoulder gearboxes of the shoulder and elbow assemblies 1230 and 1240 facilitate translational movement of the LINAC 1203 in a two-dimensional horizontal plane, for example, in the (x-, y-) plane parallel with the floor.

In one embodiment, the controller 1201, the shoulder and elbow gearboxes of the robotic arm 1202, the track mount assembly 1250, and the wrist assembly 1220, may include components manufactured by KUKA Roboter GmbH of Germany. Alternatively, the controller, the shoulder and elbow gearboxes of the robotic arm 1202, the track mount assembly 1250, and the wrist assembly 1220 may include other types of components.

The track mount assembly 1250 may be coupled to a track 1260 and to the shoulder joint of the shoulder assembly 1240. The track mount assembly 1250 and track 1260 facilitate translational movement of the LINAC 1203 in a substantially vertical, linear axis, axis 1. The substantially vertical, linear axis (z-) may be substantially perpendicular to the two dimensional horizontal plane (x-, y-). In one embodiment, the track may be vertically oriented, for example, vertically mounted to a vertical side of column 1270. The column 1270 may be secured or mounted to the floor of the treatment room during therapeutic radiation treatment or below the floor in a pit. In another embodiment, column 1270 may be secured or mounted to the ceiling of the treatment room during therapeutic radiation treatment. Alternatively, the track 1260 may be vertically mounted to other structures known to those skilled in the art, such as a wall, pedestal, block, or base structure.

The above mentioned arrangement of the wrist assembly 1220, elbow assembly 1230, shoulder assembly 1240, track mount assembly 1250, and track 1260 facilitate the positioning of the LINAC 1203 using five rotational DOF and one translational substantially vertical, linear DOF. The five rotational and one translational substantially vertical, linear DOF of the robotic arm 1202 of the robot-based treatment delivery system 1200 may position the LINAC 1203 in substantially any place in a desired treatment area, such as a workspace within the mechanical range of motion of the robotic arm 1202. The robotic arm 1202 may position the LINAC 1203 to have a tool center position (TCP) or isocenter in multiple locations within the workspace or treatment area. Alternatively, the robotic arm 1202 may be configured to facilitate motion of the LINAC 1203 along five rotational DOF and one substantially vertical, linear DOF. In one exemplary embodiment, the five DOF includes two rotational axes for translational movements along mutually orthogonal, horizontal coordinate axes (x-, and y-); and three rotational axes for roll-, pitch-, and yaw-rotational movements about x-, y-, and z-axes, respectively. The one substantially vertical, linear DOF includes a substantially linear axis for translational movement along a substantially vertical line in a coordinate axis (z-) substantially perpendicular to the horizontal coordinate axes (x-, and y-). Alternatively, the substantially linear DOF is a substantially horizontal, linear DOF that includes a substantially linear axis for translational movement along a substantially horizontal line in horizontal coordinate axes (x-, and y-) substantially perpendicular to the vertical coordinate axes (z-).

In one embodiment, the robot-based treatment delivery system 1200 is robot-based LINAC system (as described above). In another embodiment, the robot-based treatment delivery system 1200 is an image-guided, robotic-based radiation treatment system (e.g., for performing radiosurgery), such as the CyberKnife® system developed by Accuray, Inc. of Sunnyvale, Calif. Alternatively, other treatment delivery systems may be used, such as gantry-based radiation treatment systems, such as illustrated in FIG. 13, a stereotactic frame system such as the GammaKnife®, available from Elekta of Sweden, or the like.

The robot-based patient positioning system 1250 includes a robotic arm 1252 and a treatment couch 1206 coupled to a distal end of the robotic arm 1252. In one embodiment, all of, or a portion of, the treatment couch 1206 is made of a radiolucent material so that the patient could be imaged through the treatment couch 1206. An exemplary imaging system that can be used with the system includes two x-ray imaging sources 1207, power supplies associated with each x-ray imaging source, one or two imaging detectors 1208, and controller 1201. The x-ray imaging sources 1207 may be mounted angularly apart, for example, about 90 degrees apart, and aimed through the treatment target (e.g., tumor within the patient) toward the detector(s) 1208. Alternatively, a single large detector may be used that would be illuminated by each x-ray source. In the single detector imaging system, the two x-ray sources 1207 may be positioned apart at an angle less than 90 degrees to keep both images on the single detector surface.

The detector(s) 1208 may be placed below the treatment target, e.g., on the floor, on the treatment couch 1206, or underneath the LINAC 1203, and the x-ray imaging sources 1207 may be positioned above the treatment target (e.g. the ceiling of the treatment room), to minimize magnification of the images and therefore the required size of the detector(s) 1208. In an alternative embodiment, the positions of the x-ray imaging sources 1207 and the detector(s) 1208 may be reversed, e.g. the x-ray imaging sources 1207 below the treatment target and the detector(s) 1208 above the treatment target. In another embodiment, the detector(s) 1208 are arranged in a manner such that they move into position for imaging and the moved out of the way during positioning of the LINAC 1203 or the treatment couch 1206 or during delivery of the radiation beam from the LINAC 1203.

The detector(s) 1208 may generate the image information of the patient and send it to the controller 1201. The controller 1201 performs all the imaging calculations to determine the patient's position with respect to the desired treatment position and generate corrections for the various DOF. The corrections could be automatically applied to the robot-based treatment delivery system 1200 to automatically align the LINAC 1203, and/or sent to the controller 1201 to automatically adjust the patient's position using the treatment couch 1206 and robotic arm 1252 relative to the LINAC 1203, and/or sent to the user interface unit for a user to manually adjust the patient's position relative to the LINAC 1203, using one or both of the robotic arms 1202 and 1252.

In one embodiment, the robotic arm 1252 includes a wrist assembly 1221, an elbow assembly 1231, a shoulder assembly 1241, a track mount assembly 1251, and a track 1261, and a column 1271. These components operate in a similar manner to the wrist assembly 1220, elbow assembly 1230, shoulder assembly 1240, track mount assembly 1250, and track 1260, and column 1270 of the robot-based treatment delivery system 1200 described above.

In one embodiment, the robotic arm 1202 and the robotic arm 1252 are identical robotic arms. In one embodiment, the robotic arms 1202 and 1252 each include four rotational DOF and one substantially linear DOF. In another embodiment, the robotic arms 1202 and 1252 each include five rotational DOF and one substantially linear DOF. Alternatively, the robotic arms 1202 and 1252 each include six rotational DOF and one substantially linear DOF. Alternatively, the robotic arms 1202 and 1252 may include dissimilar number and types of DOF. In another embodiment, the robotic arm 1202 and the robotic arm 1252 are dissimilar types of robotic arms.

As previously mentioned, the robot-based treatment delivery system 1200 including the controller 1201 may know the position of the LINAC 1203 through the sensor system and the position of the treatment target through the real time or near real time image data, and also knows the position of the treatment couch 1206 and may generate motion command signals for implementing corrective motions of either the robot-based patient positioning system 1250 or the robotic treatment delivery system 200 for aligning the treatment target with respect to the radiation source of the LINAC 1203. In one embodiment using a robot-based patient positioning system 1250, the corrective motions of the robot-based treatment delivery system 1200 may be dynamically coordinated with the motions of the treatment couch 1206 and robotic arm 1252 using the controller 1201, in a way as to maximize the workspace available to the system. By dynamically coordinating the motions of the treatment couch 1206 and the LINAC 1203 using the controller 1201, the available number of treatment targets increases due to the increased number of orientations and positions of the LINAC 1203 and the treatment couch 1206, which are free of obstructions, for example, by detectors 1208 and/or x-ray imaging sources 1207, robotic arms, or other equipment within the treatment room. In this embodiment, the robot-implemented movements of the LINAC 1203 are complemented by the corrective motions of the treatment couch 1206, so that the relative motion between the LINAC 1203 and the treatment couch 1206 ensures the delivery of the desired radiation pattern throughout the target region.

The robotic arm 1252 may position the LINAC 1203 to have a tool center position (TCP) or treatment target in multiple locations within the workspace or treatment area. The robotic arm 1252 of the robot-based patient positioning system 1250 may also position the isocenter or machine center of the patient positioning system 401 in multiple locations within the workspace or treatment area. The workspace or treatment area, however, may be limited by positioning restrictions, for example, obstructions caused by a possible collisions between either the LINAC 1203, the treatment couch 1206, or their corresponding robotic arms with components of the system, such as the LINAC 1203, treatment couch 1206, imaging sources 1207, detectors 1208, and/or robotic arms 1202 and 1252 or obstructions of the radiation beam of the LINAC 1203 with any of these above mentioned components. For example, the x-ray imaging sources 1207 may prevent the LINAC 1203 from being positioned where the x-ray imaging sources 1207 are mounted because positioning it there would result in a possible collision (e.g., collision obstructions). Similarly, the LINAC 1203 may not be positioned under the treatment couch 1206 due to the placement of the detectors 1208 (e.g., collision obstructions). Another example of a positioning restriction is obstructions of the radiation beam from the LINAC 1203 due to other components, for example, the detectors 1208 and/or x-ray imaging sources 1207 (e.g., beam obstructions).

In one embodiment, the controller 1201 may be configured to dynamically move independently, or in combination the LINAC 1203 along at least four rotational DOF and one substantially linear DOF using the robotic arm 1202, and the treatment couch 1206 along at least four rotational DOF and one substantially linear DOF using the robotic arm 1252 to dynamically coordinate orientation and position of the LINAC 1203 and the treatment couch 1206. The dynamic coordination of movement between the treatment couch 1206 and the LINAC 1203 may increase a number of treatment targets within a mechanical range of motion of the robotic arm.

The controller 1201 may be configured to position the LINAC 1203 and the treatment couch 1206 to create a treatment target in a previously obstructed location caused by a positioning restriction within a mechanical range of motion of the robotic arm 1202 of the LINAC 1203. Alternatively, the controller 1201 may be configured to position the LINAC 1203 and the treatment couch 1206 to create a treatment target in a previously obstructed location caused by a positioning restriction within a mechanical range of motion of the robotic arm 1252 of the treatment couch 1206. In one embodiment, the previously obstructed location may be caused by an obstruction of a possible collision, for example, between either the LINAC 1203, treatment couch 1206, their corresponding robotic arms with the robotic arm 1202, robotic arm 1252, the LINAC 1203, the LINAC 1203, x-ray imaging sources 1207, detectors 1208, and/or other components of the system. Alternatively, the previously obstructed location may be caused by an obstruction of the radiation beam of the LINAC with the robotic arm 1202, robotic arm 1252, the LINAC 1203, the LINAC 1203, x-ray imaging sources 1207, detectors 1208, and/or other components of the system.

In one embodiment, an anti-collision model may be embedded in the controller 1201 to ensure that the patient is not positioned in an orientation and/or position that might cause a possible collision between the treatment couch 1206 including the patient's body and other moving parts of the system.

The treatment couch 1206 of FIG. 12 is similar to the treatment couch 200, which includes the tabletop 201 and the lower-torso assembly 202, as described herein. The lower-torso assembly 202 is configured to adjust patients on the tabletop relative to a shoulder line (or head end) of the tabletop 201 of the treatment couch 1206.

FIG. 13 illustrates a system having a gantry-based radiation treatment system 1300 and a treatment couch 200 according to one embodiment. The gantry-based radiation treatment system 1300 is a gantry-based (isocentric) intensity modulated radiotherapy (IMRT) system, in which a radiation source (e.g., a LINAC) is mounted on the gantry in such a way that it rotates in a plane corresponding to an axial slice of the patient. Radiation may be delivered from several positions on the circular plane of rotation. The treatment couch 200 of FIG. 13 includes the tabletop 201 and the lower-torso assembly 202, as described herein. The lower-torso assembly 202 is configured to adjust patients on the tabletop relative to a shoulder line (or head end) of the tabletop 201 of the treatment couch 200. In one embodiment, the treatment couch 200 is coupled to a robotic arm (e.g., robotic arm 903), a stand (e.g., stand 1080), or other patient positioning systems known by those of ordinary skill in the art.

Figure 14:
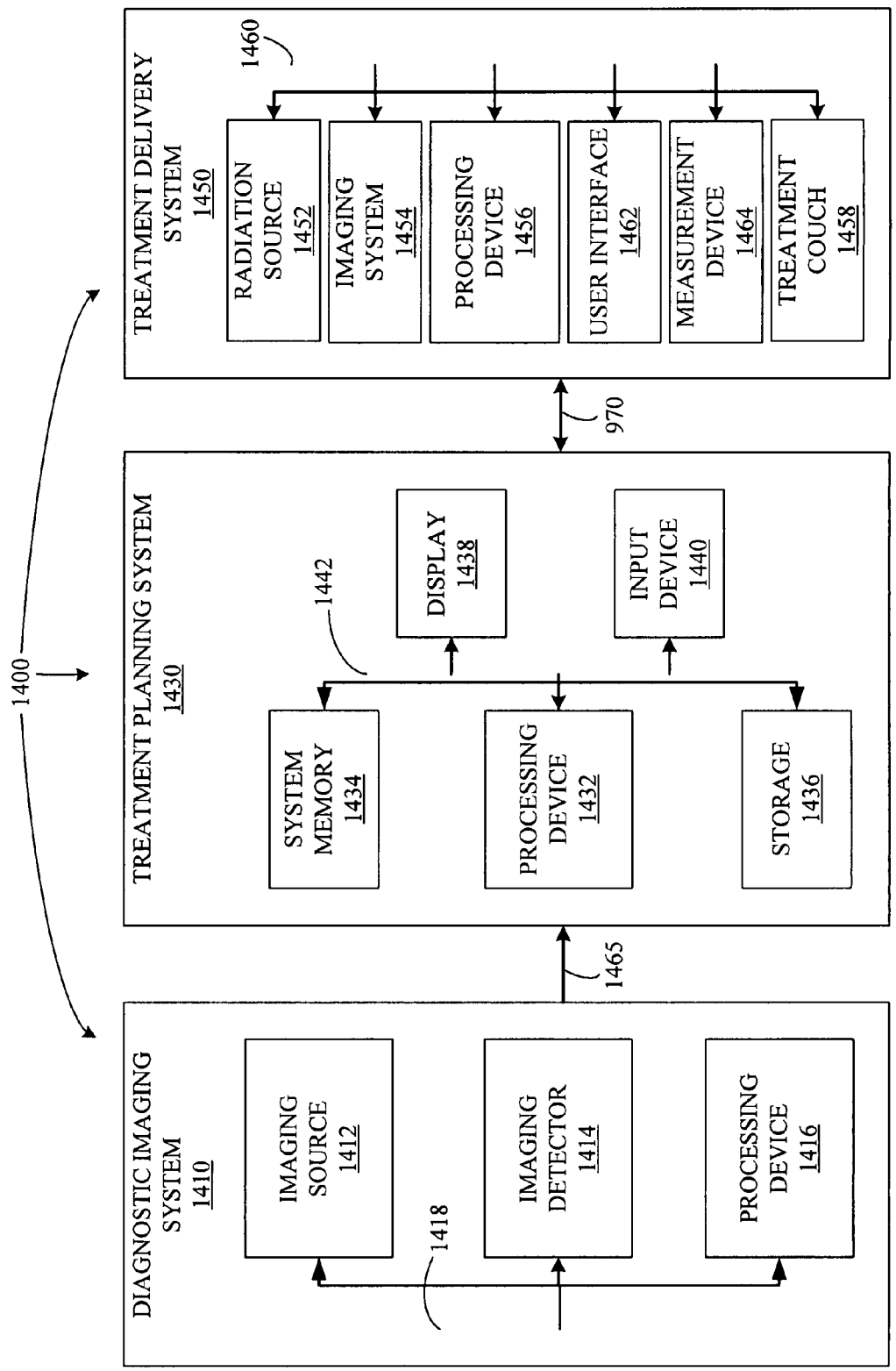
FIG. 14 illustrates a block diagram of one embodiment of a treatment system that may be used to perform radiation treatment in which embodiments of the present invention may be implemented.

FIG. 14 illustrates a block diagram of one embodiment of a treatment system 1400 that may be used to perform radiation treatment in which embodiments of the present invention may be implemented. The depicted treatment system 1400 includes a diagnostic imaging system 1410, a treatment planning system 1430, and a treatment delivery system 1450. In other embodiments, the treatment system 1400 may include fewer or more component systems.

The diagnostic imaging system 1410 is representative of any system capable of producing medical diagnostic images of a volume of interest (VOI) in a patient, which images may be used for subsequent medical diagnosis, treatment planning, and/or treatment delivery. For example, the diagnostic imaging system 1410 may be a computed tomography (CT) system, a single photon emission computed tomography (SPECT) system, a magnetic resonance imaging (MRI) system, a positron emission tomography (PET) system, a near infrared fluorescence imaging system, an ultrasound system, or another similar imaging system. For ease of discussion, any specific references herein to a particular imaging system such as a CT x-ray imaging system (or another particular system) is representative of the diagnostic imaging system 1410, generally, and does not preclude other imaging modalities, unless noted otherwise.

The illustrated diagnostic imaging system 1410 includes an imaging source 1412, an imaging detector 1414, and a processing device 1416. The imaging source 1412, imaging detector 1414, and processing device 1416 are coupled to one another via a communication channel 1418 such as a bus. In one embodiment, the imaging source 1412 generates an imaging beam (e.g., x-rays, ultrasonic waves, radio frequency waves, etc.) and the imaging detector 1414 detects and receives the imaging beam. Alternatively, the imaging detector 1414 may detect and receive a secondary imaging beam or an emission stimulated by the imaging beam from the imaging source (e.g., in an MRI or PET scan). In one embodiment, the diagnostic imaging system 1410 may include two or more diagnostic imaging sources 1412 and two or more corresponding imaging detectors 1414. For example, two x-ray sources 1412 may be disposed around a patient to be imaged, fixed at an angular separation from each other (e.g., 90 degrees, 45 degrees, etc.) and aimed through the patient toward corresponding imaging detectors 1414, which may be diametrically opposed to the imaging sources 1414. A single large imaging detector 1414, or multiple imaging detectors 1414, also may be illuminated by each x-ray imaging source 1414. Alternatively, other numbers and configurations of imaging sources 1412 and imaging detectors 1414 may be used.

The imaging source 1412 and the imaging detector 1414 are coupled to the processing device 1416 to control the imaging operations and process image data within the diagnostic imaging system 1410. In one embodiment, the processing device 1416 may communicate with the imaging source 1412 and the imaging detector 1414. Embodiments of the processing device 1416 may include one or more general-purpose processors (e.g., a microprocessor), special purpose processors such as a digital signal processor (DSP), or other type of devices such as a controller or field programmable gate array (FPGA). The processing device 1416 also may include other components (not shown) such as memory, storage devices, network adapters, and the like. In one embodiment, the processing device 1416 generates digital diagnostic images in a standard format such as the Digital Imaging and Communications in Medicine (DICOM) format. In other embodiments, the processing device 1416 may generate other standard or non-standard digital image formats.

Additionally, the processing device 1416 may transmit diagnostic image files such as DICOM files to the treatment planning system 1430 over a data link 1460. In one embodiment, the data link 1460 may be a direct link, a local area network (LAN) link, a wide area network (WAN) link such as the Internet, or another type of data link. Furthermore, the information transferred between the diagnostic imaging system 1410 and the treatment planning system 1430 may be either pulled or pushed across the data link 1460, such as in a remote diagnosis or treatment planning configuration. For example, a user may utilize embodiments of the present invention to remotely diagnose or plan treatments despite the existence of a physical separation between the system user and the patient.

The illustrated treatment planning system 1430 includes a processing device 1432, a system memory device 1434, an electronic data storage device 1436, a display device 1438, and an input device 1440. The processing device 1432, system memory 1434, storage 1436, display 1438, and input device 1440 may be coupled together by one or more communication channel 1442 such as a bus.

The processing device 1432 receives and processes image data. The processing device 1432 also processes instructions and operations within the treatment planning system 1430. In certain embodiments, the processing device 1432 may include one or more general-purpose processors (e.g., a microprocessor), special purpose processors such as a digital signal processor (DSP), or other types of devices such as a controller or field programmable gate array (FPGA).

In particular, the processing device 1432 may be configured to execute instructions for performing treatment operations discussed herein. For example, the processing device 1432 may identify a non-linear path of movement of a target within a patient and develop a non-linear model of the non-linear path of movement. In another embodiment, the processing device 1432 may develop the non-linear model based on multiple position points and multiple direction indicators. In another embodiment, the processing device 1432 may generate multiple correlation models and select one of the multiple models to derive a position of the target. Furthermore, the processing device 1432 may facilitate other diagnosis, planning, and treatment operations related to the operations described herein.

In one embodiment, the system memory 1434 may include random access memory (RAM) or other dynamic storage devices. As described above, the system memory 1434 may be coupled to the processing device 1432 by the communication channel 1442. In one embodiment, the system memory 1434 stores information and instructions to be executed by the processing device 1432. The system memory 1434 also may be used for storing temporary variables or other intermediate information during execution of instructions by the processing device 1432. In another embodiment, the system memory 1434 also may include a read only memory (ROM) or other static storage device for storing static information and instructions for the processing device 1432.

In one embodiment, the storage 1436 is representative of one or more mass storage devices (e.g., a magnetic disk drive, tape drive, optical disk drive, etc.) to store information and instructions. The storage 1436 and/or the system memory 1434 also may be referred to as machine readable media. In a specific embodiment, the storage 1436 may store instructions to perform the modeling operations discussed herein. For example, the storage 1436 may store instructions to acquire and store data points, acquire and store images, identify non-linear paths, develop linear and/or non-linear correlation models, and so forth. In another embodiment, the storage 1436 may include one or more databases.

In one embodiment, the display 1438 may be a cathode ray tube (CRT) display, a liquid crystal display (LCD), or another type of display device. The display 1438 displays information (e.g., a two-dimensional or 3D representation of the VOI) to a user. The input device 1440 may include one or more user interface devices such as a keyboard, mouse, trackball, or similar device. The input device(s) 1440 may also be used to communicate directional information, to select commands for the processing device 1432, to control cursor movements on the display 1438, and so forth.

Although one embodiment of the treatment planning system 1430 is described herein, the described treatment planning system 1430 is only representative of an exemplary treatment planning system 1430. Other embodiments of the treatment planning system 1430 may have many different configurations and architectures and may include fewer or more components. For example, other embodiments may include multiple buses, such as a peripheral bus or a dedicated cache bus. Furthermore, the treatment planning system 1430 also may include Medical Image Review and Import Tool (MIRIT) to support DICOM import so that images can be fused and targets delineated on different systems and then imported into the treatment planning system 1430 for planning and dose calculations. In another embodiment, the treatment planning system 1430 also may include expanded image fusion capabilities that allow a user to plan treatments and view dose distributions on any one of various imaging modalities such as MRI, CT, PET, and so forth. Furthermore, the treatment planning system 1430 may include one or more features of convention treatment planning systems.

In one embodiment, the treatment planning system 1430 may share a database on the storage 1436 with the treatment delivery system 1450 so that the treatment delivery system 1450 may access the database prior to or during treatment delivery. The treatment planning system 1430 may be linked to treatment delivery system 1450 via a data link 1470, which may be a direct link, a LAN link, or a WAN link, as discussed above with respect to data link 1460. Where LAN, WAN, or other distributed connections are implemented, any of components of the treatment system 1400 may be in decentralized locations so that the individual systems 1410, 1430 and 1450 may be physically remote from one other. Alternatively, some or all of the functional features of the diagnostic imaging system 1410, the treatment planning system 1430, or the treatment delivery system 1450 may be integrated with each other within the treatment system 1400.

The illustrated treatment delivery system 1450 includes a radiation source 1452, an imaging system 1454, a processing device 1456, and a treatment couch 1458. The radiation source 1452, imaging system 1454, processing device 1456, and treatment couch 1458 may be coupled to one another via one or more communication channels 1460. One example of a treatment delivery system 1450 is shown and described in more detail with reference to FIG. 12.

In one embodiment, the radiation source 1452 is a therapeutic or surgical radiation source 1452 to administer a prescribed radiation dose to a target volume in conformance with a treatment plan. In one embodiment, the radiation source 1452 is the LINAC 1203, as described herein. Alternatively, the radiation source 1452 may be other types of radiation sources known by those of ordinary skill in the art. For example, the target volume may be an internal organ, a tumor, a region. As described above, reference herein to the target, target volume, target region, target area, or internal target refers to any whole or partial organ, tumor, region, or other delineated volume that is the subject of a treatment plan.

In one embodiment, the imaging system 1454 of the treatment delivery system 1450 captures intra-treatment images of a patient volume, including the target volume, for registration or correlation with the diagnostic images described above in order to position the patient with respect to the radiation source. Similar to the diagnostic imaging system 1410, the imaging system 1454 of the treatment delivery system 1450 may include one or more sources and one or more detectors.

The treatment delivery system 1450 also may include a processing device 1456 to control the radiation source 1452, the imaging system 1454, and a treatment couch 1458, which is representative of any patient support device. In one embodiment, the treatment couch 1458 is the treatment couch 200 or 1206 coupled to the robotic arm 1202 or 1252, as described herein. In another embodiment, the treatment couch 1458 is the treatment couch coupled to the robotic arm 106, as described herein. Alternatively, other types of patient support devices can be used. In one embodiment, the radiation source 1452 is coupled to a first robotic arm (e.g., robotic arm 1202), and the treatment couch 1458 is coupled to a second robotic arm (e.g., robotic arm 1252). The first and second robotic arms may be coupled to the same controller (e.g., controller 1201) or to separate controllers. In one embodiment, the first and second robotic arms are identical robotic arms. In one embodiment, the first and second robotic arms each include four rotational DOF and one substantially linear DOF. In another embodiment, the first and second robotic arms each include five rotational DOF and one substantially linear DOF. Alternatively, the first and second robotic arms each include six rotational DOF and one substantially linear DOF. Alternatively, the first and second robotic arms may include dissimilar number and types of DOF. In another embodiment, the first and second robotic arms are dissimilar types of robotic arms. Alternatively, only the first robotic arm is used to move the LINAC 1203 with respect to the treatment couch 1206.

The processing device 1456 may include one or more general-purpose processors (e.g., a microprocessor), special purpose processors such as a digital signal processor (DSP), or other devices such as a controller or field programmable gate array (FPGA). Additionally, the processing device 1456 may include other components (not shown) such as memory, storage devices, network adapters, and the like.

The illustrated treatment delivery system 1450 also includes a user interface 1462 and a measurement device 1464. In one embodiment, the user interface 1462 is a graphical user interface. Alternatively, other user interfaces may be used. In one embodiment, the user interface 1462 allows a user to interface with the treatment delivery system 1450. In particular, the user interface 1462 may include input and output devices such as a keyboard, a display screen, and so forth. The measurement device 1464 may be one or more devices that measure external factors such as the external factors described above, which may influence the radiation that is actually delivered to the target region 20. Some exemplary measurement devices include a thermometer to measure ambient temperature, a hygrometer to measure humidity, a barometer to measure air pressure, or any other type of measurement device to measure an external factor.

FIG. 15 illustrates a flow chart of one embodiment of a method 1500 for adjusting a patient along a longitudinal direction 206 relative to a shoulder line 207 of a tabletop 201 of a treatment couch 200. The method includes loading a patient onto a treatment couch having a tabletop and a lower-torso assembly, operation 1501, and adjusting the patient along a longitudinal direction 206 relative to a shoulder line 207 of the tabletop 201 using the lower-torso assembly (e.g., 202, 302, 402, or 502) while the lower-torso assembly remains outside a radiolucent region 204 of the tabletop 201, operation 1502. It should be noted that operation 1501 may be performed after the operation 1502, or vice versa. In one embodiment, adjusting the patient includes manually adjusting the position of the lower-torso assembly to adjust the patient relative to the shoulder line 207. In one embodiment, the shoulders of the patient are positioned at the shoulder line 207 regardless of the height of the patient using the lower-torso assembly. In another embodiment, the patient's shoulders are substantially aligned with the shoulder line 207. In another embodiment, the upper half of the patient is adjusted relative to the shoulder line 207 of the tabletop 201. Alternatively, the patient may be adjusted relative to the head end 205 of the tabletop 201.

In one embodiment, positioning the shoulders of that patient at the shoulder line 207 includes moving the lower-torso assembly in a translational direction that is substantially perpendicular to the shoulder line 207, and locking the lower-torso assembly to the tabletop 201 when the shoulders of the patient are at the shoulder line 207.

In another embodiment, the method 1500 further includes converting the lower-torso assembly between a bolster seat (e.g., bolster seat configuration 700) and a flat tabletop (e.g., flat tabletop configuration 600). In one embodiment, converting the lower-torso assembly includes configuring the lower-torso assembly to be substantially flat with respect to a plane of the top surface 218 of the tabletop 201. In another embodiment, converting the lower-torso assembly includes configuring an upper section 602 of the lower-torso assembly to be at an angle with respect to the plane of the top surface 218 of the tabletop 201. The operation of converting the lower-torso assembly, in one embodiment, includes moving a first slide bar, coupled to a first hinge, along a slot 208 of the tabletop 201, and moving a second slide bar, coupled to a second hinge, along a slot 211 of the first slide bar. By moving the first and second slide bars moves the link member, which is coupled to the first and second hinges, between a flat configuration and a seat configuration. The operation may further include locking relative positions of the first slide bar and the second slide bar to configure the lower-torso assembly to be in at least one of a seat configuration, a flat configuration, or an intermediate configuration, which is between the seat and flat configurations. In another embodiment, the operation of converting the lower-torso assembly includes moving hinge centers of the first and second hinges toward one another to form the bolster seat with the link member, and moving hinge centers of the first and second hinge centers away from one another to configure the link member to be substantially flat with respect to a top surface 218 of the tabletop to form the flat tabletop. The operation may further include locking the positions of the first and second hinges to configure the lower-torso assembly to be in at least one of the seat configuration, the flat configuration, or the intermediate configuration.

In another embodiment, the method includes converting the lower-torso assembly between a seat configuration (e.g., bolster seat configuration 700) and a flat configuration (e.g., flat tabletop configuration 600). In the flat configuration, a top surface of the lower-torso assembly is configured to be flat along the substantially same plane as a top surface 218 of the tabletop 201. In the seat configuration, a top surface 602 of an upper section 231 of the lower-torso assembly is positioned to be at an angle with respect to the plane of the top surface 218. In one embodiment, the angle is approximately 120 degrees between the top surface 602 of the upper section 231 and the top surface 218 of the tabletop 201. In another embodiment, the angel is approximately 135 degrees between the top surface 602 of the upper section 231 and the top surface 218 of the tabletop 201.

The method may further include positioning the patient in a treatment room or with respect to a radiation source in a treatment position. It should be noted that the patient may be positioned in a treatment room or with respect to the radiation source before or after the patient has been adjusted on the treatment couch relative to the head end (or shoulder line). For example, after the patient is loaded onto the couch, the patient may be positioned on the couch relative to the head end (or shoulder line) of the treatment couch before the treatment couch is positioned in a treatment room relative to a radiation source of a radiation treatment system.

FIG. 16 illustrates a flow chart of one embodiment of a method 1600 for operation of a robotic treatment couch 200. Method 1600 includes moving a treatment couch having a tabletop and a lower-torso assembly (e.g., 202, 302, 402, or 502) along one or more degrees of freedom using a first robotic arm (e.g., 1252), operation 1601, and adjusting a patient along a longitudinal direction 206 relative to a shoulder line 207 of the tabletop 201 of the treatment couch 200 using the lower-torso assembly while the lower-torso assembly remains outside a radiolucent region 204 of the tabletop, operation 1602. The method may further include moving a LINAC with respect to a treatment target of the patient using a second robotic arm (e.g., 1202). The method may further include providing an imaging system having an imaging field of view for imaging an imaging zone of a patient. The imaging zone may be from the head to the lowest point of the rear pelvic area of the patient when in the bolster seat configuration (e.g., 700) or from the head to the mid thigh area of the patient when in the flat tabletop configuration (e.g., 600). Alternatively, the imaging zone may be other areas of interest of the patient. In one embodiment, the lower-torso assembly is configured to remain outside the imaging zone of the patient regardless of the height of the patient. In another embodiment, a portion (e.g., lower-torso assembly) of the treatment couch 200 is maintained substantially outside the imaging field of view for all supported treatment positions by adjusting the patient along the longitudinal direction 206 relative to the shoulder line 207 of the tabletop 201 using the lower-torso assembly.

In one embodiment, adjusting the patient includes the operations of the method 1500 described above. In another embodiment, the method further includes configuring the lower-torso assembly to be substantially flat with respect to a plane of a top surface 218 of the tabletop 201. In another embodiment, the method further includes configuring a section (e.g., upper section 231) of the lower-torso assembly to be at an angle with respect to the top surface 218 of the tabletop 201.

In one embodiment, a method, implementing the patient positioning and radiation treatment systems, may include providing a treatment couch coupled to a first robotic arm, in a first operation, moving the treatment couch along one or more rotational degrees of freedom, in a second operation, and moving an upper-half of a patient relative to a head end of the treatment couch, in a third operation. The method may further include providing a linear accelerator coupled to a second robotic arm, the second robotic arm to move the linear accelerator with respect to a treatment target of the patient, in a fourth operation. The method may further include providing an imaging system having an imaging field of view, and maintaining the treatment couch substantially outside of the imaging field of view for all supported treatment positions by moving the upper-half of the patient relative to the head end of the treatment couch.

It should be noted that the embodiments described herein are not limited to radiation treatment systems. The embodiments described herein may also be used in connection with other medical treatment, such as a positioning couch for an operating room, a positioning couch for a diagnostic x-ray machine, a positioning chair for dental procedures, treatment chairs, and other medical patient support or positioning couches.

As previously discussed, the embodiments described herein are not limited to a treatment couch used for medical treatment. The embodiments described herein may also be used in connection with other non-medical treatment systems, such as a couch (which may otherwise be referred to as a chair, or otherwise, in particular fields of application) for a simulator, video or arcade game system. The embodiments described herein may also be used as a loading mechanism for an amusement park ride, for military machinery, or for heavy machinery to position, reposition, align, or adjust a body (e.g., human or animal body) into a confined space (e.g., into a gunner position of a tank) in a longitudinal direction. Alternatively, the embodiments described herein may be used in other types of applications that involve positioning a body with respect to one end of a couch in a translational direction.

Embodiments of the present invention include various operations, which will be described below. These operations may be performed by hardware components, software, firmware, or a combination thereof. As used herein, the term "coupled to" may mean coupled directly or indirectly through one or more intervening components. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems.

A "target" as discussed herein may be an anatomical feature(s) of a patient such as a pathological anatomy (e.g., tumor, lesion, vascular malformation, nerve disorder, etc.) or normal anatomy and may include one or more non-anatomical reference structures.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of a beam(s) and "target" may refer to a non-anatomical object or area.

The controller(s) described herein may include one or more general-purpose processing devices such as a microprocessor or central processing unit, or the like. Alternatively, the controller may include one or more special-purpose processing devices such as a digital signal processor (DSP), an application specific integrated circuit (ASIC), a field programmable gate array (FPGA), or the like. In an alternative embodiment, for example, the controller may be a network processor having multiple processors including a core unit and multiple microengines. Additionally, the controller may include any combination of general-purpose processing device(s) and special-purpose processing device(s).

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
  loading a patient onto a treatment couch having a tabletop and a lower-torso assembly;
  adjusting the patient along a longitudinal direction relative to a shoulder line of the tabletop using the lower-torso assembly while the lower-torso assembly remains outside a radiolucent region of the tabletop; and
  converting the lower-torso assembly between a bolster seat and a flat tabletop.

2. The method of claim 1, wherein adjusting the patient along the longitudinal direction comprises manually adjusting the position of the lower-torso assembly to adjust the patient along the longitudinal direction relative to the shoulder line.

3. The method of claim 1, wherein adjusting the patient comprises adjusting an upper half of the patient relative to the shoulder line of the tabletop.

4. The method of claim 1, wherein adjusting the patient comprises positioning the shoulders of the patient at the shoulder line regardless of the height of the patient.

5. The method of claim 4, wherein positioning the shoulders comprises:
  moving the lower-torso assembly in a translational direction that is substantially perpendicular to the shoulder line; and locking the lower-torso assembly to the tabletop when the shoulders of the patient are at the shoulder line.

6. The method of claim 1, wherein converting the lower-torso assembly comprises:
configuring the lower-torso assembly to be substantially flat with respect to a plane of the top surface of the tabletop; and
configuring an upper section of the lower-torso assembly to be at an angle with respect to the plane of the top surface of the tabletop.

7. The method of claim 1, wherein converting the lower-torso assembly comprises:
moving a first slide bar, coupled to a first hinge, along a slot of the tabletop; and
moving a second slide bar, coupled to a second hinge, along a slot of the first slide bar, wherein moving the first and second slide bars comprises moving a link member, coupled to the first and second hinges, between a flat configuration and a seat configuration.

8. The method of claim 7, wherein converting the lower-torso assembly further comprises locking relative positions of the first slide bar and the second slide bar, and wherein the relative positions configure the lower-torso assembly to be in at least one of a seat configuration, a flat configuration, or an intermediate configuration between the seat configuration and the flat configuration.

9. The method of claim 7, wherein converting the lower-torso assembly further comprises:
moving hinge centers of the first and second hinges towards one another to form the bolster seat with the link member; and
moving hinge centers of the first and second hinges away from one another to configure the link member to be substantially flat with respect to a top surface of the tabletop to form the flat tabletop.

10. The method of claim 9, wherein converting the lower-torso assembly further comprises locking the positions of the first and second hinges, and wherein the relative positions configure the lower-torso assembly to be in at least one of a seat configuration, a flat configuration, or an intermediate configuration between the seat configuration and the flat configuration.

11. The method of claim 1, wherein the lower-torso assembly is converted before loading the patient onto the treatment couch.

12. The method of claim 1, wherein the lower-torso assembly is converted after loading the patient onto the treatment couch.

13. A method, comprising:
loading a patient onto a treatment couch having a tabletop and a lower-torso assembly;
adjusting the patient along a longitudinal direction relative to a shoulder line of the tabletop using the lower-torso assembly while the lower-torso assembly remains outside a radiolucent region of the tabletop; and
converting the lower-torso assembly between a seat configuration and a flat configuration, wherein a top surface of the lower-torso assembly is configured to be flat along the substantially same plane as a top surface of the tabletop in the flat configuration, and wherein a top surface of an upper section of the lower-torso assembly is positioned to be at an angle with respect to the plane of the top surface of the tabletop in the seat configuration.

14. An apparatus, comprising:
a tabletop having a radiolucent region; and
a lower-torso assembly coupled to the tabletop, wherein the lower-torso assembly comprises:
a first slide member coupled to a slot of the tabletop;
a second slide member coupled to a slot of the first slide member; and
a link member coupled to the first slide member and the second slide member, wherein the first slide member, second slide member, and link member are disposed outside the radiolucent region of the tabletop.

15. The apparatus of claim 14, further comprising a locking mechanism coupled to the first slide member and the tabletop, wherein the first slide member is configured to slide along the slot of the tabletop when the first locking mechanism is disengaged to adjust a patient along a longitudinal direction relative to a shoulder line of the tabletop while the lower-torso assembly remains outside the radiolucent region of the tabletop.

16. The apparatus of claim 14, wherein the link member comprises an upper section and a lower section, wherein top surfaces of the upper and lower sections of the link member are configured to be flat with respect to a top surface of the tabletop in a first configuration, and wherein the top surface of the upper section of the link member is configured to be at an angle with respect to the top surface of the tabletop in a second configuration.

17. The apparatus of claim 14, wherein the first slide member is a first slide bar, wherein the second slide member is a second slide bar, and wherein the apparatus further comprises:
a first hinge coupled to the first slider bar; and
a second hinge coupled to the second slide bar; wherein the link member is coupled to the first hinge and the second hinge.

18. The apparatus of claim 14, further comprising a first locking mechanism coupled to the first slide bar, wherein the first locking mechanism is configured to lock relative positions of the first slide bar and the second slide bar.

19. The apparatus of claim 18, wherein the relative positions comprises at least one of a seat configuration, a flat configuration, or an intermediate configuration between the seat configuration and the flat configuration.

20. The apparatus of claim 19, wherein at the flat configuration the first slide bar and the second slide bar are locked with their hinge centers at a distance substantially equal to the length of the link member, and wherein at the seat configuration the first and second slide bars are locked with their hinge centers at a distance less than the length of the link member.

21. The apparatus of claim 20, wherein the first locking mechanism is configured to allow the first slide bar and the second slide bar to slide the hinge centers of the first and second hinges relative to one another when the first locking mechanism is disengaged, and to prevent the first slide bar and the second slide bar to slide the hinge centers of the first and second hinges relative to one another when the first locking mechanism is engaged.

22. The apparatus of claim 18, wherein the first locking mechanism is a pin.

23. The apparatus of claim 22, wherein the pin is a spring pin.

24. The apparatus of claim 18, further comprising a second locking mechanism coupled to the first slide bar and the tabletop, wherein the second locking mechanism is configured to lock the relative position of the first slide bar and the tabletop, and wherein the lower-torso assembly is configured to move along the longitudinal direction of the tabletop when the second locking mechanism is disengaged from the tabletop.

25. The apparatus of claim 24, wherein the patient load is carried in shear by the second locking mechanism on the first slide bar and in moment by the boundaries of the slot of the tabletop.

26. The apparatus of claim 24, wherein the tabletop comprises a plurality of height positions at which the second locking mechanism locks the first slide member to the tabletop.

27. The apparatus of claim 26, wherein the plurality of height positions comprise at least a first height position and a second height position, wherein the first height position is configured to position a female having the one percentile female height to the shoulder line of the tabletop, and wherein the second height position is configured to position a male having the 99$^{th}$ percentile male height to the shoulder line of the tabletop.

28. The apparatus of claim 24, wherein the second locking mechanism is a spring pin.

29. The apparatus of claim 28, wherein the pin is a spring pin.

30. The apparatus of claim 17, wherein the link member comprises one or more rigid links.

31. The apparatus of claim 17, wherein the link member comprises:
a first rigid link coupled to the first hinge; and
a second rigid link coupled to the second hinge and to the first rigid link using a third hinge, wherein the first and second rigid links are configured to rotate relative to each other while being fixed in the other direction at the first and second hinges, respectively.

32. The apparatus of claim 17, wherein the link member comprises:
a first rigid link coupled to the first hinge;
a second rigid link coupled to the first rigid link using a third hinge; and
a third rigid link coupled to the second hinge and the second rigid link using a fourth hinge, wherein the first, second, and third rigid links are configured to rotate relative to each other.

33. The apparatus of claim 32, wherein the rotation of the first, second, and third rigid links are restricted.

34. The apparatus of claim 14, wherein the first slide member is a seat positioning bar, wherein the second slide member is a bolster bar, wherein the link member comprises a seat pan and a lower-leg support member, and wherein the apparatus further comprises:
a first hinge coupled to the seat positioning bar and the seat pan;
a second hinge coupled to the bolster bar and the lower-leg support member; and
a third hinge coupled to the seat pan and the lower-leg support member.

35. The apparatus of claim 34, further comprising a foot extension coupled to the lower-leg support member, wherein the foot extension is configured to provide support beyond the surface area of the lower-leg support member.

36. The apparatus of claim 34, wherein the seat pan comprises one or more patient handles.

37. The apparatus of claim 34, wherein the radiolucent region of the tabletop is substantially from a head end of the tabletop to substantially the first hinge.

38. The apparatus of claim 34, wherein the radiolucent region of the tabletop is substantially from a head end of the tabletop to substantially the seat pan.

39. The apparatus of claim 34, wherein all components of the lower-torso assembly are disposed outside the radiolucent region of the tabletop.

40. The apparatus of claim 14, wherein the lower-torso assembly is metal, and wherein substantially all of the metal of the lower-torso assembly is outside of the radiolucent region of the tabletop.

41. The apparatus of claim 14, when the lower-torso assembly is configured to be a bolster seat on the tabletop in a first configuration, and wherein the bolster seat is configured to be positioned at a plurality of positions along a longitudinal direction relative to a shoulder line of the tabletop when in the first configuration.

42. The apparatus of claim 41, wherein the bolster seat is configured to have a seat pan of approximately 120 degrees between a top surface of the seat pan and a top surface of the tabletop.

43. The apparatus of claim 41, wherein the bolster seat is configured to have a seat pan of approximately 135 degrees between a top surface of the seat pan and a top surface of the tabletop.

44. The apparatus of claim 14, when the lower-torso assembly is configured to be a flat tabletop on the tabletop in a second configuration.

45. The apparatus of claim 14, wherein the tabletop and the lower-torso assembly are configured to provide a support assembly that has a flat surface upon which the patient is disposed in a first configuration, and wherein the tabletop and the lower-torso assembly are configured to provide a support assembly having a seat to support a lower-torso area of the patient in a second configuration.

46. The apparatus of claim 14, wherein the first slide member is an upper-seat bracket, wherein the second slide member is a lower-seat bracket, and wherein the upper-seat bracket and the lower-seat bracket are configured to move relative to one another in along the longitudinal direction relative to the shoulder line of the tabletop when a first locking mechanism is disengaged, and to move together along the longitudinal direction relative to the shoulder line of the tabletop when a second locking mechanism is disengaged.

47. The apparatus of claim 46, wherein the link section comprises:
a seat pan coupled to the upper-seat bracket by a first hinge; and
a lower-leg support coupled to the lower-seat bracket by a second hinge, and wherein the seat pan and the lower-leg support are coupled together by a third hinge.

48. The apparatus of claim 47, wherein the seat pan comprises one or more patient handles.

49. The apparatus of claim 47, wherein the lower-torso assembly comprises a foot extension coupled to the lower-leg support, and wherein the foot extension is configured to support a lower portion of the legs of the patient when the legs of the patient go beyond the lower-leg support.

50. The apparatus of claim 46, wherein the first locking mechanism is a seat creation handle, wherein the seat creation handle is configured to allow the lower-torso assembly to convert between a bolster seat on the tabletop and a flat tabletop when disengaged, wherein the second locking mechanism is a seat motion handle, and wherein the seat motion handle is configured to allow the lower-torso assembly to move along the longitudinal direction relative to the shoulder line of the tabletop when disengaged.

51. An apparatus, comprising:
a tabletop; and
means for positioning patients of various heights at a shoulder line on the tabletop while the means for positioning patients remain outside a radiolucent region of the tabletop, and wherein the radiolucent region is above the lowest point of the rear pelvic area of the human body, wherein the means for positioning patients comprises:
  means for moving a patient in the longitudinal direction relative to the shoulder line of the tabletop, wherein the means for moving the patient remain outside the radiolucent region of the tabletop; and
  means for converting the positioning means between a flat configuration and a bolster seat configuration.

52. The apparatus of claim 51, wherein the means for positioning patients increases an available workspace of a radiation source of a radiation treatment system.

53. The apparatus of claim 51, wherein the means for positioning patients remain outside an imaging zone of the patient for the patients of various heights.

54. The apparatus of claim 51, wherein the means for positioning patients comprises means for not entering the radiolucent region of the tabletop.

55. The apparatus of claim 51, wherein the means for positioning patients comprises means for not obstructing an imaging zone of the patient for the patients of various heights, and wherein the imaging zone is above at least the highest point of the leg posterior to the hip of the human body.

56. The apparatus of claim 51, wherein the means for positioning patients comprises means for supporting a patient load up to approximately 500 pounds (lbs).

57. A system, comprising:
  a radiation treatment system comprising a radiation source; and
  a treatment couch upon which a patient is disposed, wherein the treatment couch comprises:
    a tabletop having a radiolucent region; and
    a lower-torso assembly coupled to the tabletop, wherein the lower-torso assembly comprises:
      a first slide member coupled to a slot of the tabletop;
      a second slide member coupled to a slot of the first slide member; and
      a link member coupled to the first slide member and the second slide member, wherein the slots of the tabletop and the slot of the first slide member are disposed outside the radiolucent region of the tabletop.

58. The system of claim 57, wherein the lower-torso assembly further comprises a locking mechanism coupled to the first slide member and the tabletop, wherein the first slide member is configured to slide along the slot of the tabletop when the first locking mechanism is disengaged to adjust a patient along a longitudinal direction relative to a shoulder line of the tabletop while the lower-torso assembly remains outside the radiolucent region of the tabletop.

59. The system of claim 57, wherein the radiation treatment system is at least one of a gantry-based radiation treatment system or a robot-based linear accelerator system.

60. The system of claim 57, further comprising a patient positioning system to position the patient with respect to the radiation source of the radiation treatment system, wherein the patient positioning system comprises a robotic arm coupled to the treatment couch, and wherein the robotic arm is configured to move the treatment couch along one or more degrees of freedom.

61. The system of claim 60, wherein the robotic arm is configured to move the treatment couch along at least three degrees of freedom.

62. The system of claim 60, wherein the robotic arm is configured to move the treatment couch along five degrees of freedom.

63. A system, comprising:
  a computed tomography (CT) scanner; and
  a treatment couch upon which a patient is disposed, wherein the treatment couch comprises:
    a tabletop having a radiolucent region; and
    a lower-torso assembly coupled to the tabletop, wherein the lower-torso assembly comprises:
      a first slide member coupled to a slot of the tabletop;
      a second slide member coupled to a slot of the first slide member; and
      a link member coupled to the first slide member and the second slide member, wherein the slots of the tabletop and the slot of the first slide member are disposed outside the radiolucent region of the tabletop.

64. The system of claim 63, wherein the lower-torso assembly further comprises a locking mechanism coupled to the first slide member and the tabletop, wherein the first slide member is configured to slide along the slot of the tabletop when the first locking mechanism is disengaged to adjust a patient along a longitudinal direction relative to a shoulder line of the tabletop while the lower-torso assembly remains outside the radiolucent region of the tabletop.

65. The system of claim 63, further comprising a patient positioning system to position the patient with respect to the CT scanner, wherein the patient positioning system comprises a robotic arm coupled to the treatment couch, and wherein the robotic arm is configured to move the treatment couch along one or more degrees of freedom.

66. The system of claim 65, wherein the robotic arm is configured to move the treatment couch along at least three degrees of freedom.

67. The system of claim 65, wherein the robotic arm is configured to move the treatment couch along five degrees of freedom.

68. An apparatus, comprising:
  a treatment couch, to load a patient thereon, having a tabletop and a lower-torso assembly, wherein the lower-torso assembly is configured to:
    adjust the patient along a longitudinal direction relative to a shoulder line of the tabletop while the lower-torso assembly remains outside a radiolucent region of the tabletop; and
    convert the lower-torso assembly between a bolster seat and a flat tabletop.

* * * * *